US012692496B2

(12) United States Patent (10) Patent No.: US 12,692,496 B2
Khanna et al. (45) Date of Patent: Jul. 28, 2026

(54) COMPOSITIONS AND METHODS FOR MODULATING RPGR EXPRESSION

(71) Applicant: University of Massachusetts, Westborough, MA (US)

(72) Inventors: Hemant Khanna, Worcester, MA (US); Laura Moreno Leon, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 882 days.

(21) Appl. No.: 17/909,148

(22) PCT Filed: Mar. 4, 2021

(86) PCT No.: PCT/US2021/020875
§ 371 (c)(1),
(2) Date: Sep. 2, 2022

(87) PCT Pub. No.: WO2021/178668
PCT Pub. Date: Sep. 10, 2021

(65) Prior Publication Data
US 2023/0142852 A1 May 11, 2023

Related U.S. Application Data

(60) Provisional application No. 62/984,851, filed on Mar. 4, 2020, provisional application No. 62/985,286, filed on Mar. 4, 2020.

(51) Int. Cl.
| | |
|---|---|
| *C07H 21/02* | (2006.01) |
| *A61P 27/02* | (2006.01) |
| *C12N 15/113* | (2010.01) |
| *C12N 15/86* | (2006.01) |

(52) U.S. Cl.
CPC ............ *C12N 15/113* (2013.01); *A61P 27/02* (2018.01); *C12N 15/86* (2013.01); *C12N 2310/141* (2013.01); *C12N 2750/14143* (2013.01); *C12N 2750/14171* (2013.01)

(58) Field of Classification Search
CPC ........................ C12N 15/113; C12N 2310/141
See application file for complete search history.

(56) References Cited

U.S. PATENT DOCUMENTS

| | | | |
|---|---|---|---|
| 2008/0125583 A1* | 5/2008 | Rigoutsos | G16B 30/00 536/22.1 |
| 2012/0040004 A1* | 2/2012 | Howard | A61P 43/00 977/773 |
| 2012/0302626 A1 | 11/2012 | Dave et al. | |
| 2014/0171484 A1 | 6/2014 | Califano et al. | |
| 2016/0319354 A1 | 11/2016 | Tocigl et al. | |

FOREIGN PATENT DOCUMENTS

WO WO-2016145345 A1 * 9/2016 ......... A61K 38/1709

OTHER PUBLICATIONS

Gakovic et al. (Human Molecular Genetics, 2011, vol. 20, No. 24, 4840-4850).*
Akache et al. (Journal of Virology, Oct. 2006, p. 9831-9836).*
Seyhan et al. (Mol. BioSyst., 2016, 12, 295-312).*
International Search Report and Written Opinion for Application No. PCT/US2021/020875, mailed May 27, 2021.
International Preliminary Report on Patentability for Application No. PCT/US2021/020875, mailed Sep. 15, 2022.
Leon et al., Regulation of RPGR (retinitis pigmentosa GTPase regulator) isoform expression by miRNAs: insights into retinitis pigmentosa pathogenesis. ARVO Annual Meeting Abstract. Investigative Ophthalmology & Visual Science. Jul. 2019; 60(9): 4925.
Puranik et al., RPGR (Retinitis Pigmentosa GTPase Regulator) isoform expression is modulated by miRNAs involved in cilia regulation. ARVO Annual Meeting Abstract. Investigative Ophthalmology & Visual Science. Jun. 2020; 61(7): 1271.

* cited by examiner

*Primary Examiner* — Amy Rose Hudson
(74) *Attorney, Agent, or Firm* — Wolf, Greenfield & Sacks, P.C.

(57) ABSTRACT

Aspects of the disclosure relate to compositions and methods for modulating expression of certain RPGR retinitis pigmentosa GTPase regulator (RPGR) proteins in a cell or subject. In some embodiments the disclosure provides expression vectors encoding one or more RPGR proteins and/or one or more inhibitory nucleic acids that target certain isoforms of RPGR, for example RPGRCONST. In some aspects, the disclosure relates to methods of treating retinitis pigmentosa (RP) in a subject by administering compositions that modulate RPGR expression or activity.

17 Claims, 37 Drawing Sheets

Specification includes a Sequence Listing.

*RPGR CONST and RPGR ORF15 are shown left to right respectively
for Mean Ctl, Mean RPGR-1, and Mean RPGR-3.

_RNA expression_

*RPGR CONST and RPGR ORF14 are shown left to right respectively for CS7 and RPGR ORF14/KO.

_Protein expression_

| Name | Duplex sequence | Targeted exon |
|---|---|---|
| dsi-NC-SCR | CUUCCUCUCUUUCUCUCCUUGUGA | NA |
| | ACGAGGAGAAGAGAGAGGGAACACU | |
| CD.Ri.215151.13.1 (siRNA.1) | CACCAAGCAAAGACAUGAAAAAAC | 18 |
| | UUGUGGUUCGUUUCUGUACUUUUUUG | |
| CD.Ri.215151.13.2 (siRNA.1) | GGAGCAGAAAGAACCAAUGAUGAUA | 16 |
| | UUCCUCGUCUUUCUUGGUUACUACUAU | |
| CD.Ri.215151.13.3 (siRNA.1) | AUCAAAAGAUUGUCAGAGAUAACAA | 19 |
| | UUUAGUUUUCUAACAGUUCUUAUUGUU | |

(SEQ ID NOS: 1-8 from top to bottom)

| Name | Mature sequence | RPGR target |
|---|---|---|
| miR26a-5p | TTCAAGTAATCCAGGATAGGCT | RPGRCONST |
| miR129.1-3p | AAGCCCTTACCCCAAAAAGTAT | RPGRORF15 |

(SEQ ID NOS: 13-14 from top to bottom)

| Name | Sequence |
|------|----------|
| TuD-129 | 5'- CATCAAC AACATACTTTTTGGGATCT GTAAGGGCTTCAAG GTATATTCTGGTCACAGAATACAACATACTTTTTGGGATCT GTAAGGGCTTCAAG CAAG -3' |
| TuD-26a | 5'- CATCAAC AGCCTATCCTGGATCT CCAGGATAGGCTCAAG GTATATTCTGGTCACAGAATAG AACAGCCTATCCTGGATCT CCAGGATAGGCTT CAAG -3' |

(SEQ ID NOS:35 (top) and 36 (bottom))

[Highlighted]: Stem

[Highlighted]: Stem loop

ATCT: Bulge sequence

[Letters]: miRNA binding site (Forward and reverse)

Triplet: Linker

FIG. 7D

| miRNA backbone | Targeted exon | Targeted sequence | Off-Targets | Primer sequence |
|---|---|---|---|---|
| amiR-RPGR_Ex19 | 19 | TCGGCATCTTTATTATCACTT | 0 | UGCUGUCGGCAUCUUUAUUAUCACUUGUUUUGGCCACUGAC / UGACAAGUCAUAAAAGAUGCCGACAGGA |
| amiR-RPGR_Ex16 | 16 | TCCCACAGTTTTCTTCTTGCT | 0 | UGCUGUCCCACAGUUUAUUCUUGCUGUUUUGGCCACUGAC / UGACAGCAAGAAAACUGUGGGACAGGA |

(SEQ ID NOS: 9 (top left), 10 (top right), 11 (bottom left), and 12 (bottom right))

FIG. 8A

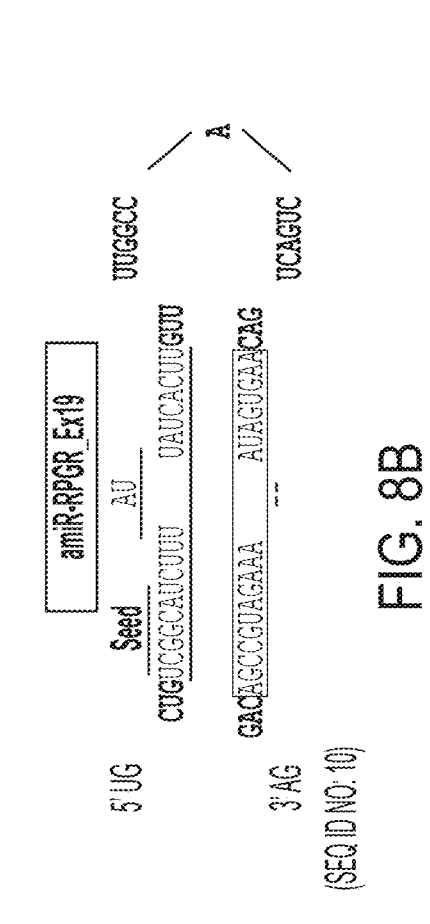

FIG. 8B amiR-RPGR_Ex19

5' UG          Seed    AU

CUGUCCCACAGUUU  UUCUUGCUGUU          UUGGCC

GACAGGGUGUCAAA  AAGAAGACAG

3' AG          --                             UCAGUC
                                                   A hRPGR 1-19
2448 bp

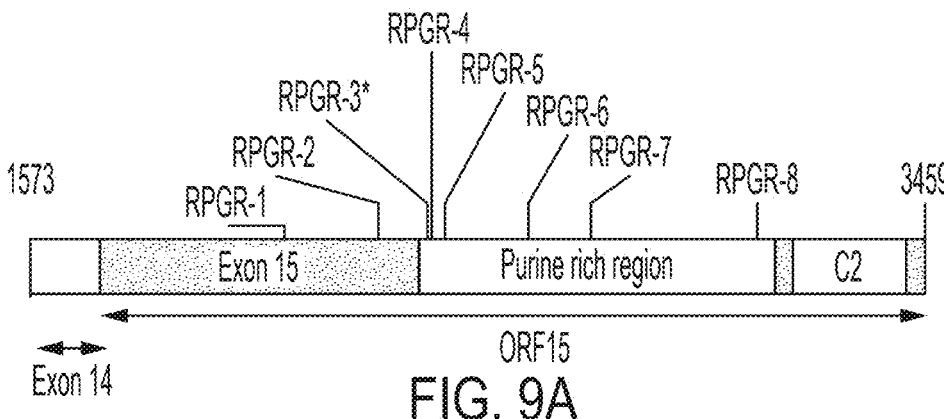
FIG. 9A
| Patient Code | Name | cDNA mutation | Predicted stop codon |
|---|---|---|---|
| 0563 | RPGR-1 | c.2105_2213dup109 | p.E742Gfs*64 |
| 4022 | RPGR-2 | c.2296_2299del GGAG | p.G766Nfs*48 |
| 5798 | RPGR-3 | c.2405_24067delAG | p.E802Gfs*32 |
| 5802 | RPGR-4 | c.2412_2418del7 | p.G805Kfs*8 |
| 1338 | RPGR-5 | c.2442_2445delAGAG | p.G817Kfs*2 |
| 1330 | RPGR-6 | c.2614 G>T | p.E872* |
| 4584 | RPGR-7 | c.2743 G>T | p.G915* |
| 1533 | RPGR-8 | c.3092delA | p.E1031Gfs*58 |
FIG. 9B
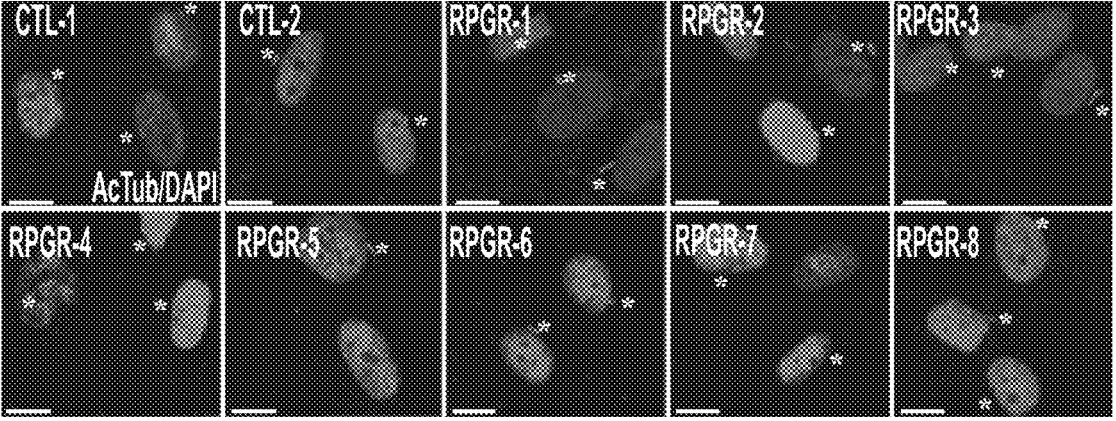
FIG. 10A

*GT335 data is shown as dark grey. Arl13b data is shown as light grey.

FIG. 14A                    FIG. 14B

Messenger RNA half-life

|  | CTL | RPGR-1 | RPGR-2 | RPGR-3 | RPGR-4 | RPGR-5 |
|---|---|---|---|---|---|---|
| RPGR$^{ex1-19}$ | 1.8h | 1.8h | 2.2h | 1.9h | 1.49h | 2.2h |
| RPGR$^{ORF15}$ | 1.6h | 2.3h | 2.2h | 0.67h | 0.51h | 0.28h |

Linear regression ($R^2$)

|  | CTL | RPGR-1 | RPGR-2 | RPGR-3 | RPGR-4 | RPGR-5 |
|---|---|---|---|---|---|---|
| RPGR$^{ex1-19}$ | 0.968 | 0.8839 | 0.9176 | 0.8843 | 0.8405 | 0.8275 |
| RPGR$^{ORF15}$ | 0.8418 | 0.9025 | 0.9066 | 0.5686 | 0.5464 | 0.4315 |

COMPOSITIONS AND METHODS FOR MODULATING RPGR EXPRESSION

CROSS-REFERENCE TO RELATED APPLICATIONS

This application is a national stage filing under 35 U.S.C. § 371 of international PCT application PCT/US2021/020875, filed Mar. 4, 2021, which claims priority under 35 U.S.C. § 119(e) to U.S. provisional patent application, U.S. Ser. No. 62/985,286, filed Mar. 4, 2020, and U.S. Provisional Application Ser. No. 62/984,851, filed Mar. 4, 2020, the entire contents of each of which are incorporated by reference herein.

STATEMENT REGARDING FEDERALLY SPONSORED RESEARCH OR DEVELOPMENT

This invention was made with government support under EY022372 awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Sep. 2, 2022, is named U012070137US02-SEQ-KZM and is 37,567 bytes in size.

BACKGROUND

Mutations in retinitis pigmentosa GTPase regulator (RPGR) are the most frequent cause of X-linked Retinitis Pigmentosa (RP). The RPGR gene is alternatively spliced and has two isoforms: RPGR$^{ORF15}$ (which terminates in intron 15) and RPGR$^{CONST}$ (as may also be referred to herein as RPGR$^{ex1-19}$), which has 19 exons. Currently, clinical trials for gene augmentation of RPGR$^{ORF15}$ are being conducted. The role of RPGR$^{CONST}$ in the maintenance of vision is unclear.

SUMMARY

Aspects of the disclosure relate to compositions and methods for modulating expression of RPGR retinitis pigmentosa GTPase regulator (RPGR) isoforms in a cell or subject. The disclosure is based, in part, on expression constructs encoding one or more inhibitory nucleic acids that target (e.g., specifically bind to) and inhibit expression of certain RPGR isoforms (e.g., RPGR$^{ORF15}$, RPGR-CONST, etc.). In some embodiments, isolated nucleic acids described by the disclosure (e.g., inhibitory nucleic acids targeting RPGR isoforms) are useful for identifying and/or treating diseases associated with aberrant cilial length (e.g., retinitis pigmentosa (RP), X-linked rod-cone dystrophy, certain hearing disorders, etc.) in a subject in need thereof.

In some aspects, the disclosure provides an isolated nucleic acid comprising an expression cassette comprises a first region that encodes an inhibitory nucleic acid that specifically binds to a nucleic acid sequence encoding a RPGR$^{CONST}$ protein.

In some aspects, the disclosure provides an isolated nucleic acid comprising an expression construct that comprises an inhibitory nucleic acid that comprises the sequence set forth in any one of SEQ ID NO: 1-8, 10, and 13 and specifically binds to a nucleic acid sequence encoding a RPGR$^{ORF15}$ protein.

In some embodiments, an inhibitory nucleic acid is a dsRNA, siRNA, shRNA, miRNA, artificial miRNA (amiRNA), or antisense oligonucleotide (ASO).

In some embodiments, an inhibitory nucleic acid does not bind to a nucleic acid sequence encoding RPGR$^{ORF15}$. In some embodiments, an inhibitory nucleic acid comprises the sequence set forth in SEQ ID NO: 11 or 14.

In some embodiments, the inhibitory nucleic acid does not bind to a nucleic acid sequence encoding RPGRCONST.

In some embodiments, an inhibitory nucleic acid is an amiRNA. In some embodiments, an amiRNA comprises a miRNA backbone selected from: miR-168, miR-157, miR-155, and miR-30 backbone.

In some embodiments, a first region further comprises a first promoter operably linked to a sequence encoding an inhibitory nucleic acid. In some embodiments, a first promoter is a constitutive promoter, inducible promoter, or tissue-specific promoter. In some embodiments, a first promoter is a RNA polymerase III (pol III) promoter. In some embodiments, a pol III promoter is a U6 promoter or H1 promoter.

In some embodiments, an expression cassette further comprises a second region encoding a RPGR$^{ORF15}$ protein. In some embodiments, an RPGR$^{ORF15}$ protein comprises the amino acid sequence set forth in SEQ ID NO: 15. In some embodiments, an RPGR$^{ORF15}$ protein is encoded by the nucleic acid sequence set forth in SEQ ID NO: 16. In some embodiments, an RPGR$^{ORF15}$ protein comprises the amino acid sequence set forth in SEQ ID NO: 17. In some embodiments, an RPGR$^{ORF15}$ protein is encoded by the nucleic acid sequence set forth in SEQ ID NO: 18. In some embodiments, a second region comprises a second promoter operably linked to the sequence encoding the RPGR$^{ORF15}$ protein. In some embodiments, a second promoter is a constitutive promoter, inducible promoter, or tissue-specific promoter. In some embodiments, a second promoter is a RNA polymerase II (pol II) promoter.

In some embodiments, an expression cassette is flanked by adeno associated virus (AAV) inverted terminal repeats (ITRs).

In some aspects, the disclosure provides a plasmid comprising an isolated nucleic acid as described herein. In some aspects, the disclosure provides a host cell comprising an isolated nucleic acid as described herein. In some embodiments, a host cell is a mammalian cell, bacterial cell, yeast cell, or insect cell.

In some aspects, the disclosure provides a recombinant adeno-associated virus (rAAV) comprising: an isolated nucleic acid as described herein; and at least one AAV capsid protein.

In some embodiments, a capsid protein is of a serotype selected from AAV1, AAV2, AAV3, AAV4, AAV5, AAV6, AAV7, AAV8, AAV9, and AAVrh.10.

In some aspects, the disclosure provides a composition comprising an isolated nucleic acid or rAAV as described herein, and a pharmaceutically acceptable excipient. In some embodiments, a composition is formulated for intravitreal or subretinal injection.

In some aspects, the disclosure provides a method for decreasing length of cell cilia, the method comprising administering to the cell an isolated nucleic acid as described herein. In some aspects, the disclosure provides a method for increasing length of cell cilia, the method comprising administering to the cell an isolated nucleic acid as described herein.

In some embodiments, a cell is an ocular cell. In some embodiments, a cell is in a subject. In some embodiments, a cell is in a human subject.

In some aspects, the disclosure provides a method for treating a disease associated with aberrant cilial length, the method comprising administering to a subject characterized by aberrant cilial length an isolated nucleic acid or the rAAV as described herein. In some embodiments, a subject is a human. In some embodiments, a subject has one or more mutations in RPGR gene. In some embodiments, a subject has retinitis pigmentosa (RP) or X-linked cone-rod dystrophy. In some embodiments, RP is X-linked RP.

In some embodiments, the isolated nucleic acid or rAAV is administered to the eye of the subject. In some embodiments, administration to the eye is topical administration, intravitreal injection, or subretinal injection.

In some embodiments, a subject has been or is concurrently administered an isolated nucleic acid encoding a $RPGR^{ORF15}$ protein.

In some aspects, the disclosure provides a method for selecting a therapeutic regimen for a subject, the method comprising: determining an expression level of a $RPGR^{ORF15}$ in a biological sample obtained from a subject; determining an expression level of a $RPGR^{CONST}$ in the biological sample; calculating a $RPGR^{ORF15}$:$RPGR^{CONST}$ ratio based upon the expression levels; and, administering to the subject an isolated nucleic acid as described herein if the ratio of $RPGR^{ORF15}$:$RPGR^{CONST}$ is greater than between about 1:0.5 to about 1:7.

In some aspects, the disclosure relates to an isolated inhibitory nucleic acid comprising a binding site for a microRNA (miRNA) which binds an RPGR messenger RNA (mRNA). In some embodiments, an isolated inhibitory nucleic acid comprises a Tough Decoy (TuD). In some embodiments, a TuD comprises a binding site for an miRNA that binds $RPGR^{CONST}$. In some embodiments, a TuD comprises a binding site for an miRNA that binds $RPGR^{ORF15}$. In some embodiments, a TuD comprises a binding site for miR-168, miR-157, miR-155, miR-30, miR-129, and/or miR-26a. In some embodiments, a TuD comprises a binding site for miR-129. In some embodiments, a TuD comprises SEQ ID NO: 35. In some embodiments, a TuD comprises a binding site for miR-26a. In some embodiments, a TuD comprises SEQ ID NO: 36.

In some aspects, the disclosure relates to a method of modulating RPGR expression in a cell or subject, the method comprising administering at least one of the TuDs of the disclosure to the cell or subject. In some embodiments, administering a TuD results in a change in cilial length of the cell or the cells of the subject.

In some aspects, the disclosure relates to a recombinant adeno-associated virus (rAAV) comprising a transgene comprising a nucleic acid sequence encoding at least one TuD of the disclosure. In some embodiments, an rAAV comprises an AAV8 capsid protein. In some embodiments, an rAAV a transgene further comprises a promoter operably linked to the nucleic acid sequence encoding the TuD.

Each of the limitations of the disclosure can encompass various embodiments of the invention. It is, therefore, anticipated that each of the features of the invention involving any one feature or combinations of features can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

Further aspects of the disclosure will be readily appreciated upon review of the Detailed Description of its various aspects and embodiments, described below, when taken in conjunction with the accompanying Drawings.

FIG. 1C shows a schematic localization of $RPGR^{ORF15}$ mutation in patient primary fibroblasts and patient-derived organoids. *p<0.05%, **p<0.01. WT: wild type control. Columns from left to right (columns 1-7) in $RPGR^{CONST}$: Mean WT; 5798; 1338; 5802; 1330; 4584; and 1533. Columns from left to right (columns 8-14) in $RPGR^{ORF15}$: Mean WT; 5798; 1338; 5802; 1330; 4584; and 1533. FIG. 1C shows the location of $RPGR^{ORF15}$ mutations in patient primary fibroblasts and patient-derived organoids. *p<0.05, *p<0.01.

FIG. 3A: Columns from left to right in C57 (columns 1-2 overall): RPGR CONST; and RPGR ORF14. Columns from left to right in $RPGR^{ORF14/KO}$ (columns 3-4 overall): $RPGR^{CONST}$; and RPGR ORF14.

6A) and RPGR$^{CONST}$ (FIG. 6B) targeted sequences designed. FIG. 6A shows SEQ ID NO: 1-8 from top to bottom. FIG. 6B: Left Panel—Columns from left to right (columns 1-4) in SL: SCR; siRNA.1; siRNA.2; and siRNA.3. Columns from left to right (columns 5-8) in SJ: SCR; siRNA.1; siRNA.2; and siRNA.3. Columns from left to right (columns 9-12) in 5798: SCR; siRNA.1; siRNA.2; and siRNA.3. Columns from left to right (columns 13-16) in 5802: SCR; siRNA.1; siRNA.2; and siRNA.3. Right Panel—Columns from left to right (columns 1-4) in SL: SCR; siRNA.1; siRNA.2; and siRNA.3. Columns from left to right (columns 5-8) in SJ: SCR; siRNA.1; siRNA.2; and siRNA.3. Columns from left to right (columns 9-12) in 5798: SCR; siRNA.1; siRNA.2; and siRNA.3. Columns from left to right (columns 13-16) in 5802: SCR; siRNA.1; siRNA.2; and siRNA.3. RPGR isoforms expression was measured by RT-qPCR and shows efficient RPGR$^{CONST}$ knockdown in patient fibroblasts with no significant effect on RPGR$^{ORF15}$ levels (FIG. 6C). Cilia length were measured as previously described. Knockdown of RPGR1-19 expression shows significant rescue in cilia length defects for RPGR$^{ORF15}$ patient fibroblasts with high RPGR$^{CONST}$ levels (FIG. 6D). *p<0.05%, **p<0.01.

FIGS. 7A-7E show targeting RPGR isoforms using miR-NAs. miRNA sequences and corresponding RPGR isoform targets (FIG. 7A). FIG. 7A shows SEQ ID NO: 13-14 from top to bottom. RPGR$^{CONST}$ and RPGR$^{ORF15}$ levels were analyzed by qPCR after miRNAs overexpression (FIG. 7B). Cilia length were measured as previously described. miR26a-5p targeting RPGR$^{CONST}$ decrease cilia length and miR129-3p targeting RPGR$^{ORF15}$ increase cilia length in RPE cell lines (FIG. 7C). *p<0.05%, **p<0.01. Best predicted primers sequences were used to design artificial miRNAs targeting RPGR$^{CONST}$. FIG. 7D shows tough-decoy (TuD) RNA inhibitor sequences. FIG. 7E shows TuD RNA inhibitors of FIG. 7D are efficient anti-miRNA molecules that are used to assess the effect of knocking down the miRNAs of interest.

FIGS. 8A-8D show data relating to targeting RPGR isoforms using artificial miRNAs. FIG. 8A shows artificial miRNAs sequences based on has-miR155 backbone and targeting RPGR$^{CONST}$ isoform (SEQ ID NO: 9-12). Nucleotides shaded in top strand represent the amiRNA leader sequence complementary to RPGR$^{CONST}$. Nucleotides in bold corresponds to the 2nt-bulge. Nucleotides shaded on bottom strand represent the amiRNA passenger sequence complementary to the leader sequence. FIGS. 8B and 8C show the secondary structure of the pre-artificial miRNAs (SEQ ID NO: 10 and 12 respectively). FIG. 8D shows a schematic localization of the amiRNAs targeting sequences.

FIGS. 9A-9B show RPGR$^{ORF15}$ mutations. Schematic representation (FIG. 9A) and predicted effect of RPGR$^{ORF15}$ mutations (FIG. 9B) in XLRP patients. *: optic cups of RPGR-3 were generated.

FIGS. 10A-10B show ciliary defects in fibroblasts. FIG. 10A shows control (CTL-1 and CTL-2) and mutant fibroblasts were stained for acetylated-α-tubulin (marked with asterisks; ciliary marker) and DAPI (nucleus). Scale: 5 μm. FIG. 10B shows the cilia length was quantified using the Image-J software (n>100). The CTL data represents the average cilia length of all control fibroblasts. **: p<0.0001; *: p<0.002; **: p<0.01; *: p<0.05.

FIGS. 11A-11B show RPGR$^{ex1-19}$ (FIG. 11A) or RPGR$^{ORF15}$ levels in the mutant fibroblasts relative to controls (CTL) were analyzed. FIG. 11C shows the ratio of RPGR$^{ex1-19}$ to RPGR$^{ORF15}$ mRNA levels was determined. RPGR-1, RPGR-3, RPGRC-4 and RPGNR-5 FshowIedDsignEificanNtly higTher rIatAio whLen compared to control (CTL) cells. ns: not significant. Data are mean±SD from five independent experiments. FIG. 11D shows positive correlation of the cilium length with the RPGR$^{ex1-19}$/RPGR$^{ORF15}$ ratio was observed. Each dot represents average cilium length of >100 cilia compared to the RPGR$^{ex1-19}$/RPGR$^{ORF15}$ ratio from three independent experiments. Black line shows a linear fit through the data. Inset displays the coefficient of determination (R2) and significance (p value).

FIG. 12A shows the cells were stained with CEP290 and α-tubulin (basal body marker; white circles) antibodies and the ratio of the CEP290-positive signal in the cytoplasm to that at the basal body (FIG. 12B) and the number of CEP290-positive cells (FIG. 12C) were quantified using ImageJ. n>100. FIG. 12D shows the cells were stained with GT335 glutamylated tubulin) and ARL13B (indicated by arrow; cilia marker). FIG. 12E shows the distribution of GT335 signal intensity) along the length of the cilium when compared to ARL13B (dots intensity) (Distance; μm) was quantified using IMARIS software (Oxford Instruments). a.u.: arbitrary units.

FIG. 13A shows the fibroblasts were transiently transfected with plasmids encoding GFP or GFP-RPGR$^{ORF15}$ and processed for staining with the GFP (bottom left square) or acetylated α-tubulin (marked with a white circle; ciliary marker). Arrows point to the ciliated cells marked in the inset in green channel. The nuclei are stained with DAPI (grey oval shaped spots). FIG. 13B shows the cilia length was quantified using Image J (n>100). The graph shows the cilia length relative to the length of the control (CTL) fibroblasts transfected with only GFP-encoding cDNA. The statistical significance of the cilia length in the GFP or GFP-RPGR$^{ORF15}$-transfected mutant fibroblasts cells was determined relative to the GFP-transfected control fibroblasts. : p<0.01; * p<0.0002; **** p<0.0001; ns: not significant. Note that the GFP-RP-GR$^{ORF15}$-transfected RPGR-2 and CTL cells have significantly shorter cilia when compared to the GFP-transfected counterparts.

FIGS. 14A-14C show the mutant mRNA decay in RPGR$^{ORF15}$-fibroblasts: qPCR analysis of RPGR$^{ORF15}$ (FIG. 14A) or RPGR$^{ex1-19}$ (FIG. 14B) isoform was performed in fibroblasts treated with actinomycin-D for indicated time. The levels of the mutant isoforms were calculated relative to the levels in the control (CTL) fibroblasts at the same time points. Statistical significance was determined by assessing the mRNA levels at each time-point relative to that of the control (CTL) at the same time-point. **: p<0.0001; : p<0.01; *: p<0.05. No significant changes in the degradation of RPGRex-19 mRNA was detected at the Human Molecular Genetics Page 28 of 63 same time-points (FIG. 14B). FIG. 14C shows the half-life and linear regression of the mutant RPGR$^{ORF15}$ and RPGR$^{ex1-19}$ mRNAs was calculated by determining the time (in hours) taken by the isoforms to reduce to half the original levels.

FIG. 15A shows the fibroblasts were transiently transfected with RPGR-siRNA-3 or scrambled siRNA followed by GFP (bottom right corner; inset) and acetylated α-tubulin staining. FIG. 15B shows the cilia length was quantified represented as the length relative to the scrambled siRNA-treated control (CTL) cells. Scale: 5 μm. ns: not significant

FIG. 18B shows RPGR$^{ORF15}$-overexpression did not affect RPGR$^{ex1-19}$ mRNA levels in fibroblasts.

FIG. 20A shows AAV8-encoding miR-26a-5p was sub-retinally injected into wild type mice at post natal day P10. The effect on light response of the photoreceptors was analyzed by electroretinography (ERG) at indicated weeks post injection. The decline in the light-responsive a-wave (longer arrows) and b-wave (shorter arrows) is indicated. FIG. 20B shows quantification of the amplitudes in both scotopic (dark-adapted) and light-adapted (photopic) conditions shows significant decline in the light response with age. FIG. 20C shows AAV8-encoding miR-129.1-3p was sub-retinally injected into wild type mice at post-natal day P10. The effect on light response of the photoreceptors was analyzed by electroretinography (ERG) at indicated weeks post injection. The decline in the light-responsive a-wave (longer arrows) and b-wave (shorter arrows) is indicated. FIG. 20D shows quantification of the amplitudes in both scotopic (dark-adapted) and light-adapted (photopic) conditions shows significant decline in the light response with age. FIG. 20E shows AAV8-encoding EGFP (Control; CTL (top row) or miR129.1-3p with GFP (bottom row)) were sub-retinally injected into mouse retina. Four (4) weeks post-injection, the mice were imaged by funduscopy to identify the transduced region (arrows). The areas marked by horizontal lines were subsequently analyzed by optical coherence tomography (OCT). The OCT image shows the different retinal layers as marked. The areas transduced with GFP-control or the untransduced areas of the same retinas did not show detectable differences in the different retinal layer thickness. However, there was significant thinning of the outer nuclear layer (ONL), which represents the photoreceptor nuclei in the miR-129-transduced regions versus the untransduced regions. RPE: retinal pigment epithelium; OS: outer segment; IS: inner segment; OPL: outer plexiform layer; INL: inner nuclear layer; GCL: ganglion cell layer.

DETAILED DESCRIPTION

Figure 1A:
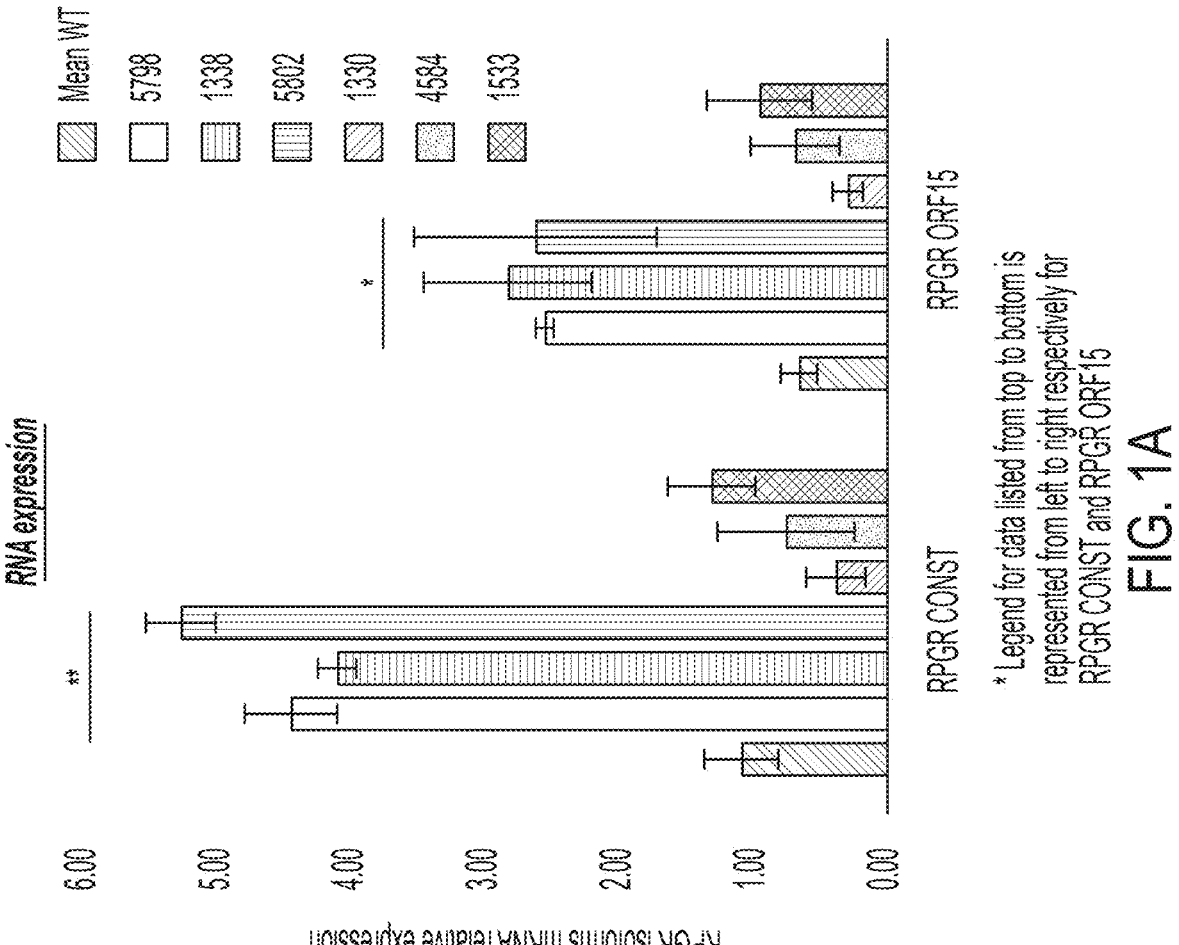
FIGS. 1A-1C show specific mutations in intron 15 increase $RPGR^{CONST}$ levels in patient fibroblasts. $RPGR^{CONST}$ and $RPGR^{ORF15}$ levels were analyzed for transcript and protein expression by qPCR (FIG. 1A) and western blot (FIG. 1B).

The disclosure relates, in some aspects, to compositions and methods for modulating expression of RPGR retinitis pigmentosa GTPase regulator (RPGR) isoforms in a cell or subject. In some embodiments, the disclosure provides expression constructs encoding one or more inhibitory nucleic acids that target (e.g., specifically bind to) and inhibit expression of certain RPGR isoforms (e.g., RPGR$^{ORF15}$, RpGR$^{CONST}$, etc.).

Retinitis Pigmentosa GTPase Regulator (RPGR)

Aspects of the disclosure relate to isolated nucleic acids that encode one or more inhibitory nucleic acids that specifically bind to a nucleic acid sequence encoding a RPGR protein isoform (e.g., RPGR$^{CONST}$, RPGR$^{ORF15}$, etc.). In humans, RPGR protein isoforms are encoded by the RPGR gene. In some embodiments, the RPGR gene comprises the nucleic acid sequence set forth in any one of NCBI Accession Numbers: NM_000328.3, NM_001034853.2, NM_001367245.1, NM_001367246.1, NM_001367247.1, NM_001367248.1, NM_001367249.1, NM_001367250.1, NM_001367251.1, NR_159803.1, NR_159804.1, NR_159805.1, NR_159806.1, NR_159807.1, and NR_159808.1.

RPGR protein plays an important role in cilial formation and elongation. Several different isoforms of the RPGR protein are produced from the RPGR gene. One isoform contains a portion known as the $^{ORF15}$ exon. This version of the RPGR protein (referred to as RPGR$^{ORF15}$) is expressed predominantly in retinal cells, for example photoreceptor cells. Other isoforms of the RPGR protein are expressed in different cell types, for example respiratory endothelial cells, olfactory neurons, hair cells (e.g., stereocilia), etc.

In some embodiments, the disclosure relates to isolated nucleic acids encoding a RPGR$^{ORF15}$ protein. In some embodiments, an RPGR$^{ORF15}$ protein comprises the amino acid sequence set forth in SEQ ID NO: 15. In some embodiments, an RPGR$^{ORF15}$ protein is encoded by the nucleic acid sequence set forth in SEQ ID NO: 16. In some embodiments, RPGR$^{ORF15}$ protein comprises an amino acid sequence having at least 70% sequence identity (e.g., 70%, 80%, 81%, 82%, 83%, 84%, 85%, 86%, 87%, 88%, 89%, 90%, 91%, 92%, 93%, 94%, 95%, 96%, 97%, 98%, 99%, or more) to the sequence set forth in SEQ ID NO: 15. In some embodiments, RPGR$^{ORF15}$ protein is encoded by a nucleic acid sequence having at least 70% sequence identity (e.g., 70%, 80%, 81%, 82%, 83%, 84%, 85%, 86%, 87%, 88%, 89%, 90%, 91%, 92%, 93%, 94%, 95%, 96%, 97%, 98%, 99%, or more) to the sequence set forth in SEQ ID NO: 16. In some embodiments, an RPGR$^{ORF15}$ protein comprises the amino acid sequence set forth in SEQ ID NO: 17. In some embodiments, an RPGR$^{ORF15}$ protein is encoded by the nucleic acid sequence set forth in SEQ ID NO: 18. In some embodiments, RPGR$^{ORF15}$ protein comprises an amino acid sequence having at least 70% sequence identity (e.g., 70%, 80%, 81%, 82%, 83%, 84%, 85%, 86%, 87%, 88%, 89%, 90%, 91%, 92%, 93%, 94%, 95%, 96%, 97%, 98%, 99%, or more) to the sequence set forth in SEQ ID NO: 17. In some embodiments, RPGR$^{ORF15}$ protein is encoded by a nucleic acid sequence having at least 70% sequence identity (e.g., 70%, 80%, 81%, 82%, 83%, 84%, 85%, 86%, 87%, 88%, 89%, 90%, 91%, 92%, 93%, 94%, 95%, 96%, 97%, 98%, 99%, or more) to the sequence set forth in SEQ ID NO: 18.

The terms "percent identity," "sequence identity," "% identity," "% sequence identity," and "% identical," as they may be interchangeably used herein, refer to a quantitative measurement of the similarity between two sequences (e.g., nucleic acid or amino acid). The percent identity of genomic DNA sequence, intron and exon sequence, and amino acid sequence between humans and other species varies by species type, with chimpanzee having the highest percent identity with humans of all species in each category.

Calculation of the percent identity of two nucleic acid sequences, for example, can be performed by aligning the two sequences for optimal comparison purposes (e.g., gaps can be introduced in one or both of a first and second nucleic acid sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences.

The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., Nucleic Acids Research, 12(1), 387 (1984)), BLASTP, BLASTN, and FASTA Atschul, S. F. et al., J. Molec. Biol., 215, 403 (1990)).

When a percent identity is stated, or a range thereof (e.g., at least, more than, etc.), unless otherwise specified, the endpoints shall be inclusive and the range (e.g., at least 70% identity) shall include all ranges within the cited range (e.g., at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.5%, at least 99.6%, at least 99.7%, at least 99.8%, at least 99.9% identity) and all increments thereof (e.g., tenths of a percent (e.g., 0.1%), hundredths of a percent (e.g., 0.01%), etc.).

Isolated Nucleic Acids

The disclosure relates, in some aspects, to isolated nucleic acids encoding one or more inhibitory nucleic acids (e.g., transgenes). As used herein, the term "nucleic acid," refers to a polymer of nucleotides. The term includes, but is not limited to, oligonucleotides and polynucleotides, both single-stranded and double-stranded forms, including hybrids, for example, of DNA and RNA strands, or of strands comprising ribonucleotides, deoxyribonucleotides, and/or modified nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5 bromouridine, C5 fluorouridine, C5 iodouridine, C5 propynyl uridine, C5 propynyl cytidine, C5 methylcytidine, 7 deazaadenosine, 7 deazaguanosine, 8 oxoadenosine, 8 oxoguanosine, O(6) methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5' N phosphoramidite linkages).

The nucleic acids may also comprise modifications. The term "nucleic acid modifications," as used herein, refers to modifications made to an oligonucleotide, or the constituent portions or linkages thereof (i.e., the nitrogenous base, sugar, or phosphate group). Modifications may be introduced for a variety of reasons, often to increase stability, reduce off-target effects, increase hybridization (i.e., binding) properties, or to reduce toxicity.

Purine and/or pyrimidine nucleobases may be modified, for example by amination or deamination of the heterocyclic rings. Further, modified sugars, such as a 2'-O-methoxyethyl sugar, a 2'-fluoro sugar modification, a 2'-O-methyl sugar, a bicyclic sugar moiety, or substitutions such as a 2'-O moiety with a lower alkyl, an alkenyl, an alkynyl, a methoxyethyl (2'-O-MOE), an —H (as in DNA), or other substituent may be introduced. Other examples may include the addition of a conjugate linked to the oligonucleotide, such as a cholesterol or phosphorothioate, to render the molecule more resistant to degradation.

Other chemistries and modification are known in the field of oligonucleotides that can be readily used in accordance with the disclosure and are encompassed within the definition of a nucleic acid modification. Linkages between the nucleotides may be modified by means of thioation of the phosphodiester bonds which can be used to yield phosphorothioate esters or phosphorodithioate esters. Further modification to the linkages include amidation and peptide linkers.

The term "expression construct," as used herein, refers to a nucleic acid construct comprising nucleic elements sufficient for the expression of a gene product. Typically, an expression construct comprises a nucleic acid encoding a gene product (e.g., transgene) operatively linked to a promoter sequence. The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (e.g., the coding sequence is under the transcriptional control of the promoter). Encoding sequences can be operatively linked to regulatory sequences in sense or antisense orientation. In some embodiments, the promoter is a heterologous promoter.

In some embodiments, isolated nucleic acids described herein comprise one or more of the following structural features (e.g., control or regulatory sequences): a promoter, an intron, a Kozak sequence, a nucleic acid sequence encoding one or more inhibitory nucleic acids (e.g., an inhibitory nucleic acid specifically targeting a RPGR protein isoform, e.g., transgene), one or more miRNA binding sites, and a rabbit beta-globulin (RBG) poly A sequence. In some embodiments, one or more of the foregoing control sequences is operably linked to the nucleic acid sequence encoding the one or more inhibitory nucleic acids.

A "promoter" refers to a DNA sequence recognized by the synthetic machinery of the cell, or introduced synthetic machinery, required to initiate the specific transcription of a gene. The phrases "operatively linked," "operatively positioned," "under control" or "under transcriptional control" means that the promoter is in the correct location and orientation in relation to the nucleic acid to control RNA polymerase initiation and expression of the gene. Generally, a promoter can be a constitutive promoter, inducible promoter, or a tissue-specific promoter.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al., Cell, 41:521-530 (1985)], the SV40 promoter, the dihydrofolate reductase promoter, the β-actin promoter, the phosphoglycerol kinase (PGK) promoter, and the EF1α promoter [Invitrogen]. In some embodiments, a promoter is an RNA pol II promoter. In some embodiments, a promoter is an RNA pol III promoter, such as U6 or H1. In some embodiments, a promoter is an RNA pol II promoter.

Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system (WO 98/10088); the ecdysone insect promoter (No et al., Proc. Natl. Acad. Sci. USA, 93:3346-3351 (1996)), the tetracycline-repressible system (Gossen et al., Proc. Natl. Acad. Sci. USA, 89:5547-5551 (1992)), the tetracycline-inducible system (Gossen et al., Science, 268:1766-1769 (1995), see also Harvey et al., Curr. Opin. Chem. Biol., 2:512-518 (1998)), the RU486-inducible system (Wang et al., Nat. Biotech., 15:239-243 (1997) and Wang et al., Gene Ther., 4:432-441 (1997)) and the rapamycin-inducible system (Magari et al., J. Clin. Invest., 100:2865-2872 (1997)). Still other types of inducible promoters which may be useful in this context are those which are regulated by a specific physiological state, e.g., temperature, acute phase, a particular differentiation state of the cell, or in replicating cells only.

In some embodiments, the native promoter for the transgene (e.g., RPGR) will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In some embodiments, the regulatory sequences impart tissue-specific gene expression capabilities. In some cases, the tissue-specific regulatory sequences bind tissue-specific transcription factors that induce transcription in a tissue specific manner. Such tissue-specific regulatory sequences (e.g., promoters, enhancers, etc.) are well known in the art. Exemplary tissue-specific regulatory sequences include, but are not limited to the following tissue specific promoters: retinoschisin proximal promoter, interphotoreceptor retinoid-binding protein enhancer (RS/IRBPa), rhodopsin kinase (RK), liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a α-myosin heavy chain (α-MHC) promoter, or a cardiac Troponin T (cTnT) promoter. Other exemplary promoters include Beta-actin promoter, hepatitis B virus core promoter, Sandig et al., Gene Ther., 3:1002-9 (1996); alpha-fetoprotein (AFP) promoter, Arbuthnot et al., Hum. Gene Ther., 7:1503-14 (1996)), bone osteocalcin promoter (Stein et al., Mol. Biol. Rep., 24:185-96 (1997)); bone sialoprotein promoter (Chen et al., J. Bone Miner. Res., 11:654-64 (1996)), CD2 promoter (Hansal et al., J. Immunol., 161:1063-8 (1998); immunoglobulin heavy chain promoter; T cell receptor α-chain promoter, neuronal such as neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al., Neuron, 15:373-84 (1995)), among others which will be apparent to the skilled artisan.

In some embodiments, the tissue-specific promoter is an eye-specific promoter (e.g., an ocular gene promoter).

Examples of eye-specific promoters include retinoschisin proximal promoter, interphotoreceptor retinoid-binding protein enhancer (RS/IRBPa), rhodopsin kinase (RK), RPE65, and human cone opsin promoter.

In some embodiments, a promoter is a chicken beta-actin (CB) promoter. A chicken beta-actin promoter may be a short chicken beta-actin promoter or a long chicken beta-actin promoter. In some embodiments, a promoter (e.g., a chicken beta-actin promoter) comprises an enhancer sequence, for example a cytomegalovirus (CMV) enhancer sequence. A CMV enhancer sequence may be a short CMV enhancer sequence or a long CMV enhancer sequence. In some embodiments, a promoter comprises a long CMV enhancer sequence and a long chicken beta-actin promoter. In some embodiments, a promoter comprises a short CMV enhancer sequence and a short chicken beta-actin promoter. However, the skilled artisan recognizes that a short CMV enhancer may be used with a long CB promoter, and a long CMV enhancer may be used with a short CB promoter (and vice versa).

An isolated nucleic acid described herein may also contain an intron, desirably located between the promoter/enhancer sequence and the transgene. In some embodiments, an intron is a synthetic or artificial (e.g., heterologous) intron. Examples of synthetic introns include an intron sequence derived from SV-40 (referred to as the SV-40 T intron sequence) and intron sequences derived from chicken beta-actin gene. In some embodiments, a transgene described by the disclosure comprises one or more (1, 2, 3, 4, 5, or more) artificial introns. In some embodiments, the one or more artificial introns are positioned between a promoter and a nucleic acid sequence encoding one or more complement control proteins (e.g., a fusion protein as described herein.

In some embodiments, a transgene comprises a Kozak sequence. A Kozak sequence is a nucleic acid motif comprising a consensus sequence GCC(A/G)CC that is found in eukaryotic mRNA and plays a role in initiation of protein translation.

An isolated nucleic acid described by the disclosure may encode a transgene that further comprises a polyadenylation (poly A) sequence. In some embodiments, a transgene comprises a poly A sequence is a rabbit beta-globulin (RBG) poly A sequence.

In some embodiments, the isolated nucleic acid described herein is a multicistronic expression construct. In some embodiments, multicistronic expression constructs are expression cassettes that are positioned in different ways. For example, in some embodiments, a multicistronic expression construct is provided in which a first expression cassette (e.g., the first expression cassette described herein) is positioned adjacent to a second expression cassette (e.g., the second expression cassette described herein). In some embodiments, a multicistronic expression construct is provided in which a first expression cassette comprises an intron, and a second expression cassette is positioned within the intron of the first expression cassette. In some embodiments, the second expression cassette, positioned within an intron of the first expression cassette, comprises a promoter and a nucleic acid sequence encoding a gene product operatively linked to the promoter.

The term "orientation" as used herein in connection with expression cassettes, refers to the directional characteristic of a given cassette or structure. In some embodiments, an expression cassette harbors a promoter 5' of the encoding nucleic acid sequence, and transcription of the encoding nucleic acid sequence runs from the 5' terminus to the 3' terminus of the sense strand, making it a directional cassette (e.g. 5'-promoter/(intron)/encoding sequence-3'). Since virtually all expression cassettes are directional in this sense, those of skill in the art can easily determine the orientation of a given expression cassette in relation to a second nucleic acid structure, for example, a second expression cassette, a viral genome, or, if the cassette is comprised in an AAV construct, in relation to an AAV ITR.

For example, if a given nucleic acid construct comprises two expression cassettes in the configuration 5'-promoter 1/encoding sequence 1—promoter2/encoding sequence                2-3',                >>>>>>>>>>>>>>>
>>>>>>>>>>>>>>>>>>>>>>>>>>>>>>>>>>>> the expression cassettes are in the same orientation, the arrows indicate the direction of transcription of each of the cassettes. For another example, if a given nucleic acid construct comprises a sense strand comprising two expression cassettes in the configuration 5'-promoter 1/encoding sequence 1—encoding sequence 2/promoter            2-3',            >>>>>>>>>>>>>>>>>
>>>>>>><<<<<<<<<<<<<<<<<<<<< the expression cassettes are in opposite orientation to each other and, as indicated by the arrows, the direction of transcription of the expression cassettes, are opposed. In this example, the strand shown comprises the antisense strand of promoter 2 and encoding sequence 2.

For another example, if an expression cassette is comprised in an AAV construct, the cassette can either be in the same orientation as an AAV ITR, or in opposite orientation. AAV ITRs are directional. For example, the 3' ITR would be in the same orientation as the promoter 1/encoding sequence 1 expression cassette of the examples above, but in opposite orientation to the 5' ITR, if both ITRs and the expression cassette would be on the same nucleic acid strand.

In some embodiments, a multicistronic expression construct is provided that allows efficient expression of a first encoding nucleic acid sequence driven by a first promoter and of a second encoding nucleic acid sequence driven by a second promoter without the use of transcriptional insulator elements. Various configurations of such multicistronic expression constructs are provided herein, for example, expression constructs harboring a first expression cassette comprising an intron and a second expression cassette positioned within the intron, in either the same or opposite orientation as the first cassette. Other configurations are described in more detail elsewhere herein.

In some embodiments, multicistronic expression constructs are provided allowing for efficient expression of two or more encoding nucleic acid sequences. In some embodiments, the multicistronic expression construct comprises two expression cassettes. In some embodiments, a first expression cassette of a multicistronic expression construct as provided herein comprises a first RNA polymerase II promoter and a second expression cassette comprises a second RNA polymerase II promoter. In some embodiments, a first expression cassette of a multicistronic expression construct as provided herein comprises an RNA polymerase II promoter and a second expression cassette comprises an RNA polymerase III promoter.

In some embodiments, first nucleic acid sequence (e.g., encoding a first inhibitory nucleic acid or protein) and a second nucleic acid sequence (e.g., encoding a second inhibitory nucleic acid or protein) are joined by a linking molecule. In some embodiments, a linking molecule is an amino acid linker, for example a glycine-serine rich linker.

In some aspects, the disclosure relates to isolated nucleic acids comprising a transgene encoding one or more inhibitory nucleic acids, and one or more miRNA binding sites. Without wishing to be bound by any particular theory, incorporation of miRNA binding sites into gene expression constructs allows for regulation of transgene expression (e.g., inhibition of transgene expression) in cells and tissues where the corresponding miRNA is expressed. In some embodiments, incorporation of one or more miRNA binding sites into a transgene allows for de-targeting of transgene expression in a cell-type specific manner. In some embodiments, one or more miRNA binding sites are positioned in a 3' untranslated region (3' UTR) of a transgene, for example between the last codon of a nucleic acid sequence encoding one or more complement control proteins as described herein, and a poly A sequence.

In some embodiments, a transgene comprises one or more (e.g., 1, 2, 3, 4, 5, or more) miRNA binding sites that de-target expression of a transgene from liver cells. For example, in some embodiments, a transgene comprises one or more miR-122 binding sites. As used herein, the term "de-target," means to inhibit expression of a transgene or other gene product of interest in the nucleic acid delivered in a subject tissue or cell. For example, without limitation, the term shall mean to minimize or reduce the expression in tissues or cells where activity is not desirous or is detrimental or deleterious. Among other means, this may be accomplished by the integration of miRNA binding sites into the nucleic acid, wherein the miRNA binding sites are sites known to bind miRNA expressed (e.g., tissue specifically expressed or over-expressed as relative to other tissues of interest) in the tissue which is to be "de-targeted."

In some embodiments, a transgene comprises one or more (e.g., 1, 2, 3, 4, 5, or more) miRNA binding sites that de-target expression of a transgene from immune cells (e.g., antigen presenting cells (APCs), such as macrophages, dendrites, etc.). Incorporation of miRNA binding sites for immune-associated miRNAs may de-target transgene (e.g., one or more inhibitory nucleic acids) expression from antigen presenting cells and thus reduce or eliminate immune responses (cellular and/or humoral) produced in the subject against products of the transgene, for example as described in US 2018/0066279, the entire contents of which are incorporated herein by reference.

As used herein an "immune-associated miRNA" is an miRNA preferentially expressed in a cell of the immune system, such as an antigen presenting cell (APC). In some embodiments, an immune-associated miRNA is an miRNA expressed in immune cells that exhibits at least a 2-fold, 3-fold, 4-fold, 5-fold, 6-fold, 7-fold, 8-fold, 9-fold, 10-fold higher level of expression in an immune cell compared with a non-immune cell (e.g., a control cell, such as a HeLa cell, HEK293 cell, mesenchymal cell, etc.). In some embodiments, the cell of the immune system (immune cell) in which the immune-associated miRNA is expressed is a B cell, T cell, Killer T cell, Helper T cell, γδ T cell, dendritic cell, macrophage, monocyte, vascular endothelial cell. or other immune cell. In some embodiments, the cell of the immune system is a B cell expressing one or more of the following markers: B220, BLAST-2 (EBVCS), Bu-1, CD19, CD20 (L26), CD22, CD24, CD27, CD57, CD72, CD79a, CD79b, CD86, chB6, D8/17, FMC7, L26, M17, MUM-1, Pax-5 (BSAP), and PC47H. In some embodiments, the cell of the immune system is a T cell expressing one or more of the following markers: ART2, CD1a, CD1d, CD11b (Mac-1), CD134 (OX40), CD150, CD2, CD25 (interleukin 2 receptor alpha), CD3, CD38, CD4, CD45RO, CD5, CD7, CD72, CD8, CRTAM, FOXP3, FT2, GPCA, HLA-DR, HML-1, HT23A, Leu-22, Ly-2, Ly-m22, MICG, MRC OX 8, MRC OX-22, OX40, PD-1 (Programmed death-1), RT6, TCR (T cell receptor), Thy-1 (CD90), and TSA-2 (Thymic shared Ag-2). In some embodiments, the immune-associated miRNA is selected from: miR-15a, miR-16-1, miR-17, miR-18a, miR-19a, miR-19b-1, miR-20a, miR-21, miR-29a/b/c, miR-30b, miR-31, miR-34a, miR-92a-1, miR-106a, miR-125a/b, miR-142-3p, miR-146a, miR-150, miR-155, miR-181a, miR-223 and miR-424, miR-221, miR-222, let-7i, miR-148, and miR-152. In some embodiments, a transgene described herein comprises one or more binding sites for miR-142.

Inhibitory Nucleic Acids

Aspects of the disclosure relate to isolated nucleic acids encoding one or more inhibitory nucleic acids, also referred to as inhibitory oligonucleotides. Inhibitory oligonucleotides can be single-stranded or double-stranded. In some embodiments, inhibitory oligonucleotides are DNA or RNA. Inhibitory oligonucleotides may interfere with gene expression, transcription and/or translation. In some embodiments, an inhibitory oligonucleotide (e.g., inhibitory nucleic acid) is a dsRNA, siRNA, shRNA, miRNA, artificial miRNA (amiRNA), or antisense oligonucleotide (ASO).

In some embodiments, an inhibitory nucleic acid is a hairpin-forming RNA. Generally, hairpin-forming RNAs are arranged into a self-complementary "stem-loop" structure that includes a single nucleic acid encoding a stem portion having a duplex comprising a sense strand (e.g., passenger strand) connected to an antisense strand (e.g., guide strand) by a loop sequence. The passenger strand and the guide strand share complementarity. In some embodiments, the passenger strand and guide strand share 100% complementarity. In some embodiments, the passenger strand and guide strand share at least 50%, at least 60%, at least 70%, at least 80%, at least 90%, at least 95%, or at least 99% complementarity. A passenger strand and a guide strand may lack complementarity due to a base-pair mismatch. In some embodiments, the passenger strand and guide strand of a hairpin-forming RNA have at least 1, at least 2, at least 3, at least 4, at least 5, at least 6, at least 7 at least 8, at least 9, or at least 10 mismatches. Generally, the first 2-8 nucleotides of the stem (relative to the loop) are referred to as "seed" residues and play an important role in target recognition and binding. The first residue of the stem (relative to the loop) is referred to as the "anchor" residue. In some embodiments, hairpin-forming RNA have a mismatch at the anchor residue. In some embodiments, a uracil (U) nucleobase may be used in place of a thymine (T) nucleobase.

Hairpin-forming RNA are useful for translational repression and/or gene silencing via the RNAi pathway. Due to having a common secondary structure, hairpin-forming RNA share the characteristic of being processed by the proteins Drosha and Dicer prior to being loaded into the RNA-induced silencing complex (RISC). Duplex length amongst hairpin-forming RNA can vary. In some embodiments, a duplex is between about 19 nucleotides and about 200 nucleotides in length. In some embodiments, a duplex is between about between about 14 nucleotides to about 35 nucleotides in length. In some embodiments, a duplex is between about 19 and 150 nucleotides in length. In some embodiments, hairpin-forming RNA has a duplex region that is 19, 20, 21, 22, 23, 24, 25, 26, 27, 28, 29, 30, 31, 32, or 33 nucleotides in length. In some embodiments, a duplex is between about 19 nucleotides and 33 nucleotides in length. In some embodiments, a duplex is between about 40 nucleotides and 100 nucleotides in length. In some embodiments, a duplex is between about 60 and about 80 nucleotides in length.

In some embodiments, the hairpin-forming RNA is a microRNA (miRNA), or artificial microRNA (AmiRNA). A microRNA (miRNA) is a small non-coding RNA found in plants and animals and functions in transcriptional and post-translational regulation of gene expression. An artificial microRNA (AmiRNA) is derived by modifying native miRNA to replace natural targeting regions of pre-mRNA with a targeting region of interest. For example, a naturally occurring, expressed miRNA can be used as a scaffold or backbone (e.g., a pri-miRNA scaffold), with the stem sequence replaced by that of an miRNA targeting a gene of interest. An artificial precursor microRNA (pre-amiRNA) is normally processed such that one single stable small RNA is preferentially generated. In some embodiments, scAAV vectors and scAAVs described herein comprise a nucleic acid encoding an AmiRNA. In some embodiments, the pri-miRNA scaffold of the AmiRNA is derived from a pri-miRNA selected from the group consisting of pri-MIR-21, pri-MIR-22, pri-MIR-26a, pri-MIR-30a, pri-MIR-33, pri-MIR-122, pri-MIR-375, pri-MIR-199, pri-MIR-99, pri-MIR-194, pri-MIR-155, and pri-MIR-451.

In some embodiments, isolated nucleic acids provided herein may be in the form of small interfering RNAs (siRNA), also known as short interfering RNA or silencing RNA. siRNA, is a class of double-stranded RNA molecules, typically about 20-25 base pairs in length that target nucleic acids (e.g., mRNAs) for degradation via the RNA interference (RNAi) pathway in cells. Specificity of siRNA molecules may be determined by the binding of the antisense strand of the molecule to its target RNA. Effective siRNA molecules are generally less than 30 to 35 base pairs in length to prevent the triggering of non-specific RNA interference pathways in the cell via the interferon response, although longer siRNA can also be effective.

The siRNA molecule can be double stranded (e.g. a dsRNA molecule comprising an antisense strand and a complementary sense strand) or single-stranded (e.g. a ssRNA molecule comprising just an antisense strand). The siRNA molecules can comprise a duplex, asymmetric duplex, hairpin or asymmetric hairpin secondary structure, having self-complementary sense and antisense strands.

Generally, inhibitory oligonucleotides bind to a target polynucleotide via a region of complementarity. For example, binding of inhibitory oligonucleotide to a target polynucleotide can trigger RNAi pathway-mediated degradation of the target polynucleotide (in the case of dsRNA, siRNA, shRNA, etc.), or can block the translational machinery (e.g., antisense oligonucleotides). In some embodiments, an inhibitory nucleic acid binds specifically to a target polynucleotide (e.g., a target nucleotide sequence). As used herein, an oligonucleotide that "binds specifically" refers to an inhibitory nucleic acid that binds with higher affinity to one particular polynucleotide than other polynucleotides. In some embodiments, an oligonucleotide that "binds specifically" to a target binds only to the target polynucleotide sequence (e.g., does not bind to any off-target polynucleotide sequences).

An inhibitory nucleic acid typically comprises a region of complementarity with a target polynucleotide (e.g., a nucleic acid sequence encoding a RPGR$^{ORF15}$ protein or a RPGR$^{CONST}$ protein). A region of complementarity may range in length from about 2 nucleotides to about 50 nucleotides (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 4-, 41, 42, 43, 44, 45, 46, 47, 48, 49, or 50 nucleotides). In some embodiments, a region of complementarity ranges from about 5 nucleotides to about 25 nucleotides in length.

The percentage identity within a region of complementarity may vary. In some embodiments, an inhibitory nucleic acid shares at least 80%, 85%, 90%, 95%, 99%, or 99.9% percent identity with a target polynucleotide within a region of complementarity. In some embodiments, an inhibitory nucleic acid shares 100% identity with (e.g., is completely identical to) a target polynucleotide within a region of complementarity. In some embodiments, an inhibitory nucleic acid comprises at least 1, 2, 3, 4, 5, 6, 7, 8, 9, or 10 mismatches (e.g., non-complementary bases, inserted nucleotides, gaps, etc.) with a target polynucleotide within a region of complementarity.

In some embodiments, inhibitory oligonucleotides have a region of complementarity that is complementary with at least 8 nucleotides of an mRNA encoded by a RPGR gene (e.g., an mRNA encoding a RPGR$^{CONST}$ protein or RPGR$^{ORF15}$ protein). In some embodiments, an inhibitory nucleic acid comprises a sequence that is at least 50%, 60%, 70%, 80%, 90%, 95%, 99%, or 100% identical to the nucleic acid sequence set forth in any one of SEQ ID NO: 1-14. In some embodiments, an inhibitory nucleic acid binds to a target polynucleotide (e.g., shares a region of complementarity with a target polynucleotide) that comprises a sequence that is at least 50%, 60%, 70%, 80%, 90%, 95%, 99%, or 100% identical to the nucleic acid sequence set forth in any one of SEQ ID NO: 1-14, or a complement or reverse complement thereof.

In some embodiments, inhibitory oligonucleotides are modified nucleic acids. The term "nucleotide analog" or "altered nucleotide" or "modified nucleotide" refers to a non-standard nucleotide, including non-naturally occurring ribonucleotides or deoxyribonucleotides. In some embodiments, nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, NH2, NHR, NR2, COOR, or OR, wherein R is substituted or unsubstituted C.sub.1-C.sub.6 alkyl, alkenyl, alkynyl, aryl, etc. Other possible modifications include those described in U.S. Pat. Nos. 5,858,988, and 6,291,438. A locked nucleic acid (LNA), often referred to as inaccessible RNA, is a modified RNA nucleotide. The ribose moiety of an LNA nucleotide is modified with an extra bridge connecting the 2' oxygen and 4' carbon.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000

Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro. In some embodiments, the inhibitory oligonucleotide is a modified inhibitory oligonucleotide. In some embodiments, the modified inhibitory oligonucleotide comprises a locked nucleic acid (LNA), phosphorothioate backbone, and/or a 2'-OMe modification.

In some embodiments, an inhibitory nucleic acid is an amiRNA. In some embodiments, an amiRNA comprises an miRNA backbone selected from: miR-168, miR-157, miR-155, and miR-30 backbone. In some embodiments, an amiRNA comprises an miRNA backbone of miR-168. In some embodiments, an amiRNA comprises an miRNA backbone of miR-157. In some embodiments, an amiRNA comprises an miRNA backbone of miR-155. In some embodiments, an amiRNA comprises an miRNA backbone of miR-30.

In some embodiments, an inhibitory nucleic acid may comprise a "Tough Decoy," "Tough RNA Decoys" or "TuDs," which are stabilized stem-loop RNA constructs containing miRNA binding domains (as further described in Haraguchi et al., Nucleic Acids Res., 2009; Xie et al., Nature, 2012). In so using TuDs the effect of miRNAs on inhibiting an RNA (e.g., mRNA) can be countered (e.g., the inhibitory effect of miRNAs can be lessened/inhibited), thus increasing the RNA (e.g., mRNA) available (e.g., for translation). In some embodiments, a TuD comprises a binding site for an miRNA that binds RPGR. In some embodiments, the RPGR is RPGR$^{CONST}$. In some embodiments, the RPGR is RPGR$^{ORF15}$. In some embodiments, a TuD comprises a binding site for (e.g., a region of complementarity with) any of the miRNA of the instant disclosure. In some embodiments, a TuD comprises a binding site for miR-168, miR-157, miR-155, miR-30, miR-129, and/or miR-26a. In some embodiments, a TuD comprises TuD-129. In some embodiments, TuD-129 comprises a binding site for miR-129 (or encodes a binding site for miR-129). In some embodiments, TuD-129 is encoded by or comprises SEQ ID NO: 35. In some embodiments, a TuD comprises TuD-26a. In some embodiments, TuD-26a comprises a binding site for miR-26a (or encodes a binding site for miR-26a). In some embodiments, TuD-26a is encoded by or comprises SEQ ID NO: 36. In some embodiments, administering a TuD results in a change in cilial length of the cell or the cells of the subject In some embodiments, a recombinant adeno-associated virus (rAAV) comprises a nucleic acid encoding a TuD of the disclosure. In some embodiments, a recombinant adeno-associated virus (rAAV) comprising a transgene comprising a nucleic acid sequence encoding a TuD of the disclosure. In some embodiments an rAAV comprises an AAV8 capsid protein. In some embodiments, a transgene further comprises a promoter operably linked to the nucleic acid sequence encoding a TuD.

It is readily apparent and well-known to the skilled artisan that when interpreting and reading sequence information related to inhibitory nucleic acids, that even though thymine (T) may be stated in a sequence (e.g., SEQ ID NO:), uracil is known to the corollary base for RNA. Accordingly, when interpreting the sequence data and information herein, the skilled artisan shall use the common knowledge in the field and context of the sequence to interpret the appropriate base (e.g., T in the case of DNA sequences/compositions and U in the case of RNA sequences/compositions).

In some embodiments, a first region further comprises a first promoter operably linked to a sequence encoding an inhibitory nucleic acid.

In some embodiments, a first promoter is a constitutive promoter, inducible promoter, or tissue-specific promoter. In some embodiments, a first promoter is a constitutive promoter. In some embodiments, a first promoter is an inducible promoter. In some embodiments, a first promoter is a tissue-specific promoter. In some embodiments, a first promoter is a RNA polymerase III (pol III) promoter. In some embodiments, a pol III promoter is a U6 promoter or H1 promoter. In some embodiments, a pol III promoter is a U6 promoter. In some embodiments, a pol III promoter is a H1 promoter.

In some embodiments, an expression cassette further comprises a second region encoding a RPGR$^{ORF15}$ protein. In some embodiments, an RPGR$^{ORF15}$ protein comprises the amino acid sequence set forth in SEQ ID NO: 15. In some embodiments, an RPGR$^{ORF15}$ protein is encoded by the nucleic acid sequence set forth in SEQ ID NO: 16. In some embodiments, an expression cassette further comprises a second region encoding a RPGR$^{ORF15}$ protein. In some embodiments, an RPGR$^{ORF15}$ protein comprises the amino acid sequence set forth in SEQ ID NO: 17. In some embodiments, an RPGR$^{ORF15}$ protein is encoded by the nucleic acid sequence set forth in SEQ ID NO: 18.

In some embodiments, a second region comprises a second promoter operably linked to the sequence encoding the RPGR$^{ORF15}$ protein. In some embodiments, a second promoter is a constitutive promoter, inducible promoter, or tissue-specific promoter. In some embodiments, a second promoter is a RNA polymerase II (pol II) promoter.

Vectors

The disclosure relates, in some aspects, to vectors encoding inhibitory nucleic acids as described herein. As used herein, the term "vector" includes any genetic element, such as a plasmid, phage, transposon, cosmid, chromosome, artificial chromosome, virus, virion, etc., which is capable of replication when associated with the proper control elements and which can transfer gene sequences between cells. In some embodiments, a vector is a viral vector, such as an rAAV vector, a lentiviral vector, an adenoviral vector, a retroviral vector, etc. Thus, the term includes cloning and expression vehicles, as well as viral vectors. In some embodiments, useful vectors are contemplated to be those vectors in which the nucleic acid segment to be transcribed is positioned under the transcriptional control of a promoter.

In some embodiments, the isolated nucleic acid comprises inverted terminal repeats. The isolated nucleic acids of the disclosure may be recombinant adeno-associated virus (AAV) vectors (rAAV vectors). In some embodiments, an isolated nucleic acid as described by the disclosure comprises a region (e.g., a first region) comprising a first adeno-associated virus (AAV) inverted terminal repeat (ITR), or a variant thereof. The isolated nucleic acid (e.g., the recombinant AAV vector) may be packaged into a capsid protein and administered to a subject and/or delivered to a selected target cell. "Recombinant AAV (rAAV) vectors" are typically composed of, at a minimum, one or more transgene (e.g., the first and second transgene described herein) and its regulatory sequences, and 5' and 3' AAV inverted terminal repeats (ITRs). The one or more transgene may comprise a region encoding, for example, a first transgene product (e.g., an inhibitory nucleic acid) and a second transgene (e.g., a sequence encoding a RPGR$^{ORF15}$ protein) and/or an expression control sequence (e.g., a poly-A tail), as described elsewhere in the disclosure.

Generally, ITR sequences are about 145 bp in length. Preferably, substantially the entire sequences encoding the ITRs are used in the molecule, although some degree of minor modification of these sequences is permissible. The ability to modify these ITR sequences is within the skill of the art. (See, e.g., texts such as Sambrook et al., "Molecular Cloning. A Laboratory Manual", 2d ed., Cold Spring Harbor Laboratory, New York (1989); and K. Fisher et al., J Virol., 70:520 532 (1996)). An example of such a molecule employed in the disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including presently identified mammalian AAV types. In some embodiments, the isolated nucleic acid further comprises a region (e.g., a second region, a third region, a fourth region, etc.) comprising a second AAV ITR. In some embodiments, an isolated nucleic acid encoding a transgene is flanked by AAV ITRs (e.g., in the orientation 5'-ITR-transgene-ITR-3'). In some embodiments, the AAV ITRs are selected from the group consisting of AAV1 ITR, AAV2 ITR, AAV3 ITR, AAV4 ITR, AAV5 ITR, and AAV6 ITR.

In some embodiments, the isolated nucleic acid as described herein comprises a 5' AAV ITR, a first expression cassette described herein, optionally a second expression cassette described herein, and a 3' AAV ITR.

In some aspects, the disclosure provides a composition comprising an isolated nucleic acid or rAAV as described herein, and a pharmaceutically acceptable excipient. In some embodiments, a composition is formulated for intravitreal or subretinal injection. In some embodiments, a composition is formulated for intravitreal injection. In some embodiments, a composition is formulated for subretinal injection. In some embodiments, a composition is formulated for topical application to the eye.

In some aspects, the disclosure provides isolated adeno-associated viruses (AAVs). As used herein with respect to AAVs, the term "isolated" refers to an AAV that has been artificially produced or obtained. Isolated AAVs may be produced using recombinant methods. Such AAVs are referred to herein as "recombinant AAVs". Recombinant AAVs (rAAVs) preferably have tissue-specific targeting capabilities, such that a transgene of the rAAV will be delivered specifically to one or more predetermined tissue(s) (e.g., ocular tissues). The AAV capsid is an important element in determining these tissue-specific targeting capabilities (e.g., tissue tropism). Thus, an rAAV having a capsid appropriate for the tissue being targeted can be selected.

In some embodiments, the rAAV of the present disclosure comprises a capsid protein containing the isolated nucleic acid described herein.

Methods for obtaining recombinant AAVs having a desired capsid protein are well known in the art. (See, for example, US 2003/0138772, the contents of which are incorporated herein by reference in their entirety). Typically the methods involve culturing a host cell which contains a nucleic acid sequence encoding an AAV capsid protein; a functional rep gene; a recombinant AAV vector composed of AAV inverted terminal repeats (ITRs) and a transgene; and sufficient helper functions to permit packaging of the recombinant AAV vector into the AAV capsid proteins. In some embodiments, capsid proteins are structural proteins encoded by the cap gene of an AAV. AAVs comprise three capsid proteins, virion proteins 1 to 3 (named VP1, VP2 and VP3), all of which are transcribed from a single cap gene via alternative splicing. In some embodiments, the molecular weights of VP1, VP2 and VP3 are respectively about 87 kDa, about 72 kDa and about 62 kDa. In some embodiments, upon translation, capsid proteins form a spherical 60-mer protein shell around the viral genome. In some embodiments, the functions of the capsid proteins are to protect the viral genome, deliver the genome and interact with the host. In some aspects, capsid proteins deliver the viral genome to a host in a tissue specific manner.

In some embodiments, an AAV capsid protein has a tropism for ocular tissues or muscle tissue. In some embodiments, an AAV capsid protein targets ocular cell types (e.g., photoreceptor cells, retinal cells, etc.).

In some embodiments, an AAV capsid protein is of an AAV serotype selected from the group consisting of AAV1, AAV2, AAV3, AAV4, AAV5, AAV6, AAV7, AAV8, AAV9, AAV9.hr, AAVrh8, AAVrh10, AAVrh39, AAVrh43, AAV.PHP, and variants of any of the foregoing. In some embodiments, an AAV capsid protein is of a serotype derived from a non-human primate, for example AAVrh8 serotype. In some embodiments, the capsid protein is of AAV serotype 6 (e.g., AAV6 capsid protein), AAV serotype 8 (e.g., AAV8 capsid protein), AAV serotype 2 (e.g., AAV2 capsid protein), AAV serotype 5 (e.g., AAV5 capsid protein), or AAV serotype 9 (e.g., AAV9 capsid protein). In some embodiments, the AAV capsid protein with desired tissue tropism can be selected from AAV capsid proteins isolated from mammals (e.g., tissue from a subject). (See, for example, WO2010138263A2 and WO2018071831, the entire contents of which are incorporated herein by reference).

In some embodiments, the rAAV described herein is a single stranded AAV (ssAAV). An ssAAV, as used herein, refers to an rAAV with the coding sequence and complementary sequence of the transgene expression cassette on separate strands and are packaged in separate viral capsids.

The components to be cultured in the host cell to package an rAAV vector in an AAV capsid may be provided to the host cell in trans. Alternatively, any one or more of the required components (e.g., recombinant AAV vector, rep sequences, cap sequences, and/or helper functions) may be provided by a stable host cell which has been engineered to contain one or more of the required components using methods known to those of skill in the art. Most suitably, such a stable host cell will contain the required component(s) under the control of an inducible promoter. However, the required component(s) may be under the control of a constitutive promoter. Examples of suitable inducible and constitutive promoters are provided herein, in the discussion of regulatory elements suitable for use with the transgene. In still another alternative, a selected stable host cell may contain selected component(s) under the control of a constitutive promoter and other selected component(s) under the control of one or more inducible promoters. For example, a stable host cell may be generated which is derived from 293 cells (which contain E1 helper functions under the control of a constitutive promoter), but which contain the rep and/or cap proteins under the control of inducible promoters. Still other stable host cells may be generated by one of skill in the art.

A "host cell" refers to any cell that harbors, or is capable of harboring, a substance of interest. Often a host cell is a mammalian cell. In some embodiments, a host cell is a photoreceptor cell, retinal pigment epithelial cell, keratinocyte, corneal cell, and/or a tumor cell. A host cell may be used as a recipient of an AAV helper construct, an AAV minigene plasmid, an accessory function vector, or other transfer DNA associated with the production of recombinant AAVs. The term includes the progeny of the original cell which has been transfected. Thus, a "host cell" as used herein may refer to a cell which has been transfected with an exogenous DNA sequence. It is understood that the progeny of a single parental cell may not necessarily be completely identical in morphology or in genomic or total DNA complement as the original parent, due to natural, accidental, or deliberate mutation. In some embodiments, the host cell is a mammalian cell, a yeast cell, a bacterial cell, an insect cell, a plant cell, or a fungal cell. In some embodiments, the host cell is a neuron, a photoreceptor cell, a pigmented retinal epithelial cell, or a glial cell.

The recombinant AAV vector, rep sequences, cap sequences, and helper functions required for producing the rAAV of the disclosure may be delivered to the packaging host cell using any appropriate genetic element (vector). The selected genetic element may be delivered by any suitable method, including those described herein. The methods used to construct any embodiment of this disclosure are known to those with skill in nucleic acid manipulation and include genetic engineering, recombinant engineering, and synthetic techniques. See, e.g., Sambrook et al., Molecular Cloning: A Laboratory Manual, Cold Spring Harbor Press, Cold Spring Harbor, N.Y. Similarly, methods of generating rAAV virions are well known and the selection of a suitable method is not a limitation on the disclosure. See, e.g., K. Fisher et al., J. Virol., 70:520-532 (1993) and U.S. Pat. No. 5,478,745.

In some embodiments, recombinant AAVs may be produced using the triple transfection method (described in detail in U.S. Pat. No. 6,001,650). Typically, the recombinant AAVs are produced by transfecting a host cell with an AAV vector (comprising a transgene flanked by ITR elements) to be packaged into AAV particles, an AAV helper function vector, and an accessory function vector. An AAV helper function vector encodes the "AAV helper function" sequences (e.g., rep and cap), which function in trans for productive AAV replication and encapsidation. Preferably, the AAV helper function vector supports efficient AAV vector production without generating any detectable wild-type AAV virions (e.g., AAV virions containing functional rep and cap genes). Non-limiting examples of vectors suitable for use with the disclosure include pHLP19, described in U.S. Pat. No. 6,001,650 and pRep6cap6 vector, described in U.S. Pat. No. 6,156,303, the entirety of both incorporated by reference herein. The accessory function vector encodes nucleotide sequences for non-AAV derived viral and/or cellular functions upon which AAV is dependent for replication (e.g., "accessory functions"). The accessory functions include those functions required for AAV replication, including, without limitation, those moieties involved in activation of AAV gene transcription, stage specific AAV mRNA splicing, AAV DNA replication, synthesis of cap expression products, and AAV capsid assembly. Viral-based accessory functions can be derived from any of the known helper viruses such as adenovirus, herpes virus (other than herpes simplex virus type-1), and vaccinia virus.

In some aspects, the disclosure provides transfected host cells. The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous nucleic acids, such as a nucleotide integration vector and other nucleic acid molecules, into suitable host cells.

As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

Delivery

The isolated nucleic acids, rAAVs, and compositions of the disclosure may be delivered to a subject in compositions according to any appropriate methods known in the art. For example, an rAAV, preferably suspended in a physiologically compatible carrier (e.g., in a composition), may be administered to a subject, i.e., host animal, such as a human, mouse, rat, cat, dog, sheep, rabbit, horse, cow, goat, pig, guinea pig, hamster, chicken, turkey, or a non-human primate (e.g., Macaque). In some embodiments a host animal does not include a human.

Delivery of compositions to a mammalian subject may be by, for example, intraocular injection, subretinal injection, or by injection into the eye of the mammalian subject to ocular tissues. As used herein, "ocular tissues" refers to any tissue derived from or contained in the eye. Non-limiting examples of ocular tissues include neurons, retina (e.g., photoreceptor cells), sclera, choroid, retina, vitreous body, macula, fovea, optic disc, lens, pupil, iris, aqueous fluid, cornea, conjunctiva ciliary body, and optic nerve. The retina is located in the posterior of the eye and comprises photoreceptor cells. These photoreceptor cells (e.g., rods, cones) confer visual acuity by discerning color, as well as contrast in the visual field.

In some embodiments, delivery is to the CNS of a subject. In some embodiments, an isolated nucleic acid as described herein is delivered to CNS tissue or cells (e.g., neurons, oligodendrocytes, etc.) or the area between CNS cells, such as a synapse.

Alternatively, delivery of the compositions to a mammalian subject may be by intramuscular injection or by administration into the bloodstream of the mammalian subject. Administration into the bloodstream may be by injection into a vein, an artery, or any other vascular conduit. In some embodiments, the rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer the virions into the vasculature of an isolated limb to potentially enhance transduction into muscle cells or tissue. In some embodiments, a composition as described in the disclosure is administered by intraocular injection. In some embodiments, a composition as described in the disclosure is administered by subretinal injection. In some embodiments, a composition as described in the disclosure is administered by intravenous injection.

Aspects of the instant disclosure relate to compositions comprising a recombinant AAV comprising a capsid protein and a nucleic acid encoding a transgene, wherein the transgene comprises a nucleic acid sequence encoding one or more inhibitory nucleic acids as described herein. In some embodiments, the nucleic acid further comprises AAV ITRs. In some embodiments, a composition further comprises a pharmaceutically acceptable carrier.

The compositions of the disclosure may comprise a composition alone, or in combination with one or more other compositions (e.g., a second composition encoding having one or more different transgenes). In some embodiments, a composition comprises 1, 2, 3, 4, 5, 6, 7, 8, 9, 10, or more different compositions each having one or more different transgenes.

Suitable carriers may be readily selected by one of skill in the art in view of the indication for which the composition is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the disclosure.

Optionally, the compositions of the disclosure may contain, in addition to the active ingredient (e.g., inhibitory nucleic acid) and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, parachlorophenol, and poloxamers (non-ionic surfactants) such as Pluronic® F-68. Suitable chemical stabilizers include gelatin and albumin.

The compositions are administered in sufficient amounts to transfect the cells of a desired tissue and to provide sufficient levels of gene transfer and expression without undue adverse effects. Conventional and pharmaceutically acceptable routes of administration include, but are not limited to, direct delivery to the selected organ (e.g., intraportal delivery to the liver), intraocular injection, subretinal injection, oral, inhalation (including intranasal and intratracheal delivery), intravenous, intramuscular, subcutaneous, intradermal, intratumoral, and other parental routes of administration. Routes of administration may be combined, if desired.

The dose of rAAV virions required to achieve a particular "therapeutic effect," e.g., the units of dose in genome copies/per kilogram of body weight (GC/kg), will vary based on several factors including, but not limited to: the route of rAAV virion administration, the level of gene or RNA expression required to achieve a therapeutic effect, the specific disease or disorder being treated, and the stability of the gene or RNA product. One of skill in the art can readily determine a rAAV virion dose range to treat a patient having a particular disease or disorder based on the aforementioned factors, as well as other factors that are well known in the art.

An effective amount of a composition is an amount sufficient to target a desired tissue (e.g., muscle tissue, ocular tissue, etc.). In some embodiments, an effective amount of a composition is administered to the subject during a pre-symptomatic stage of degenerative disease. In some embodiments, a subject is administered a composition after exhibiting one or more signs or symptoms of degenerative disease. In some embodiments, an effective amount of an rAAV ranges between 1×109 and 1×1014 genome copies of the rAAV.

An effective amount may also depend on the mode of administration. For example, targeting an ocular (e.g., corneal) tissue by intrastromal administration or subcutaneous injection may require different (e.g., higher or lower) doses, in some cases, than targeting an ocular (e.g., corneal) tissue by another method (e.g., systemic administration, topical administration). In some embodiments, intrastromal injection (IS) of rAAV having certain serotypes (e.g., AAV2, AAV5, AAV6, AAV6.2, AAV7, AAV8, AAV9, AAVrh.8, AAVrh.10, AAVrh.39, and AAVrh.43) mediates efficient transduction of ocular (e.g., corneal, retinal, etc.) cells. Thus, in some embodiments, the injection is intrastromal injection (IS). In some embodiments, the injection is topical administration (e.g., topical administration to an eye). In some cases, multiple doses of a rAAV are administered.

In some embodiments, rAAV compositions are formulated to reduce aggregation of AAV particles in the composition, particularly where high rAAV concentrations are present (e.g., ~1013 GC/mL or more). Methods for reducing aggregation of rAAVs are well known in the art and, include, for example, addition of surfactants, pH adjustment, salt concentration adjustment, etc. (See, e.g., Wright F R, et al., Molecular Therapy (2005) 12, 171-178, the contents of which are incorporated herein by reference.)

Formulation of pharmaceutically-acceptable excipients and carrier solutions is well-known to those of skill in the art, as is the development of suitable dosing and treatment regimens for using the particular compositions described herein in a variety of treatment regimens.

Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver therapeutic constructs in suitably formulated pharmaceutical compositions disclosed herein either intraocularlly, subretinally, subcutaneously, intraopancreatically, intranasally, parenterally, intravenously, intramuscularly, intrathecally, orally, intraperitoneally, or by inhalation. In some embodiments, the administration modalities as described in U.S. Pat. Nos. 5,543,158; 5,641,515 and 5,399,363 (each specifically incorporated herein by reference in its entirety) may be used to deliver rAAVs. In some embodiments, a preferred mode of administration is by portal vein injection.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active ingredient (e.g., one or more inhibitory nucleic acids) in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the composi tions of the disclosure into suitable host cells. In particular, compositions described herein may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the rAAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes have been used successfully with a number of cell types that are normally resistant to transfection by other procedures. In addition, liposomes are free of the DNA length constraints that are typical of viral-based delivery systems. Liposomes have been used effectively to introduce genes, drugs, radiotherapeutic agents, viruses, transcription factors and allosteric effectors into a variety of cultured cell lines and animals. In addition, several successful clinical trials examining the effectiveness of liposome-mediated drug delivery have been completed.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

In addition to the methods of delivery described above, the following techniques are also contemplated as alternative methods of delivering the rAAV compositions to a host. Sonophoresis (i.e., ultrasound) has been used and described in U.S. Pat. No. 5,656,016 as a device for enhancing the rate and efficacy of drug permeation into and through the circulatory system. Other drug delivery alternatives contemplated are intraosseous injection (U.S. Pat. No. 5,779,708), microchip devices (U.S. Pat. No. 5,797,898), ophthalmic formulations (Bourlais et al., 1998), transdermal matrices (U.S. Pat. Nos. 5,770,219 and 5,783,208) and feedback-controlled delivery (U.S. Pat. No. 5,697,899).

Methods

Aspects of the disclosure relate to methods for delivering a transgene encoding one or more inhibitory nucleic acids to a cell (e.g., a cell in a subject). In some embodiments, methods described by the disclosure are useful for treating a subject having or suspected of having a disease associated with aberrant expression or activity of RPGR protein, for example diseases associated with defects in cilial length, also referred to as "ciliopathies". Generally, a "ciliopathy" refers to a disease or disorder characterized by defective (or lack of) protein function resulting in abnormal formation or function of cilia in a cell of a subject. An "ocular ciliopathy" is a ciliopathy where abnormal formation or function of cilial occurs in ocular cells (e.g., rods, cones, photoreceptor cells, etc.) of a subject, typically resulting in retinal degen eration, loss of vision and blindness. Examples of ciliopathies include but are not limited to Alstrom syndrome, Bardet-Biedl syndrome, Joubert syndrome, Merckel syndrome, nephronophthisis, orofaciodigital syndrome, Senior-Locken syndrome, polycystic kidney disease, primary ciliary dyskinesia, situs inversus. In some embodiments, retinal dystrophies (e.g., due to an ocular ciliopathy) are more commonly presented in a non-syndromic manner.

A subject having or suspected of having a ciliopathy may comprise one or more mutations in an RPGR gene. Mutations in RPGR are well known, and are described for example in the RPGR Allelic Variant Database (http://rpgr.hgu.mrc.ac.uk/index.php?select_db=RPGR). Examples of ciliopathies associated with aberrant expression or activity of RPGR protein include but are not limited to retinitis pigmentosa (RP), X-linked rod-cone dystrophy, certain hearing disorders (e.g., hearing loss), certain respiratory diseases, and recurrent infections of the ear, sinuses, and respiratory tract, for example as disclosed by Iannaccone et al. (2004) AJO 137(4):785-786 and Iannaccone et al. (2003) Journal of Medical Genetics 40:e118.

As used herein, the term "treating" refers to the application or administration of a composition (e.g., an isolated nucleic acid or rAAV as described herein) to a subject, who has a ciliopathy, or a predisposition toward a ciliopathy (e.g., one or more mutations in the RPGR gene), with the purpose to cure, heal, alleviate, relieve, alter, remedy, ameliorate, improve, or affect the disorder, the symptom of the disease, or the predisposition toward the ciliopathy.

Alleviating a disease includes delaying the development or progression of the disease, or reducing disease severity. Alleviating the disease does not necessarily require curative results. As used therein, "delaying" the development of a disease (such as a disease associated with a ciliopathy) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a ciliopathy includes initial onset and/or recurrence.

In some embodiments, a subject having a ciliopathy is administered an effective amount of an isolated nucleic acid described herein. An "effective amount" of a substance is an amount sufficient to produce a desired effect. In some embodiments, an effective amount of an isolated nucleic acid (e.g., an isolated nucleic acid encoding an inhibitory nucleic acid as described herein) is an amount sufficient to transfect (or infect in the context of rAAV mediated delivery) a sufficient number of target cells of a target tissue of a subject. In some embodiments, a target tissue is ocular tissue (e.g., photoreceptor cells, rod cells, cone cells, retinal ganglion cells, retinal cells, etc.). In some embodiments, an effective amount of an isolated nucleic acid (e.g., which may be delivered via an rAAV) may be an amount sufficient to have a therapeutic benefit in a subject, e.g., to increase or supplement the expression of a gene or protein of interest (e.g., certain isoforms of RPGR, such as $RPGR^{ORF15}$), to improve in the subject one or more symptoms of disease (e.g., a symptom of an ocular ciliopathy, such as RP), etc. The effective amount will depend on a variety of factors such as, for example, the species, age, weight, health of the subject, and the tissue to be targeted, and may thus vary among subject and tissue as described elsewhere in the disclosure.

In some embodiments, isolated nucleic acids described by the disclosure (e.g., inhibitory nucleic acids targeting RPGR isoforms) are useful for identifying and/or treating diseases associated with aberrant cilial length (e.g., retinitis pigmentosa (RP), X-linked rod-cone dystrophy, certain hearing disorders, etc.) in a subject in need thereof. Thus, in some embodiments, the disclosure provides a method for decreasing length of cell cilia, the method comprising administering to the cell an isolated nucleic acid as described herein. In some embodiments, the disclosure provides a method for increasing length of cell cilia, the method comprising administering to the cell an isolated nucleic acid as described herein.

The increase or reduction in cilial length after treatment with an inhibitory nucleic acid as described herein may vary. In some embodiments, administration of an inhibitory nucleic acid results in a cilial length increase of between 1% and 500% (e.g. any number between 1 and 500% inclusive) relative to cilial length of the cell prior to the administration. In some embodiments, administration of an inhibitory nucleic acid results in a cilial length increase of more than 500% relative to cilial length of the cell prior to the administration. In some embodiments, administration of an inhibitory nucleic acid results in a cilial length decrease of between 1% and 500% (e.g. any number between 1 and 500% inclusive) relative to cilial length of the cell prior to the administration. In some embodiments, administration of an inhibitory nucleic acid results in a cilial length decrease of more than 500% relative to cilial length of the cell prior to the administration.

Aspects of the disclosure are based on the recognition that, surprisingly, the ratio of certain RPGR protein isoforms in a cell affects cilial length of the cell, and that overexpression of certain isoforms (e.g., $RPGR^{ORF15}$) is cytotoxic. Without wishing to be bound by any particular theory, determination of the $RPGR^{ORF15}$:$RPGR^{CONST}$ ratio in a cell is useful, in some embodiments, for selecting patients for $RGPR^{ORF15}$ supplementation therapy. Accordingly, in some aspects, the disclosure provides a method for selecting a therapeutic regimen for a subject, the method comprising: determining an expression level of a $RPGR^{ORF15}$ in a biological sample obtained from a subject; determining an expression level of a $RPGR^{CONST}$ in the biological sample; calculating a $RPGR^{ORF15}$:$RPGR^{CONST}$ ratio based upon the expression levels; and, administering to the subject an isolated nucleic acid as described herein if the ratio of $RPGR^{ORF15}$:$RPGR^{CONST}$ is greater than about 1:0.5, 1:1, 2:1, 3:1, 4:1, 5:1, 6:1, 7:1, 8:1, 9:1, or 10:1, or the ratio of $RPGR^{CONST}$: $RPGR^{ORF15}$ is greater than about 1:0.5, 1:1, 2:1, 3:1, 4:1, 5:1, 6:1, 7:1, 8:1, 9:1, or 10:1.

In some embodiments, the skin biopsies were obtained from previously published XLRP patients and unaffected individuals after written informed consent. All procedures followed the Declaration of Helsinki and approved by the Institutional Review Board of the University of Pennsylvania and UMass Medical School.

The plasmids encoding human $RPGR^{ORF15}$ or $RPGR^{ex1-19}$ have been described (50, 51). Antibody details are provided in Table 1.

The biopsies were dissociated as previously described to obtain primary fibroblasts 1. Briefly, skin biopsies were washed in Iodine followed by 3 washes in PBS (Invitrogen). The sample was minced with a sharp scalpel in a culture plate and incubated with Dulbecco's modified Eagle's medium DMEM/F12 (Invitrogen) supplemented with 20% FBS (Sigma-Aldrich, Saint-Louis, MO, USA), penicillin, and streptomycin at 37° C. in a humidified 5% CO2 incubator. Ten days after harvesting, the skin was removed, and fibroblasts were passaged for storage and analysis. After dissociation, cells were grown in DMEM/F12 media containing 10% fetal bovine serum at 37° C. and 5% CO2 incubator. All analyses were done in the fibroblasts at the same passage stages.

Plasmid DNA transfections was performed using FuGENE 6 (Promega) according to the manufacturer's protocol. All Dicer substrate siRNAs (dsiRNAs $RPGR^{ex1-19}$, positive, and negative controls, see Table 2) were designed and purchased from Integrated DNA technology (IDT) and transfected at 20 nM using Lipofectamine RNAiMAX Reagent (Thermo Fisher Scientific), per manufacturer's instructions. Cells were plated and transfected 24 h later at 50-70% confluency and induced to form primary cilia 24 hours post transfection by serum starvation for 24 hours.

Total RNAs were isolated with QIAzol Lysis reagent (Qiagen) and precipitated according to the manufacturer's instructions. Reverse transcription was performed with 1 µg of total RNAs with the SuperScript™ First-Strand Synthesis System for RT-PCR (Invitrogen). The resulting cDNA was used to perform gene expression analysis using the Biorad CFX96 qPCR instrument and Power SYBR Green PCR Master Mix (Thermo Fisher Scientific). The isoform-specific qPCR primers are described in Table 2.

mRNA decay after transcriptional inhibition with Actinomycin-D treatment was performed as previously described (55). Briefly, the fibroblasts were plated at 50% confluency in 6-well plates. 24 hours later, cells were treated with 10 µg/ml actinomycin D (Sigma-Aldrich) in DMEM/F12 media for 1, 2, 4, 6 and 8 hours. Total mRNA was extracted and subjected to RT-qPCR. Experiments were conducted in triplicates and mRNA decay rate was determined by non-linear regression curve fitting (one phase decay) using GraphPad Prism Software.

The cells were lysed on ice in Pierce RIPA Buffer (ThermoScientific) containing Halt™ Protease Inhibitor Cocktail (100×, Thermo Fisher). Lysates were sonicated and centrifugated at 12,000 g for 15 min. Supernatants were quantified and 20 µg of total protein lysate was incubated for 5 min at 95° C. with Laemmli sample buffer. Proteins were separated on a 4-20% Mini-PROTEAN® TGX™ Precast Protein Gel (BioRad) and transferred to a Nitrocellulose membrane (BioRad). The blots were processed using Li-Cor western blotting instructions and blocking, primary and secondary antibodies solution were prepared in Intercept Blocking buffer (Li-Cor). Primary antibodies were incubated overnight at 4° C. and secondary antibodies were incubated at room temperature for two hours (see supplementary table for antibodies details and dilution information). Protein expression was detected using Li-Cor Odyssey Fc detection system and quantified with Image Studio Lite quantification software (Li-Cor).

The primary fibroblasts were plated on coverslips (AmScope CS-R18-100) and fixed in pre-chilled 100% methanol at −20° C. for 5 min or in 4% paraformaldehyde/1×Dulbecco's Phosphate Buffered Saline (DPBS; Potassium chloride 0.2 g/L, Potassium Dihydrogen Phosphate 0.2 g/L, Sodium Chloride 8 g/L, and Disodium Hydrogen Phosphate 1.15 g/L) for 10 minutes, washed 3 times in DPBS and blocked in DPBS containing 5% normal goat serum and 0.5% Triton X100 for 1 hour. Primary antibody solution was prepared in blocking solution and incubated overnight at 4° C. After washing in DPBS, cells were incubated in blocking solution containing Alexa-488-conjugated and Alexa-546-conjugated (Invitrogen) for 1 hour. Finally, cells were washed in DPBS and incubated for 5 minutes with DAPI for nuclear staining. Coverslips were mounted with Antifade Mounting Media (Vectashield) and all images were visualized over 63×objective using a Leica DM6 Thunder microscope with a 16 bit monochrome camera.

Cilia length was measured on single z-stacks using the ImageJ software and line and measure tool. An average of 15 cilia were measured in at least five different coverslip area using acetylated-tubulin or ARL13B ciliary markers. The IMARIS platform was used to process the two channel intensities simultaneously and to measure the degree of overlap of the two channels. After setting intensity threshold, the basal body marker g-tubulin was used to define a region of interest (ROI) and a colocalization channel was built on different z-stacks to obtain the percentage of colocalized signal and intensity. When needed, adjacent optical sections were merged in the z-axis to form a projected image (ImageJ). Colocalization value were plotted using the GraphPad Prism software.

All data are presented as means ±standard derivation from the mean. Two groups comparison was analyzed by Student's t-tests using the Prism GraphPad software. Multiple groups comparison was performed with one-way ANOVA. Differences between groups were considered statistically significant if $p<0.05$. The statistical significance is denoted with asterisks (*$p<0.05$; $p<0.01$; *$p<0.005$, ****$p<0.001$).

EXAMPLES

Figure 2:
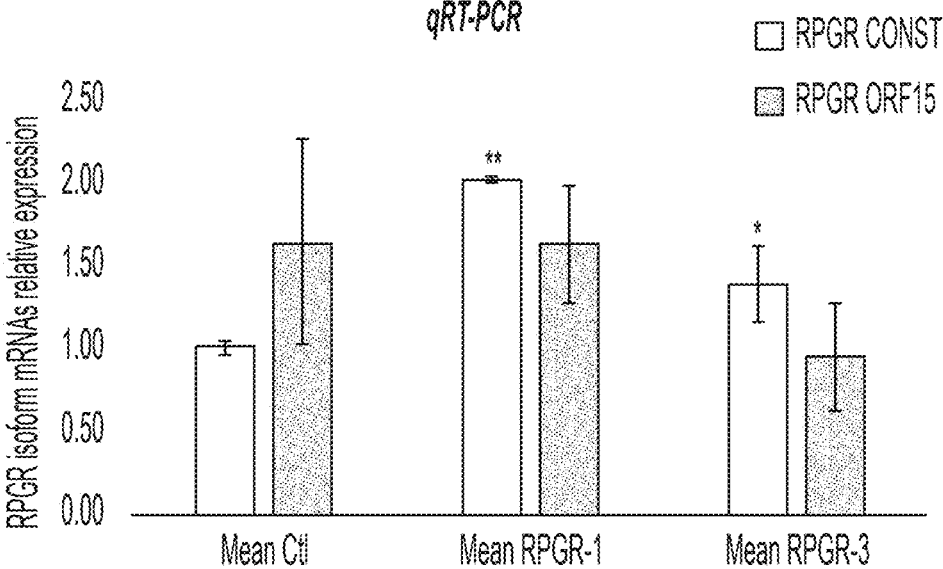
FIG. 2 shows high $RPGR^{CONST}$ mRNA levels in patient-derived organoids. $RPGR^{CONST}$ and $RPGR^{ORF15}$ levels were analyzed for transcript expression by qPCR. Columns from left to right in Mean Ctl (columns 1-2 overall): $RPGR^{CONST}$; and $RPGR^{ORF15}$ Columns from left to right in Mean RPGR-1 (columns 3-4 overall): $RPGR^{CONST}$; and $RPGR^{ORF15}$ Columns from left to right in Mean RPGR-3 (columns 5-6 overall): $RPGR^{CONST}$; and $RPGR^{ORF15}$.
Figure 3A:
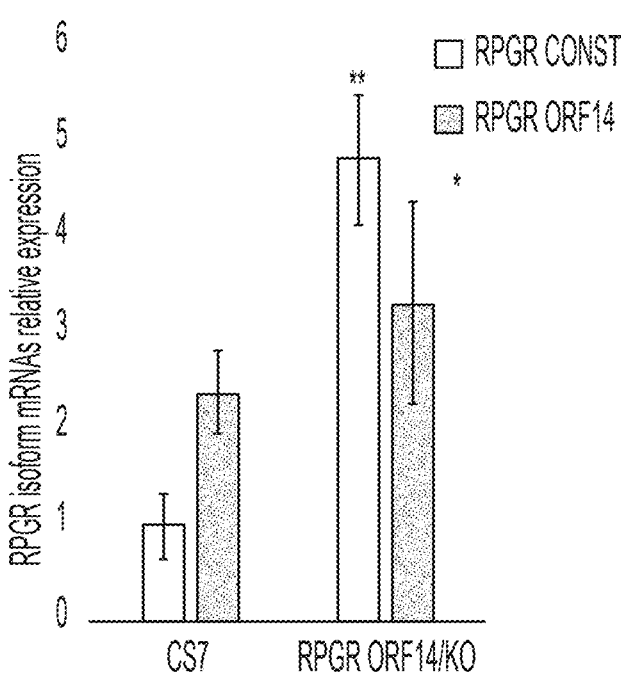
FIGS. 3A-3C show an $RPGR^{ORF14/KO}$ mouse model shows higher $RPGR^{CONST}$ expression. $RPGR^{CONST}$ and $RPGR^{ORF14}$ levels were analyzed for transcript and protein expression by qPCR (FIG. 3A) and western blot (FIGS. 3B-3C). *p<0.05%, **p<0.01.
Figure 3B:
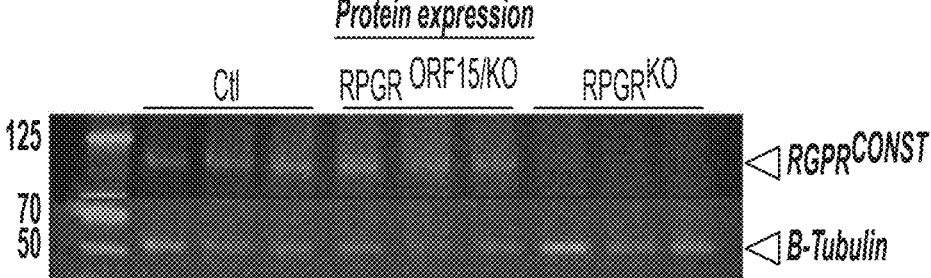
Figure 3C:
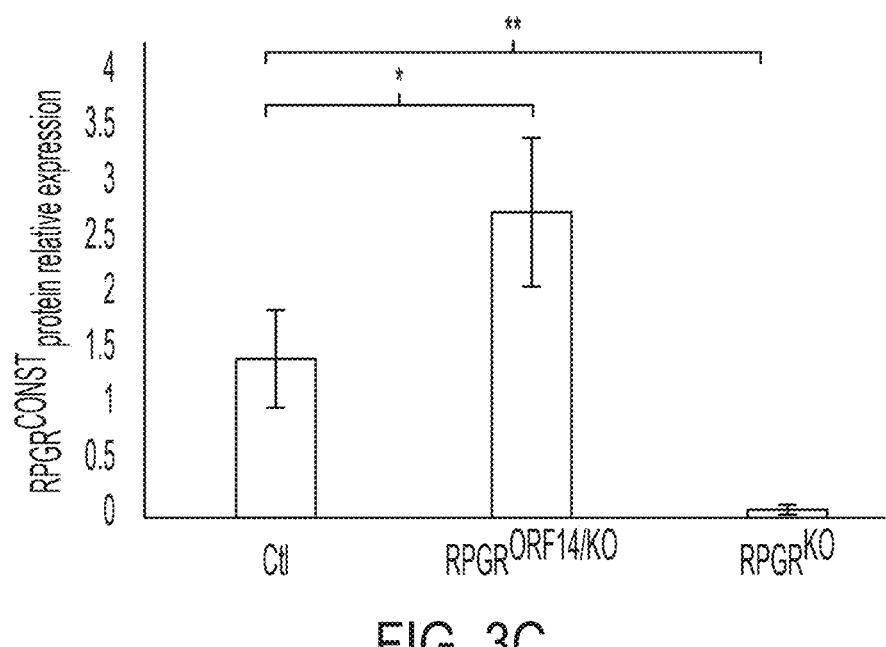
Figure 4A:
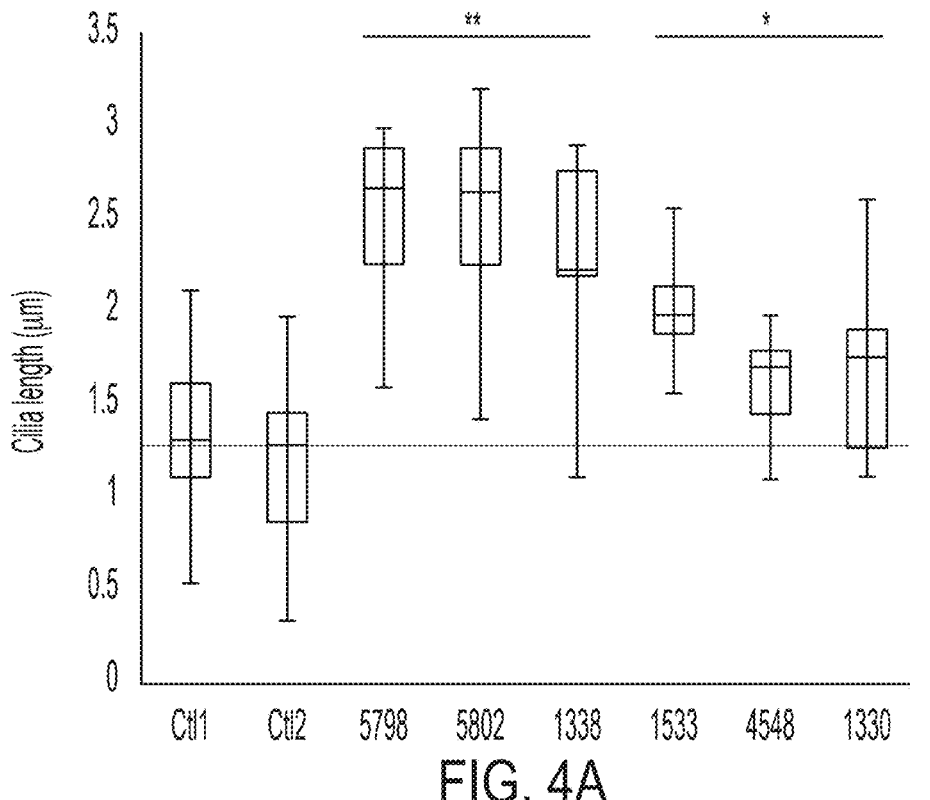
FIGS. 4A-4B show mutations in ORF15 increase cilia length in primary human fibroblasts. Cilia were stained with acetylated tubulin antibody and visualized by immunofluorescence microscopy (FIG. 4A). Cilia length was calculated using ImageJ software. Cilia length was correlated to $RPGR^{1-19}$ ($RPGR^{CONST}$) relative expression in primary fibroblasts (FIG. 4B). Patient fibroblasts with higher to $RPGR^{CONST}$ levels shows increase in primary cilia length. *p<0.05, **p<0.01.
Figure 4B:
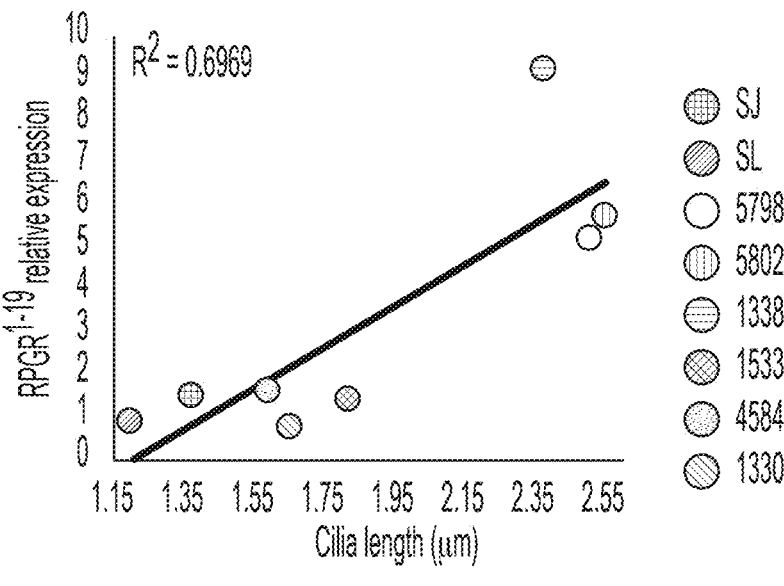
Figure 5:
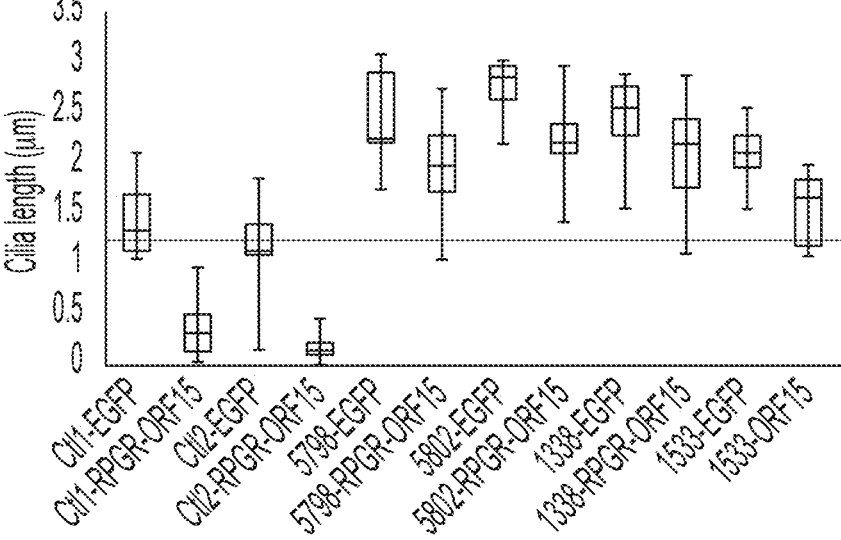
FIG. 5 shows mimicking RPGR gene therapy does not rescue cilia length defects in $RPGR^{ORF15}$/KO primary fibroblast. Cells were transfected with negative-control EGFP or $RPGR^{ORF15}$ encoding plasmids. Cilia were stained with acetylated tubulin antibody and visualized by immunofluorescence microscopy. Cilia length was measured using ImageJ software. $RPGR^{ORF15}$ overexpression shows strong inhibition in cilia growth. Primary fibroblast expressing high $RPGR^{CONST}$ does not shows significant rescue in cilia length.
Figures 6A, 6B:
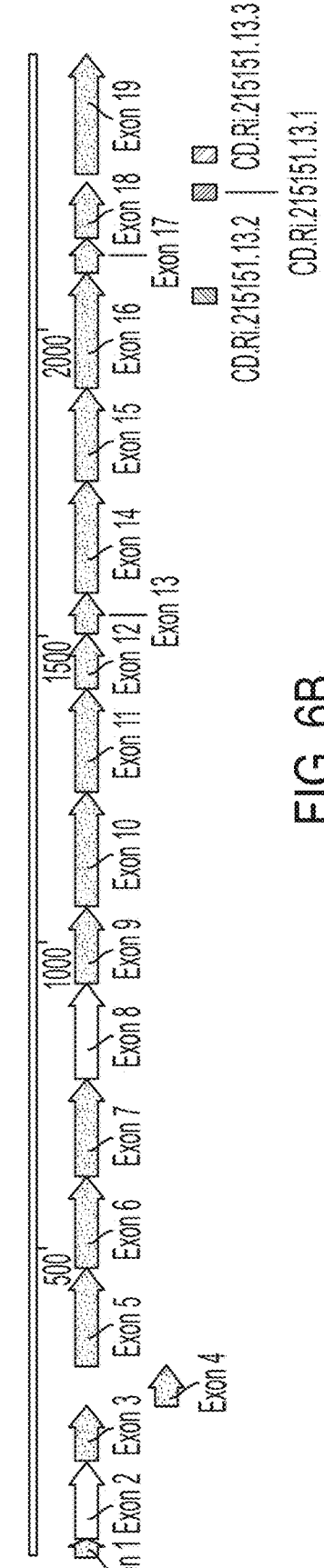
FIGS. 6A-6D show targeting $RPGR^{CONST}$ isoform in $RPGR^{ORF15}$ primary fibroblasts. DsiRNA sequences (FIG.
Figures 6C, 6D:
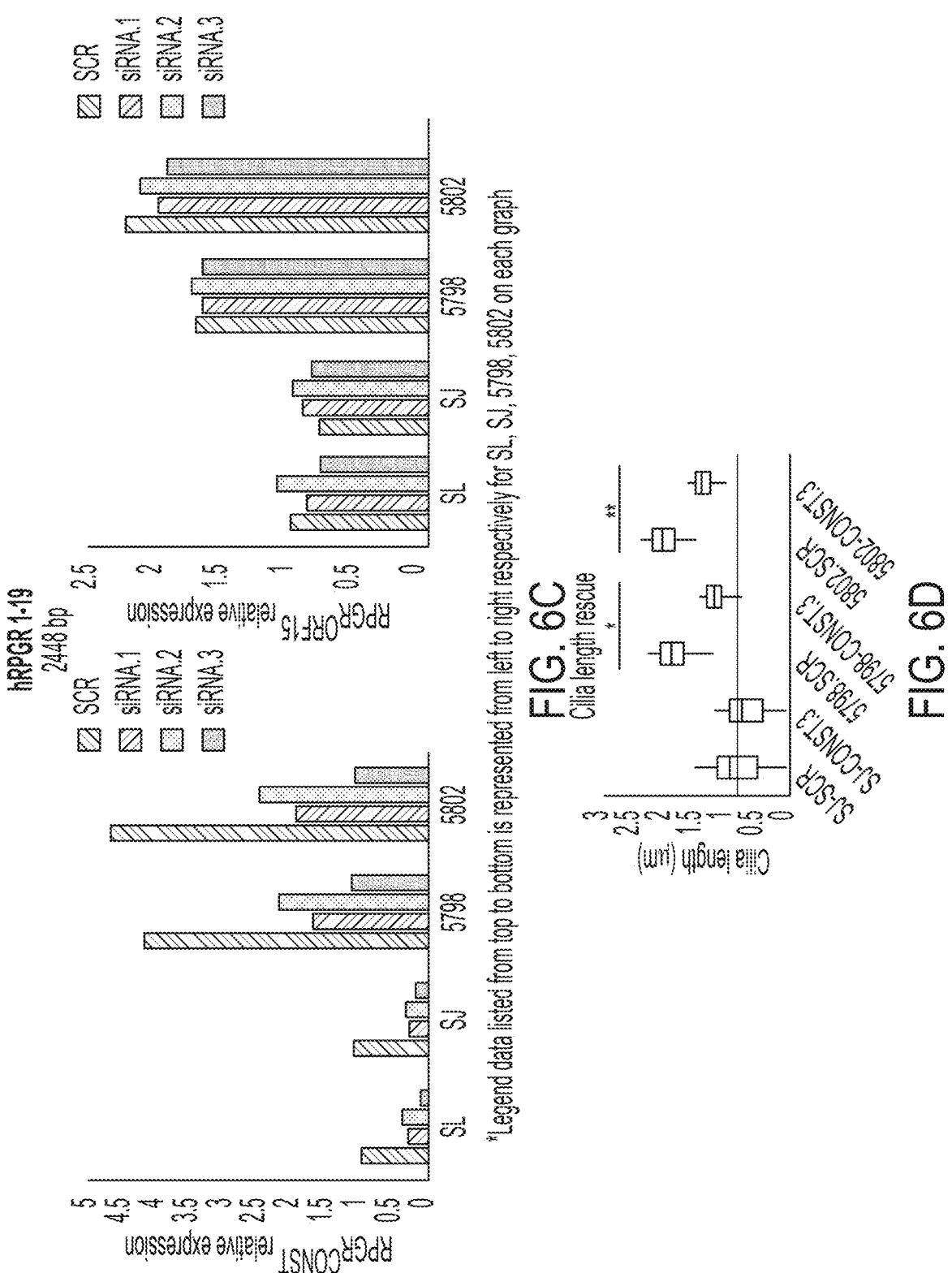
Figures 7A, 7B:
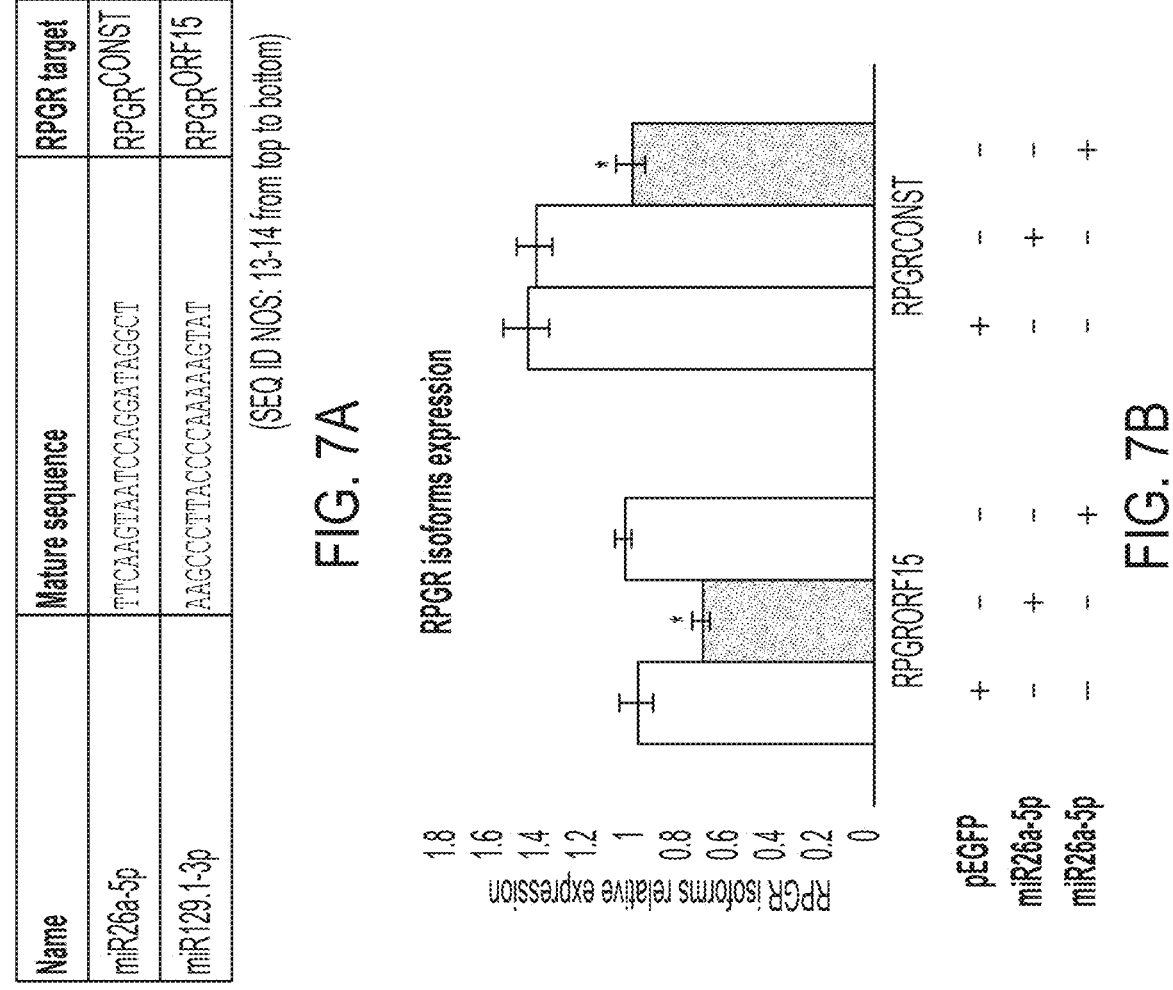
Figure 7C:
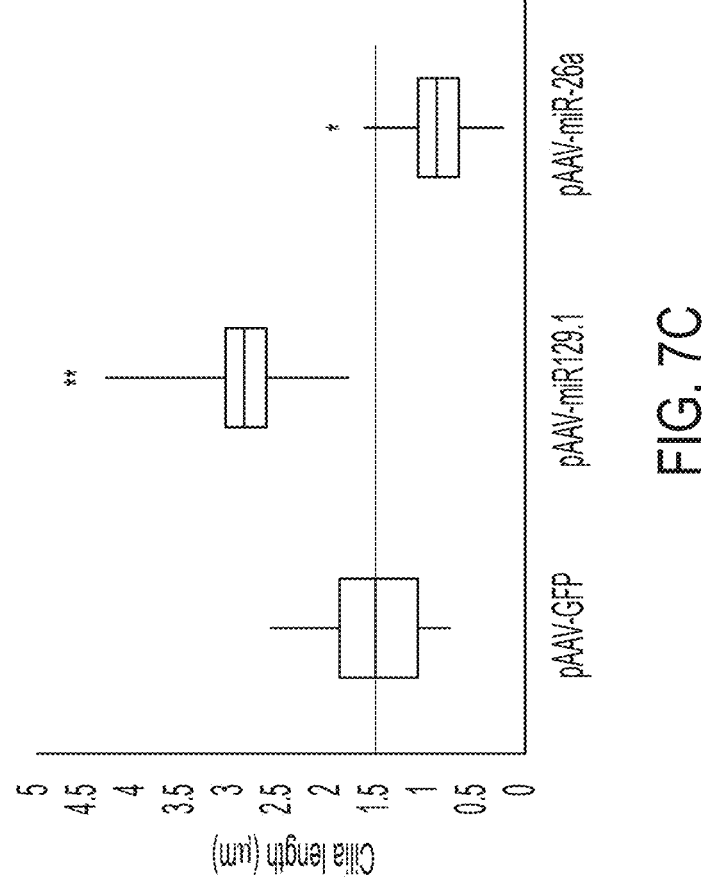

Example 1: Modulation of $RPGR^{CONST}$ and $RPGR^{ORF15}$ Affect Cilia Length It was observed that some $RPGR^{ORF15}$ mutations lead to an increase in the $RPGR^{CONST}$ levels in patient fibroblasts (FIGS. 1A-1C), patient-derived retinal organoids (FIGS. 2A-2B), and in RpgrORF14-ko mouse retina (FIGS. 3A-3C). Increase in the levels of both isoforms was observed in the mutant fibroblasts as compared to controls. This increase was likely due to a positive feedback effect on overall RPGR gene transcription. The increase in $RPGR^{CONST}$ levels was correlated with ciliary elongation whereas $RPGR^{ORF15}$ overexpression reduced cilia length (FIGS. 4A-4B). It was also found that the $RPGR^{ORF15}$ gene augmentation did not completely rescue the cilia length in the mutant fibroblasts (FIG. 5) and depended upon the $RPGR^{CONST}$ levels and ciliary elongation in the mutant fibroblasts. Further, $RPGR^{ORF15}$ overexpression can be toxic to cells; hence, regulated $RPGR^{ORF15}$ gene. siRNA-mediated knockdown of the $RPGR^{CONST}$ isoform rescued the cilia length defect in patient fibroblasts. As shown in FIGS. 6A-6B, 3 siRNAs were designed that specifically target the human $RPGR^{CONST}$ isoform and one scrambled negative control siRNA. These siRNAs knocked down the levels of RPGR$^{CONST}$, but not of RPGR$^{ORF15}$ (FIG. 6C). siRNA.3 showed maximum efficiency in knocking down the RPGR$^{CONST}$ isoform. siRNA.3 was used as a therapeutic agent to test cilia length rescue in the patient fibroblasts. As shown in FIG. 6D, siRNA.3 rescued the cilia length to almost normal levels in the mutant fibroblasts, but did not affect the cilia length of control fibroblasts. miRNAs, miR-261-5p and miR-129.1-3p, were also identified (FIG. 7A), that can specifically target RPGR$^{CONST}$ and RPGR$^{ORF15}$, respectively (FIG. 7B). Consistently, overexpressing miR129.1-3p resulted in elongation of cilia length whereas overexpression of miR26a-5p reduces cilia length (FIG. 7C).

Figures 8C, 8D:
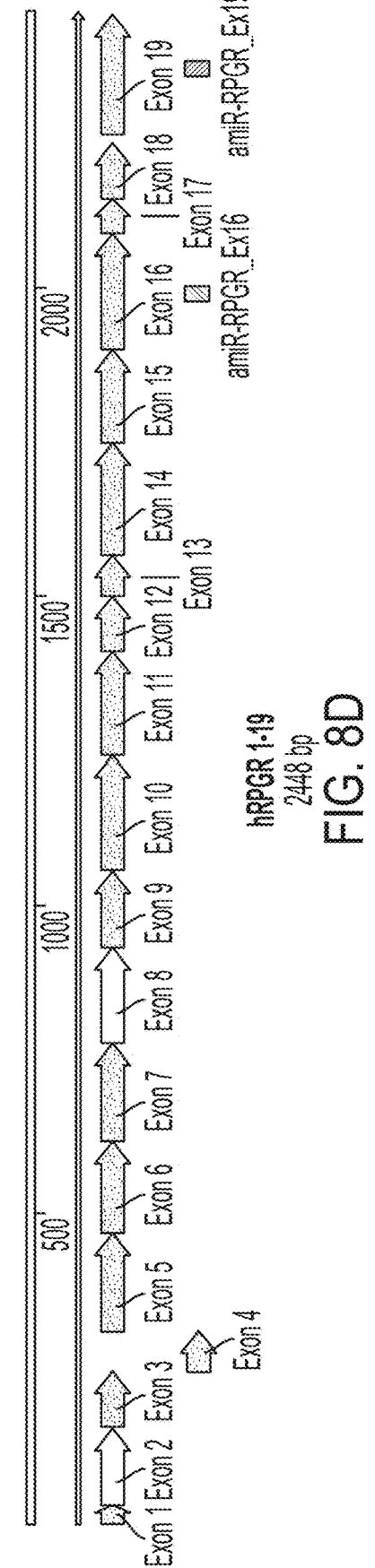

FIGS. 8A-8D show data relating to targeting RPGR isoforms using artificial miRNAs. FIG. 8A shows artificial miRNAs sequences based on has-miR155 backbone and targeting RPGR$^{CONST}$ isoform. Nucleotides shaded in top strand represent the amiRNA leader sequence complementary to RPGR$^{CONST}$. Nucleotides in bold corresponds to the 2nt-bulge. Nucleotides shaded on bottom strand represent the amiRNA passenger sequence complementary to the leader sequence. FIGS. 8B and 8C show the secondary structure of the pre-artificial miRNAs. FIG. 8D shows a schematic localization of the amiRNAs targeting sequences.

Example 2: RPGR Isoform Imbalance Causes Ciliary Defects Due to Exon $^{ORF15}$ Mutations in X-Linked Retinitis Pigmentosa (XLRP)

Fibroblast samples were analyzed from eight patients and found that all of them form longer cilia than normal controls, albeit to different degrees. Although all mutant RPGR$^{ORF15}$ messenger RNA (mRNA) are unstable, their steady-state levels were similar or higher than those in the control cells, suggesting there may be increased transcription. Three of the fibroblasts that had higher levels of mutant RPGR$^{ORF15}$ mRNA also exhibited significantly higher levels of RPGR$^{ex1-19}$ mRNA. Four samples with unaltered RPGR$^{ex1-19}$ levels carried mutations in RPGR$^{ORF15}$ that resulted in this isoform being relatively less stable. Thus, in all cases, the RPGR$^{ex1-19}$/RPGR$^{ORF15}$ isoform ratio was increased, and this was highly correlative to the cilia extension defect.

Moreover, overexpression of RPGR$^{ex1-19}$ (mimicking the increase in RPGR$^{ex1-19}$ to RPGR$^{ORF15}$ isoform ratio) or RPGR$^{ORF15}$ (mimicking reduction of the ratio) resulted in significantly longer or shorter cilia, respectively. Notably, the cilia length defect appears to be attributable to both the loss of the wild-type RPGR$^{ORF15}$ protein and to the higher levels of the RPGR$^{ex1-19}$ isoform, indicating that the observed defect is due to the altered isoform ratios. These results suggest that maintaining the optimal RPGRex1-9 to RPGR$^{ORF15}$ ratio is critical for cilia growth and that designing strategies that focus on the best ways to restore the RPGR$^{ex1-19}$/RPGR$^{ORF15}$ ratio may lead to better therapeutic outcomes.

Primary cilia are evolutionarily conserved microtubule-based non-motile protrusions of the plasma membrane of most vertebrate cell types (1). They are nucleated from the basal bodies (mother centrioles) that dock at the apical plasma membrane in quiescent cells. The proximal region of the cilia, also called transition zone, acts as a gate. The microtubules further extend to form a distal axoneme surrounded by the ciliary membrane. The primary cilium regulates critical developmental and homeostatic signaling cascades by targeting several integral and peripheral membrane proteins as well as soluble moieties along the axoneme via a conserved mechanism termed intraflagellar transport (IFT) (2, 3). The trafficking is also regulated by macromolecular complexes of several proteins including RPGR (retinitis pigmentosa GTPase regulator), CEP290 (centrosomal protein 290 kDa), CP110 (centrosomal protein 110 kDa), Usher Syndrome proteins, and Bardet Biedl Syndrome proteins (4, 5). Mutations in these proteins are associated with severe developmental and homeostatic disorders collectively termed ciliopathies (6). These include Meckel-Gruber Syndrome, Joubert Syndrome, Senior-Loken Syndrome, Usher Syndrome, and some forms of non-syndromic photoreceptor degenerations. Photoreceptors (rods and cones) have a modified sensory cilium in the form of the light-sensing outer segment. The photoreceptors are one of the highly metabolically active cell types in the body. They depend upon stringently controlled proteins and lipid trafficking from their site of synthesis in the inner segment to the outer segment for light detection (7). Perturbations in the trafficking machinery due to functional deficits in ciliary proteins lead to severe photoreceptor degeneration (2, 3, 8). One such ciliary trafficking regulator is RPGR (retinitis pigmentosa GTPase regulator).

Mutations in RPGR are associated with X-linked forms of retinitis pigmentosa (RP), a debilitating blindness characterized by severe and progressive photoreceptor degeneration (9-12). RPGR mutations account for the majority (~70%) of XLRP cases and 12-15% of simplex RP, with no family history (12-14). Additionally, RPGR mutations are associated with cone-rod degeneration, macular dystrophy, and extra-ocular presentations, such as sperm abnormalities, hearing defects and primary cilia dyskinesia (15-19). Overall, RPGR mutations are a leading cause of blindness accounting for almost 20% of all RP cases.

The RPGR gene encodes two major alternatively spliced isoforms: RPGR$^{ex1-19}$ (19 exons) and RPGR$^{ORF15}$ (terminating in intron 15; exon $^{ORF15}$) (20-23). The terminal exon 19 of the RPGR$^{ex1-19}$ isoform carries an isoprenylation signal involved in its localization to cilia (24, 25). Exon $^{ORF15}$ of the RPGR$^{ORF15}$ isoform contains purine-rich repeats that encode for a glutamic acid and glycine rich domain (26). Since majority of RPGR mutations are located in exon $^{ORF15}$, the RPGR$^{ORF15}$ isoform has been considered the major disease-associated isoform in humans (26). The great majority of exon $^{ORF15}$ mutations are predicted to prematurely truncate the RPGR$^{ORF15}$ protein.

Both RPGR isoforms are expressed throughout the body but are particularly abundant in the retina. Previous studies have identified mouse and canine models of RPGR mutations and have suggested the involvement of RPGR in regulating ciliary trafficking by acting as a gate-keeper at the transition zone (27-31). Loss of RPGR alters protein trafficking to the photoreceptor outer segment but permits its initial generation. RPGR depletion alters cilia length in cultured cell lines and fibroblasts (32). However, the effect on the ciliary defects of different RPGR$^{ORF15}$ mutations is unclear.

To investigate the effect of the human disease-causing mutations in RPGR$^{ORF15}$ on its expression and on cilia formation, RPGR isoform expression, cilia formation, and ciliary protein trafficking was analyzed in patient-derived cells. Studies unravel a new potential pathogenic mechanism of RPGR$^{ORF15}$-disease, which may assist in developing new therapies for these conditions.

Ciliary Defects in RPGR$^{ORF15}$-Mutant Fibroblasts

Given that RPGR regulates cilia length (32), cilia formation was examined in the patient and control fibroblasts. Primary fibroblasts from skin biopsy specimens from eight male RPGR$^{ORF15}$ patients (RPGR-1, RPGR-2, RPGR-3, RPGR-4, RPGR-5, RPGR-6, RPGR-7, and RPGR-8) with frameshift and truncation mutations in exon $^{ORF15}$ (FIGS. 9A-9B) were generated. The patients were all from families previously confirmed to have X-linked RP due to RPGR$^{ORF15}$ mutations (33, 34); their ages at skin biopsy ranged from 21 to 66 years. The patients had ophthalmoscopic features of pigmentary retinopathy, abnormal visual fields and reduced or non-detectable electroretinograms (33, 34). Since the control samples from the same family members could not be obtained, six random asymptomatic control samples were included without RPGR mutations (CTL-1, CTL-2, CTL-3, CTL-4, CTL-5, and CTL-6).

Figure 10B:
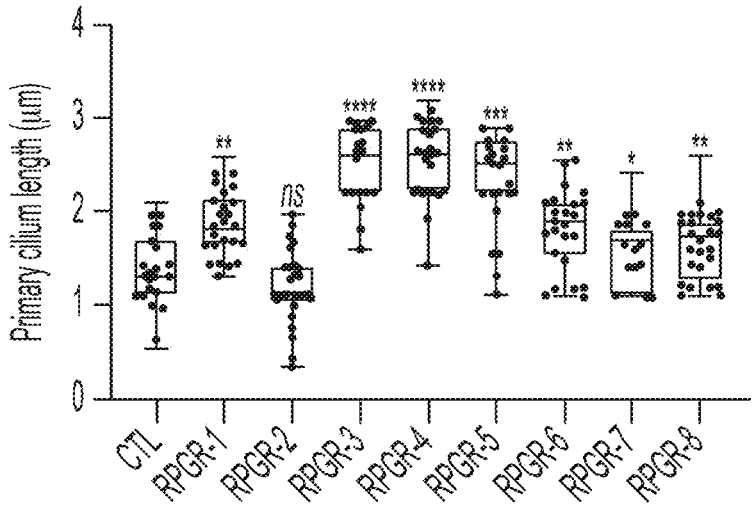

While the control and RPGR-2 fibroblasts grew cilia in the range of 1 μm-1.5 μm, two groups of mutations with longer cilia: Cilia were elongated to a range of 2.5 μm-3.5 μm range in the RPGR-1, RPGR-3, RPGR-4, and RPGR-5 fibroblasts and to a lesser extent (1.8 μm-2.5 μm) in RPGR-6, RPGR-7, and RPGR-8 (FIGS. 10A-10B) were detected. As predicted, an effect on the number of ciliated cells was not detected.

Correlation of Cilia Length to RPGR Isoform Levels in Fibroblasts

Figure 11A:
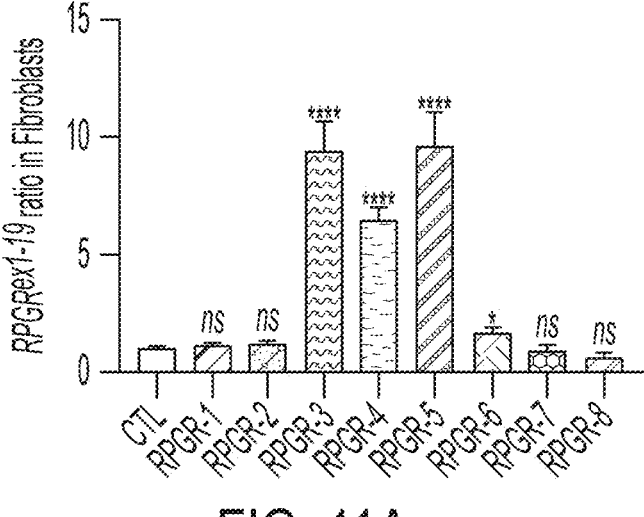
FIGS. 11A-11D show RPGR isoform levels in patient-derived fibroblasts.
Figure 11B:
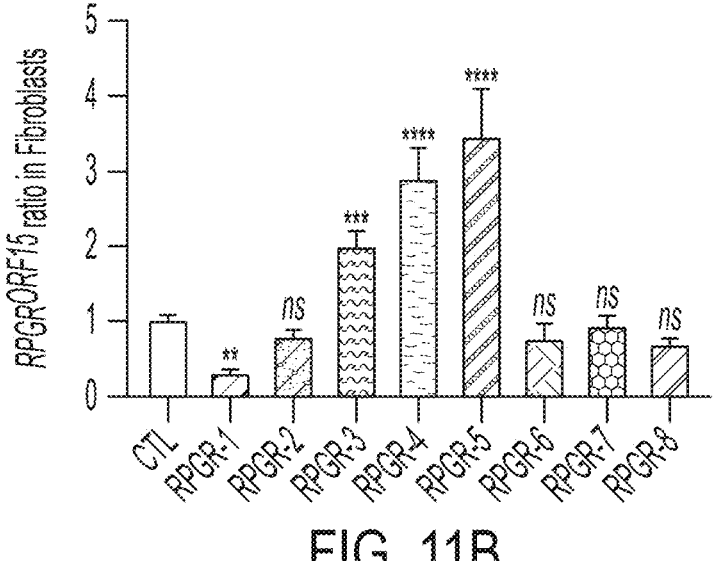

It was then observed whether ciliary phenotype was associated with an effect of exon $^{ORF15}$ mutations on RPGR expression. To this end, quantitative RT-PCR analysis of the two major isoforms was performed. Significantly higher levels (8-10 fold) of the RPGRex1 19 isoform were found in RPGR-3, RPGR-4, and RPGR-5 fibroblasts samples when compared to the other RPGR mutants or the control fibroblasts (FIG. 11A). Higher levels (2-3 fold) of the mutant RPGR$^{ORF15}$ isoform were also detected in RPGR-3, RPGR-4, and RPGR-5. Interestingly, the level of the mutant RPGR$^{ORF15}$ in RPGR-1 was significantly reduced when compared to the controls (FIG. 11B).

Figure 11C:
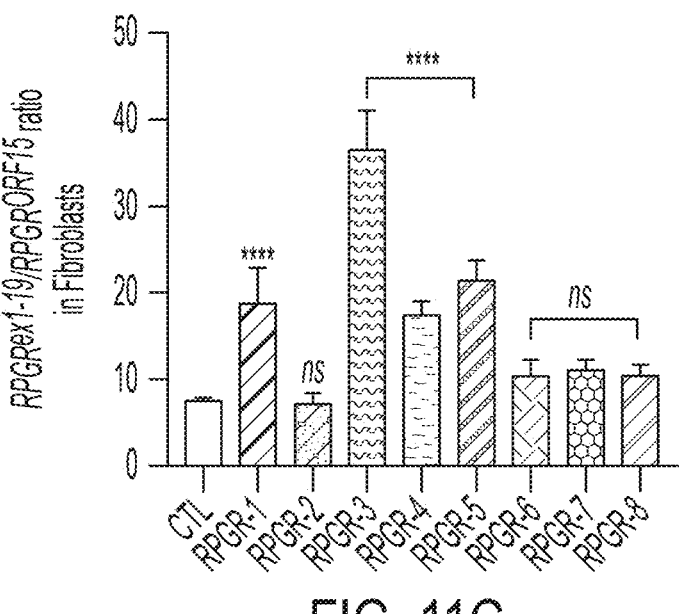
Figure 11D:
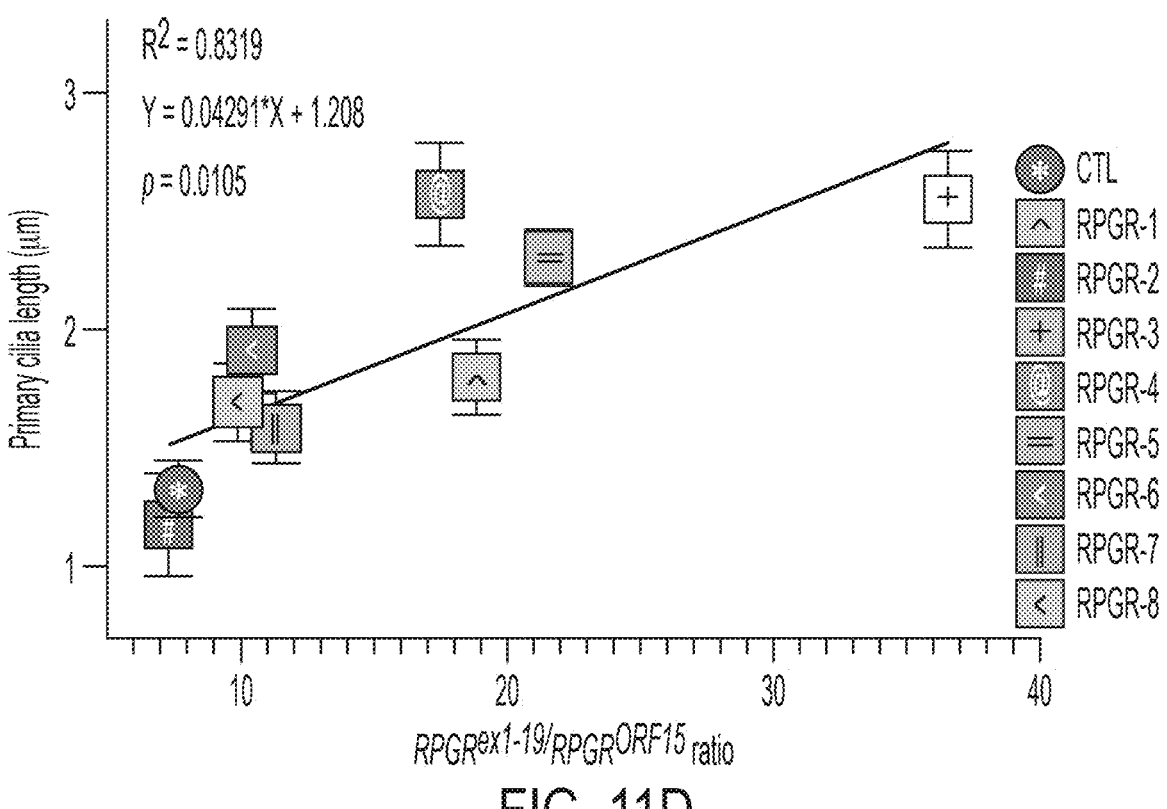
Figure 16A:
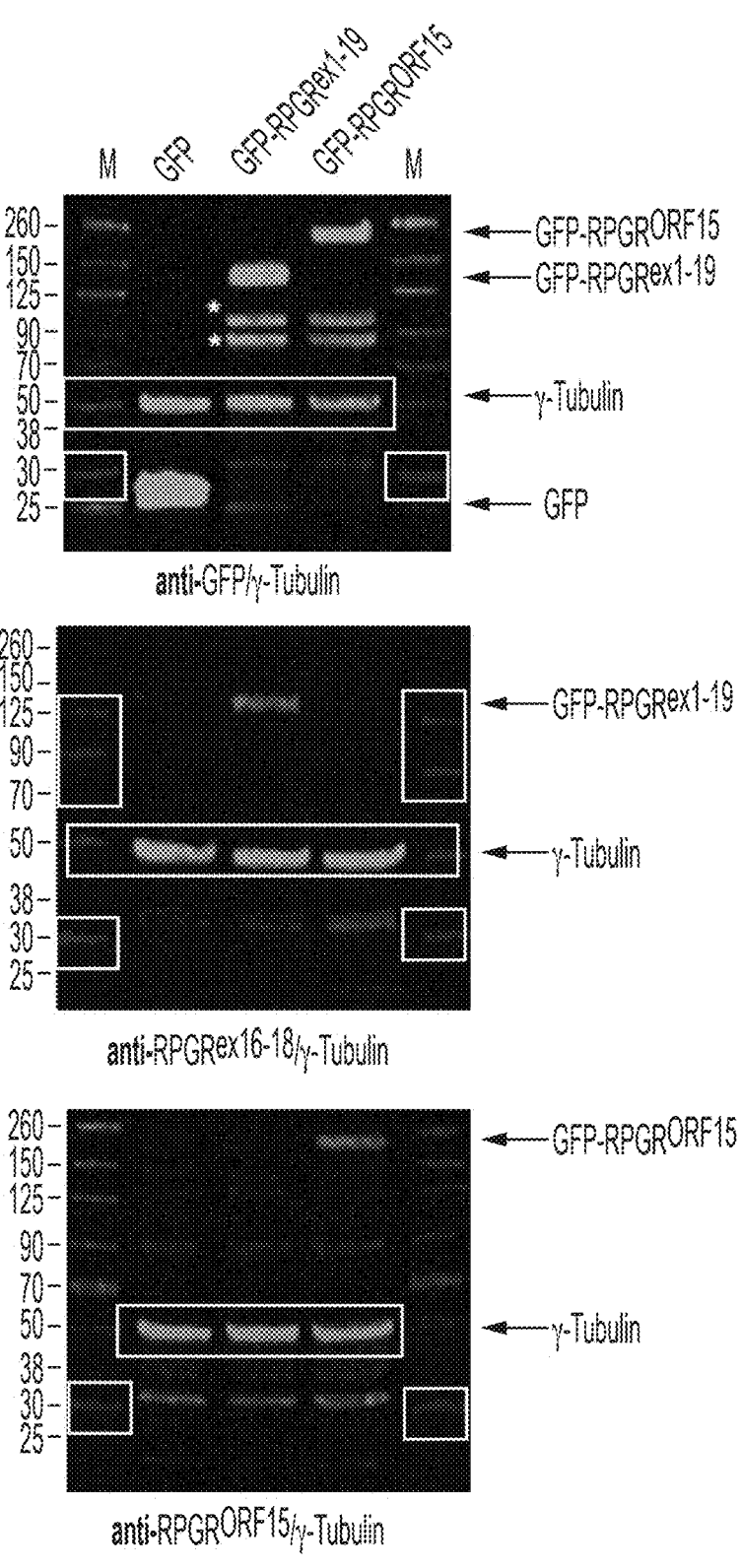
FIG. 16A shows cell extracts from HEK293 cells transiently transfected with plasmids encoding GFP, GFP-RP-GR$^{ORF15}$ or GFP-RPGR$^{ex1-19}$ were analyzed by SDS-PAGE and immunoblotting using indicated antibodies. Green channel indicates the bands obtained using the GFP or RPGR antibodies. Immunoblotting using anti-α-tubulin (outlined by a white rectangle) was used as loading control. M: apparent molecular weight marker (kDa).
Figure 16B:
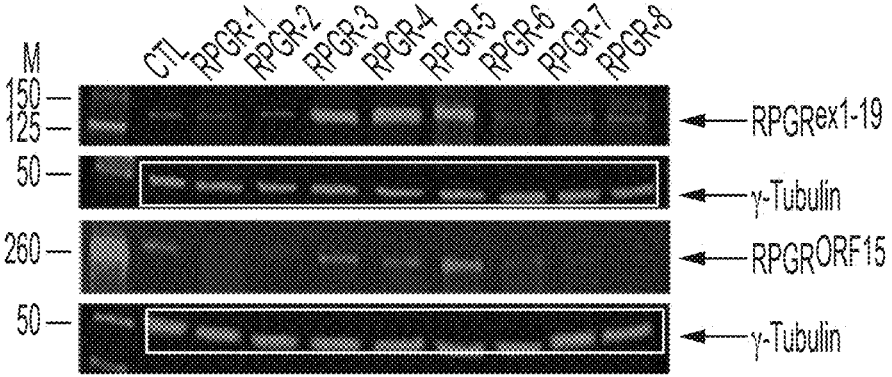
FIG. 16B shows protein extracts (100 μg) of the indicated fibroblasts were analyzed by SDS-PAGE and immunoblotting using RPGR$^{ex1-19}$ or RPGR$^{ORF15}$-specific or α-tubulin (outlined by a white rectangle; loading control) antibodies.
Figure 16C:
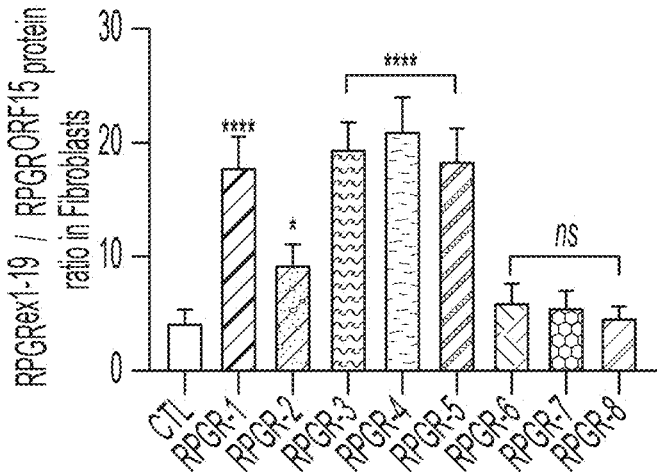
FIG. 16C shows the RPGR$^{ex1-19}$/RPGR$^{ORF15}$ protein ratio was calculated relative to the α-tubulin levels, which were uniform among all samples. Data are mean±SD from three independent experiments (with n>100/experiment).
Figure 17A:
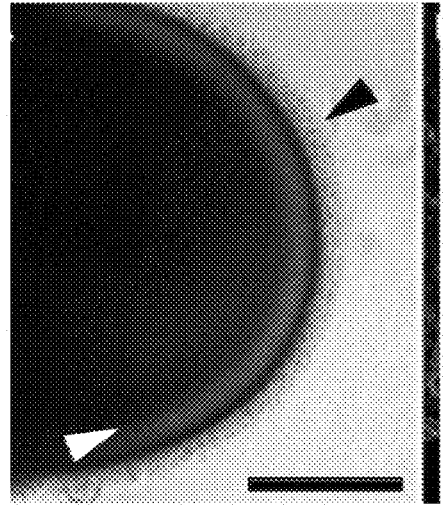
FIG. 17A shows a bright field image of a 22 weeks RPGR-3 PSC-derived retinal organoid, demonstrating retinal layers (white arrowhead) and the presence of a brush border (black arrowhead). Scale bar: 100 μm.
Figure 17B:
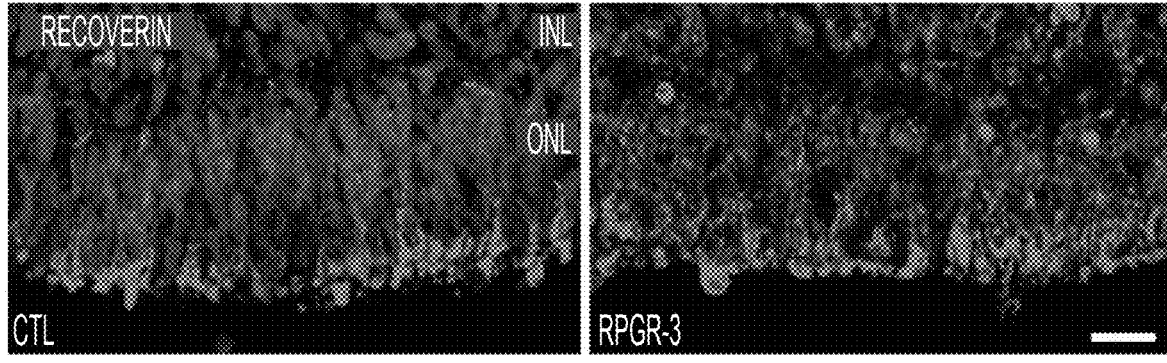
FIG. 17B shows the immunohistochemical staining of control (CTL) and RPGR-3 PSC-derived retinal organoid cryosections at 22 weeks, showing RECOVERIN+(opaque grey) photoreceptors in the outer nuclear-like layer (ONL). DAPI in transparent grey. Scale bar: 15 μm.
Figure 17C:
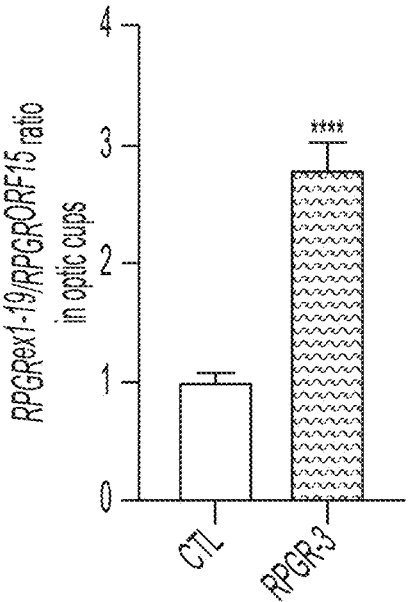
FIG. 17C shows a quantitative RT-PCR analysis of the RPGR isoforms extracted from the control and RPGR-3 was performed. The results show the RPGR$^{ex1-19}$/RPGR$^{ORF15}$ ratio in the RPGR-3 organoids relative to the control (CTL). ONL: outer nuclear layer; INL: inner nuclear layer.

Given that RPGR-1, RPGR-3, RPGR-4, and RPGR-5 also formed relatively longer cilia, it was then tested whether there was a correlation between the RPGR$^{ex1-19}$/RPGR$^{ORF15}$ ratio and the cilia length. While the RPGR-2, RPGR-6, RPGR-7, RPGR-8 and control fibroblasts showed an RPGR$^{ex1-19}$/RPGR$^{ORF15}$ ratio of ~10 fold, in RPGR-1, RPGR-3, RPGR-4, and RPGR-5 fibroblasts there was an increased ratio of between 18 and 35 fold (FIG. 11C). Furthermore, it was found that the length of the cilia was highly correlative to RPGRex1 19/RPGR$^{ORF15}$ ratio, with the coefficient of determination (R2) of ~83% (FIG. 11D). Using RPGR isoform-specific antibodies (FIG. 16A), a significant increase (18-20 fold) in the ratio of the RPGRex1 19/RPGR$^{ORF15}$ protein levels in RPGR-1, RPGR-3, RPGR-4, and RPGR-5 were also detected when compared to other RPGR mutations or controls (FIGS. 16B-16C). It was then checked whether such phenomenon of increased RPGRex1 19/RPGR$^{ORF15}$ ratio is also conserved in retinal microenvironment. Using retinal organoids derived from reprogrammed control and RPGR-3 human induced pluripotent stem cells (iPSCs; FIG. 17A) (West et al. 2020; manuscript submitted), a significant (~2.8 fold) increase was found in the RPGR$^{ex1-19}$/RPGR$^{ORF15}$ ratio in the mutant sample as compared to the controls (FIG. 17C).

Figure 7E:
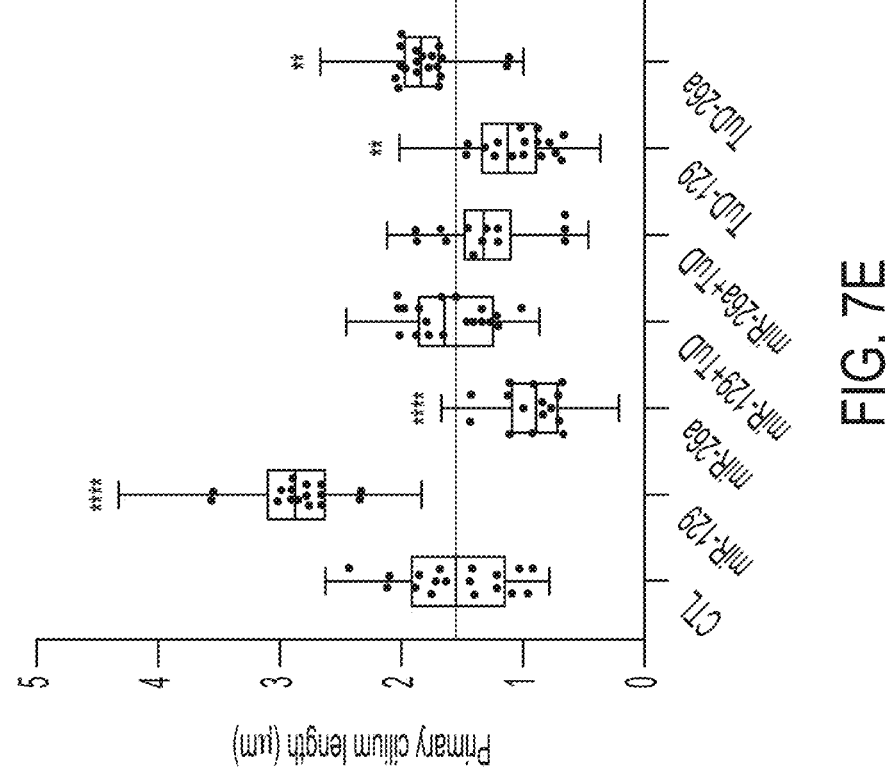

Tough-decoy (TuD) RNA inhibitors were designed against miR-129.1-3p and miR26a-5p and tested their effect on cilia extension. TuDs are efficient anti-miRNA molecules that are used to assess the effect of knocking down the miRNAs of interest. hTERT-RPE1 cells were transiently transfected with plasmids encoding miR-129, miR-26a, miR-129+TuD, miR-26a-Tud, Tud-129 or Tud-26a. The cells were then processed for cilia growth and staining using cilia-specific antibodies. The cilia length was measured using Image J software. As predicted, overexpression of miR-129 leads to increase in the cilia length whereas that of miR-26a results in shorter cilia (****: p<0.0001). Conversely, co-expression of the miRNAs with their cognate TuDs abrogates the cilia length defect due to the miRNAs (FIG. 7E). Moreover, expression of only the TuDs against miR-129 or miR-26a results in shorter and longer cilia, respectively. CTL: control (FIG. 7E).

These results suggest that RPGR$^{ORF15}$ mutations tested in this study affect not only mutant RPGR$^{ORF15}$ expression levels but the RPGRex1 19 isoform levels, albeit to different extents. Although in fibroblast samples from all RPGR patients there was a positive correlation between the RPGRex1 19/RPGR$^{ORF15}$ ratio and cilia length, in RPGR-1, RPGR-3, RPGR-4, and RPGR-5 samples there were distinct effects on the RPGR mRNA levels. The RPGR-1 mutation results in significantly reduced mutant RPGR$^{ORF15}$ expression but does not affect the RPGRex1 19 levels. On the other hand, while the mutant RPGR$^{ORF15}$ is expressed at relatively higher levels in RPGR-3, RPGR-4, and RPGR-5 fibroblast samples, they exhibit significantly higher levels of RPGRex1 19. To further understand the ciliary defects, RPGR-1, RPGR-3, RPGR-4, and RPGR-5 samples were focused on. RPGR-2 was also used, since it showed similar RPGR expression as the control fibroblasts.

Localization of Cilia Length Regulators in RPGR$^{ORF15}$-Mutant Fibroblasts

Figure 12A:
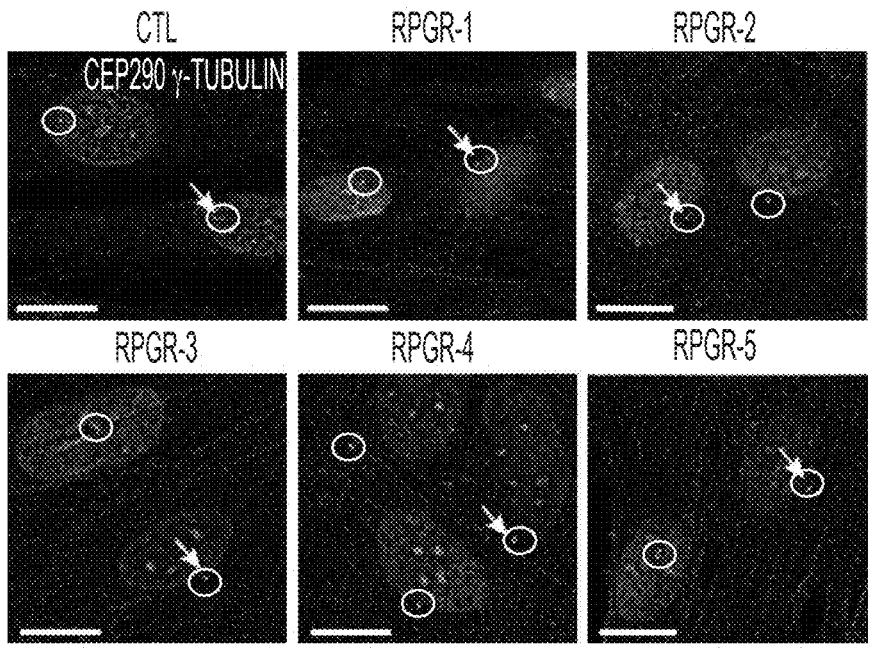
FIGS. 12A-12F show distribution of ciliary markers: CEP290 (FIGS. 12A-12C) and GT335 (FIGS. 12D-12F) staining in the indicated fibroblasts was assessed.
Figures 12B, 12C:
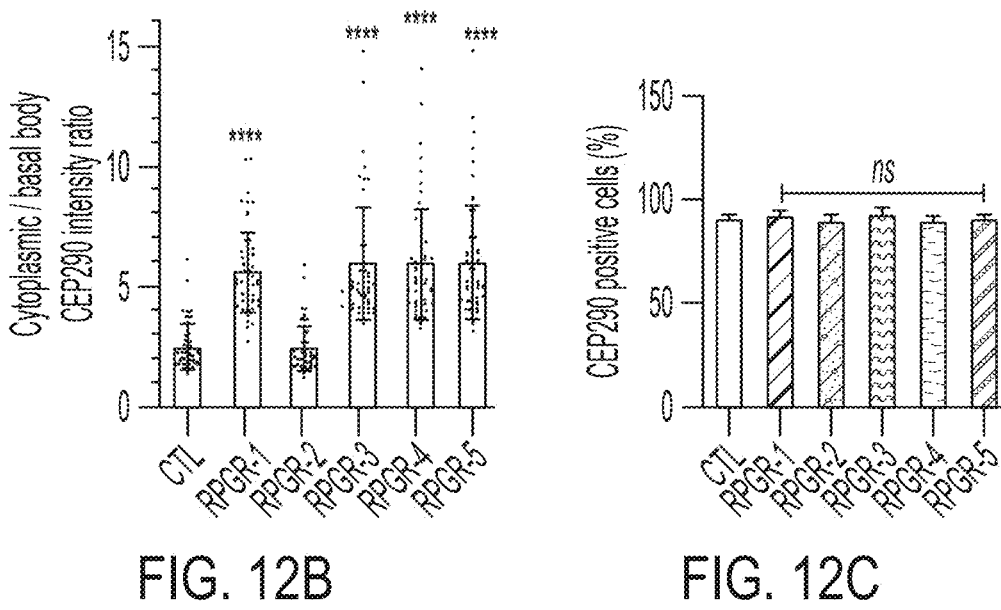

To investigate the ciliary defect in the fibroblasts with elongated cilia, the distribution of ciliary length regulators CEP290 and distribution of glutamylated tubulin were assessed. CEP290 mutations are a frequent cause of Leber congenital amaurosis and syndromic ciliopathies (35-37). Immunofluorescence staining of RPGR-1, RPGR-3, RPGR-4, and RPGR-5 with a previously reported CEP290 antibody demonstrated ~50% reduction in the levels of CEP290 at the basal body (determined by the co-localization with basal body marker α-tubulin) and concomitant increase in the cytosolic CEP290 distribution when compared to RPGR-2 or control fibroblasts (FIGS. 12A-12B). However, the number of CEP290-positive cells was not affected in the mutant as compared to the control fibroblasts (FIG. 12C). These results are consistent with previous studies that demonstrated longer cilia in CEP290-mutant patient fibroblasts and in Cep290-mutant mice (38, 39) and suggest an association between the observed cilia length differences and CEP290 levels in the RPGR-mutant fibroblasts.

Figure 12D:
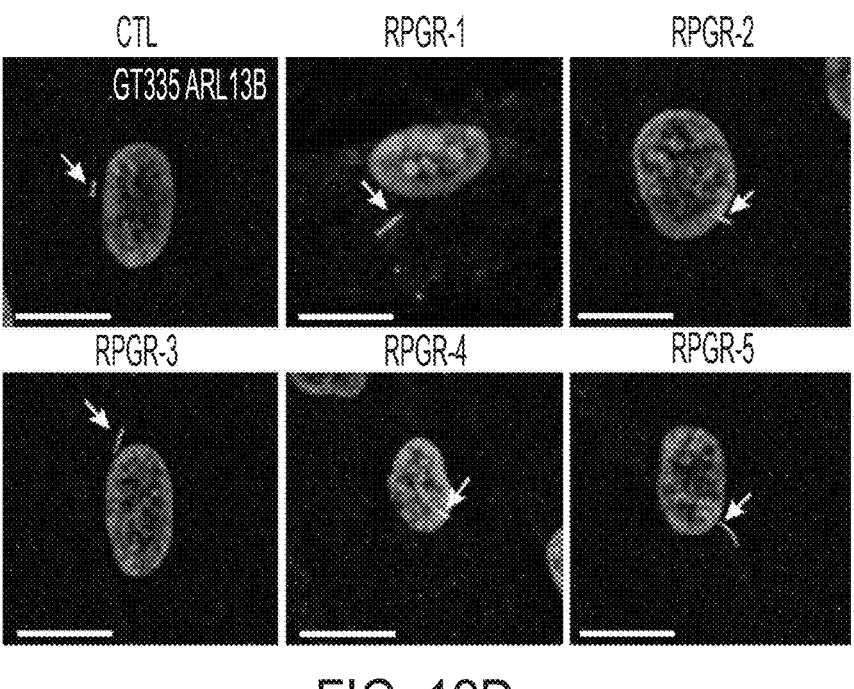
Figure 12E:
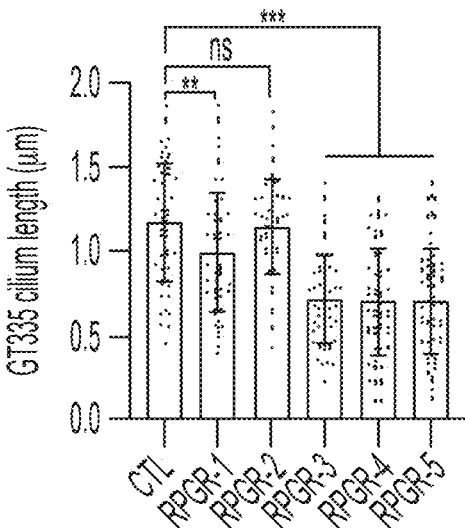
Figure 12F:
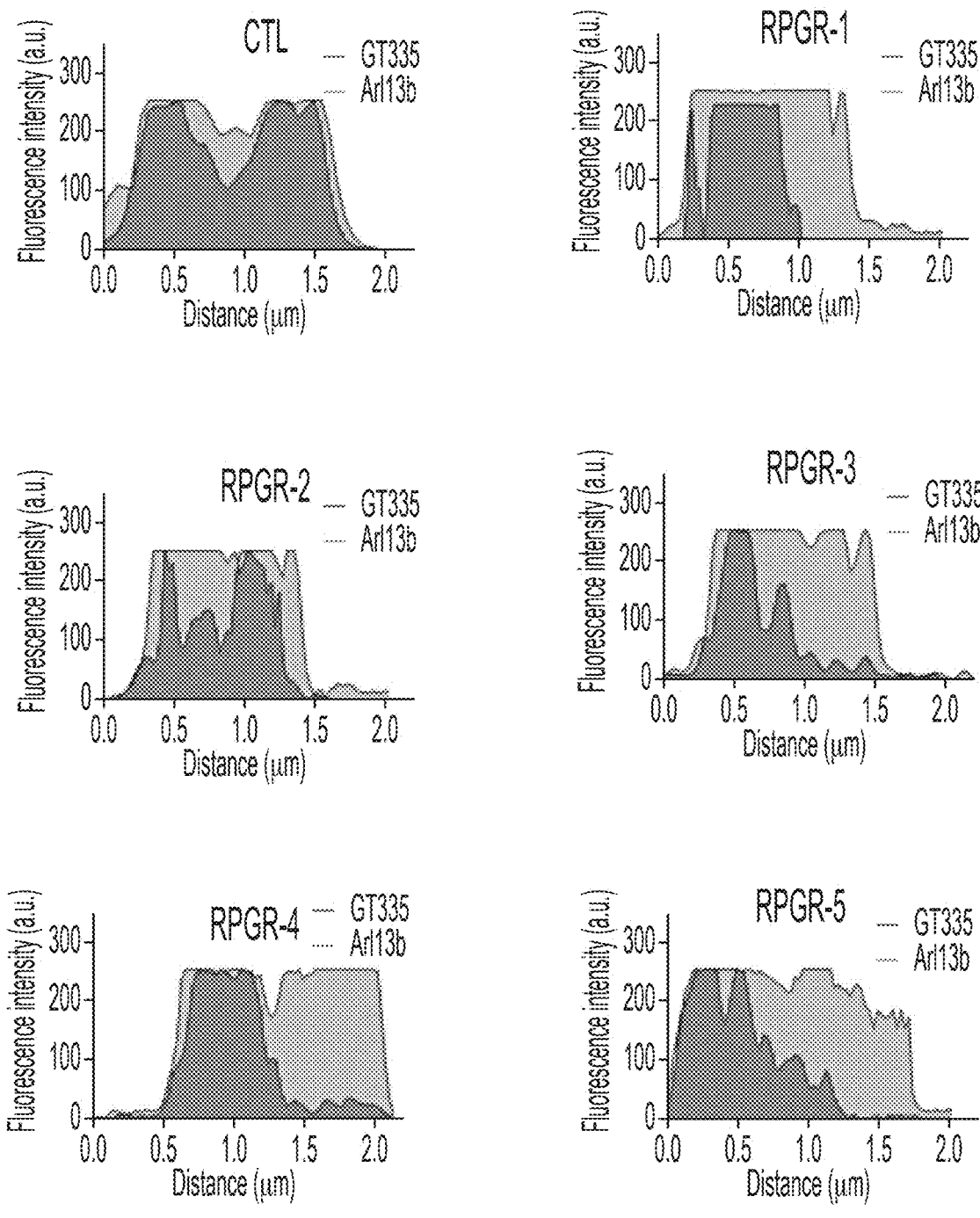

Tubulin polyglutamylation is a modification of the stable ciliary microtubules, which can be detected using the GT335 antibody (40, 41). It was found that the distribution of GT335 was altered in the RPGR$^{ORF15}$-mutant fibroblasts. Immunofluorescence analysis revealed that GT335-immunoreactivity was restricted to the proximal region of the cilia in RPGR-1, RPGR-3, RPGR-4, and RPGR-5 (within ~1.0 μm) (FIGS. 12D-12E) when compared to RPGR-2 and the controls, in which GT335 staining is distributed across the whole cilium (FIG. 12F).

Expression of Wild-Type RPGR$^{ORF15}$ in Mutant Fibroblasts

Figure 13A:
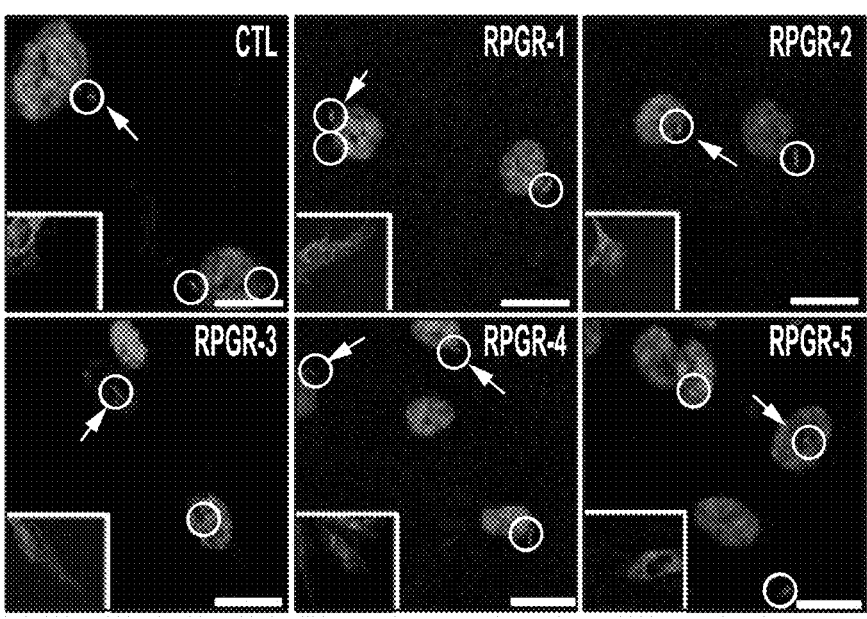
FIGS. 13A-13B show the effect of wild-type RPGR$^{ORF15}$ overexpression on the cilia defect.
Figure 13B:
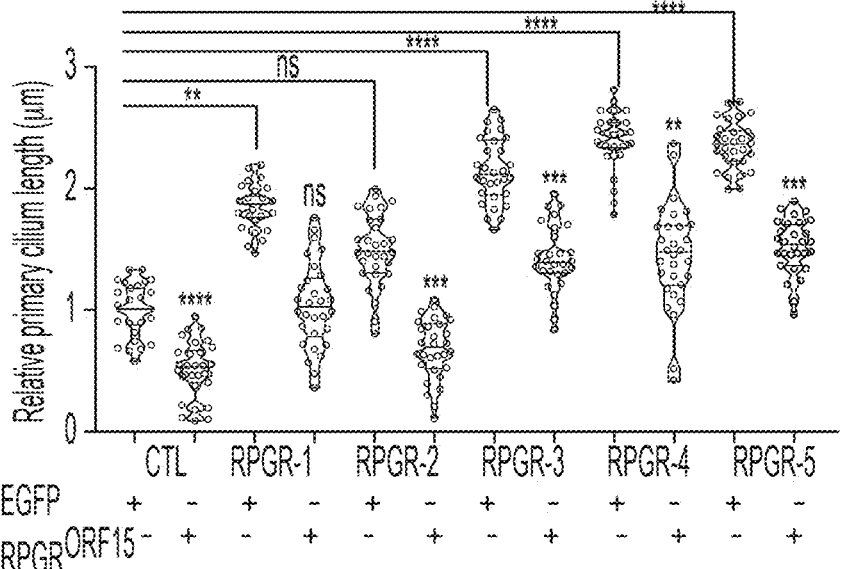

It was then sought to determine whether the observed cilia length defects are due to the lack of the wild-type RPGR$^{ORF15}$ protein. Transfection of the wild-type human GFP-RPGR$^{ORF15}$-encoding cDNA into RPGR-3, RPGR-4, and RPGR-5 did not completely reverse the elongated cilia phenotype when compared to cells transfected with only GFP. While the RPGR-3, RPGR-4, and RPGR-5 fibroblasts transfected with GFP alone formed longer cilia than the CTL (control) fibroblasts, the cilia length reduced from 2.2-2.4 μm to 1.3-1.5 μm after transfection with GFP-RPGR$^{ORF15}$ (FIGS. 13A-13B). RPGR-1, which had relatively modest (~1.8 μm) increase in the cilia length and RPGRex1 19/RP-GR$^{ORF15}$ ratio showed almost complete reversal (~1 μm) of the elongated cilia phenotype upon GFP-RPGR$^{ORF15}$ expression. These data strongly suggest that the normal RPGR$^{ORF15}$ protein function partly contributes to the observed cilia length changes. Samples with relatively higher RPGRex1 19/RPGR$^{ORF15}$ ratio did not show complete reversal of the cilia length phenotype.

Figure 18A:
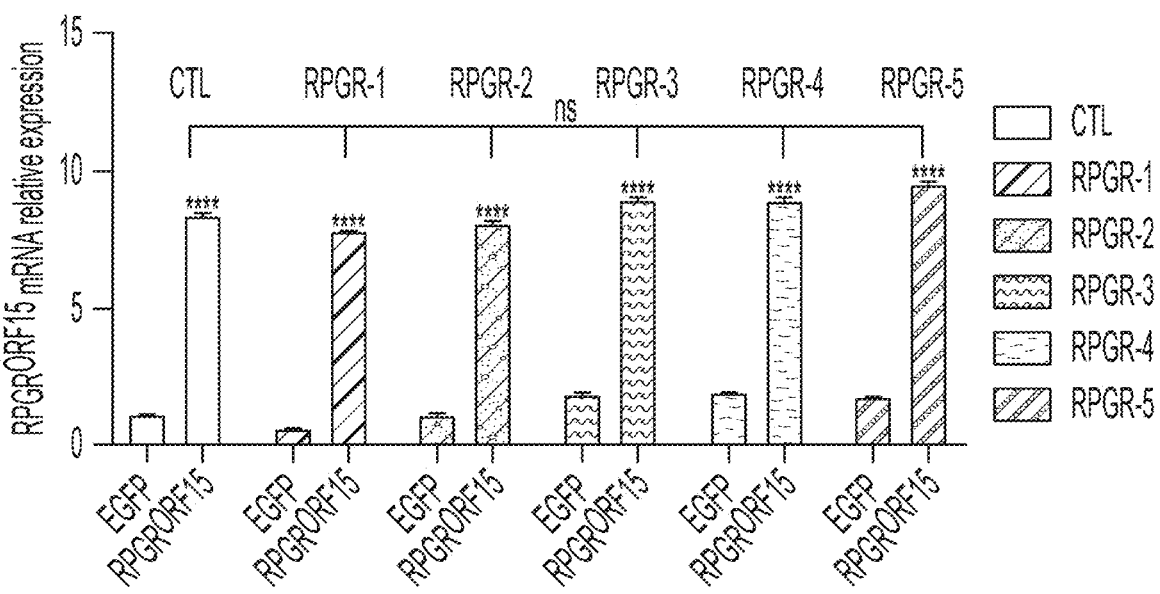
FIGS. 18A-18B shows the expression of RPGR$^{ORF15}$ (FIG. 18A) and RPGR$^{ex1-19}$ (FIG. 18B) was analyzed by qRT-PCR after transfecting the indicated human fibroblasts with pEGFP empty vector or pEGFP-RPGR$^{ORF15}$. All cells overexpressed RPGR$^{ORF15}$ to similar levels (4-5 folds higher) when compared to RPGR$^{ORF15}$ levels in the pEGFP-expressing cells.
Figure 18B:
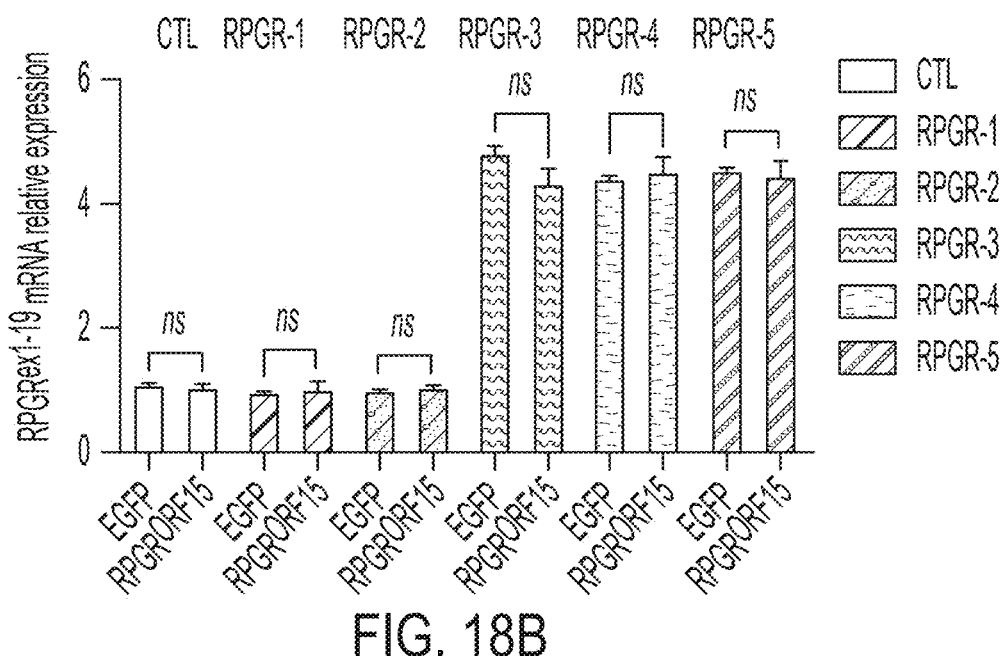

Further support of this hypothesis comes from the observation that expressing RPGR$^{ORF15}$ in the control or RPGR-2 (~20% longer cilia) cells significantly reduced the cilia length 10-20% less than the average lengths of the GFP-expressing control cells. All cells transfected with RPGR$^{ORF15}$-encoding cDNA overexpressed RPGR$^{ORF15}$ to similar levels (4-5 fold higher) when compared to GFP-expressing control cells (FIG. 18A) and did not alter the RPGRex1 19 levels (FIG. 18B).

Some RPGR$^{ORF15}$-Mutant Isoforms are Less Stable

Figure 14C:
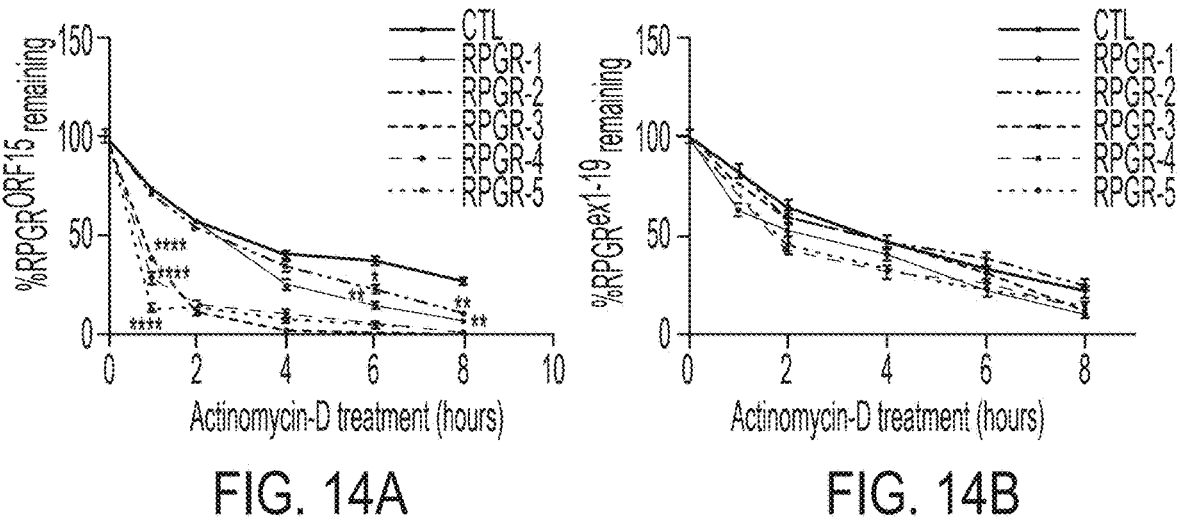

Varying mRNA levels of the RPGR isoforms could be due to the mutations affecting the purine-rich repeat region of the genomic DNA or RPGR mRNA stability. Since some RPGR$^{ORF15}$ mutations (RPGR-2, RPGR-6, RPGR-7, and RPGR-8) did not affect the isoform ratio, it was concluded that the DNA architecture in the region of those mutations is not sufficient to cause the observed changes. It was then tested whether the effect on RPGR isoform ratio is due to changes in its stability. Transcription inhibition assays were performed using actinomycin D to assess the half-lives of the RPGR isoforms. Studies revealed that the mutant RPGR$^{ORF15}$ levels rapidly decrease to ~10% of the total levels within the first hour of actinomycin D treatment and are at minimal levels by 4 hours in RPGR-3, RPGR-4, and RPGR-5 samples. Their levels also remained significantly lower than the control at all time points. However, the rate of decline of the mutant RPGR$^{ORF15}$ levels in RPGR-1 and RPGR-2 samples was overall similar to that of the control RPGR$^{ORF15}$ mRNA. There was, however, a slightly faster decline of the mutant RPGR$^{ORF15}$ levels in RPGR-1 and RPGR-2 at 6 and 8 hours of actinomycin D treatment when compared to the control (FIG. 14A). As predicted, a significant difference in the decay of the RPGRex1 19 mRNA in the patient fibroblasts relative to the controls (FIG. 14B) was not detected. Based on these studies, it was found that the half-life of the mutant RPGR$^{ORF15}$ in RPGR-1 and RPGR-2 after actinomycin D treatment relative to vehicle treatment was similar to that in control fibroblasts (~2.3 and 2.2 hours for RPGR-1 and RPGR-2, respectively and 1.6 hours for control) (FIGS. 12A-12F) whereas the half-life of the mutant RPGR$^{ORF15}$ in RPGR-3, RPGR-4, and RPGR-5 was 0.67, 0.51, and 0.28 hours, respectively. Linear regression analysis further validated that the decay kinetics of mutant RPGR$^{ORF15}$ in RPGR-3, RPGR-4, and RPGR-5 does not follow a linear correlation (FIG. 14C).

RPGR$^{ex1-19}$ Knockdown in Mutant Fibroblasts

Figure 15A:
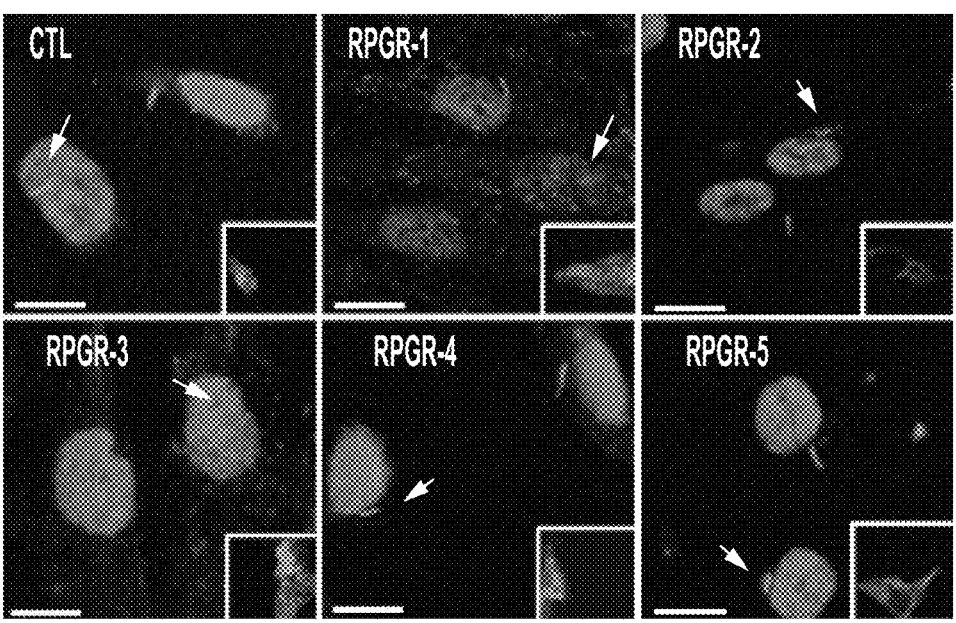
FIGS. 15A-15B show the effect of RPGR$^{ex1-19}$ knock-down on the cilia defect.
Figure 15B:
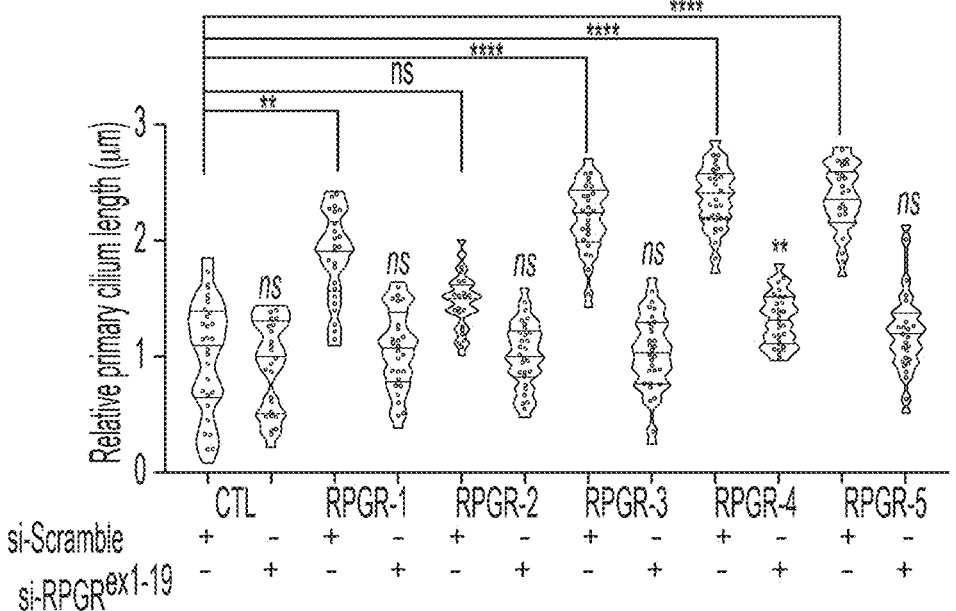
Figure 19A:
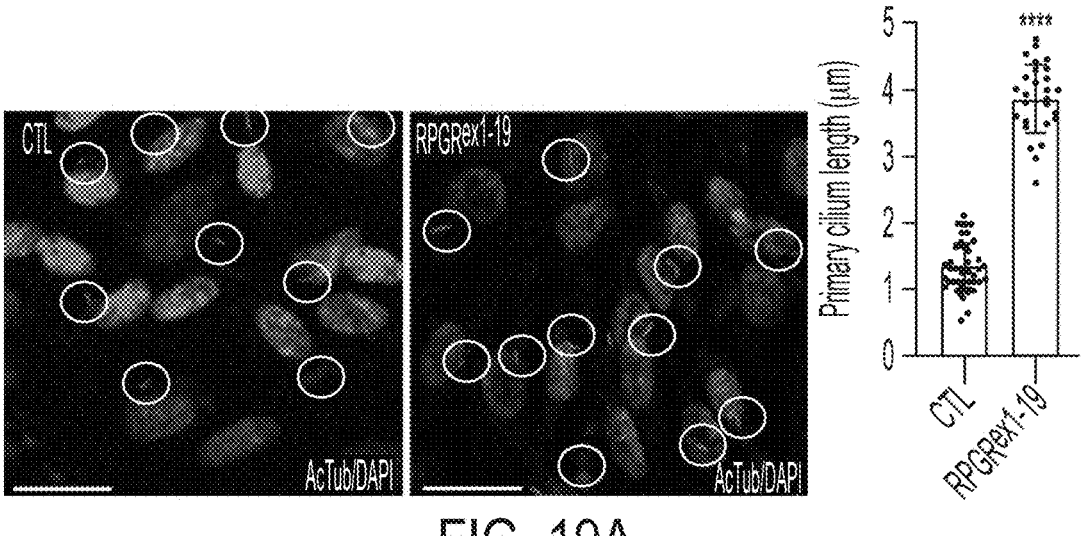
FIG. 19A shows hTERT-RPE-1 cells were transiently transfected with cDNA encoding GFP alone or GFP-RPGR$^{ex1-19}$ followed by staining with acetylated α-tubulin (AcTub; circled white). DAPI (grey oval shape) was used to stain the nuclei. The cilia length was quantified and represented as a bar graph. **: p<0.0001.
Figure 19B:
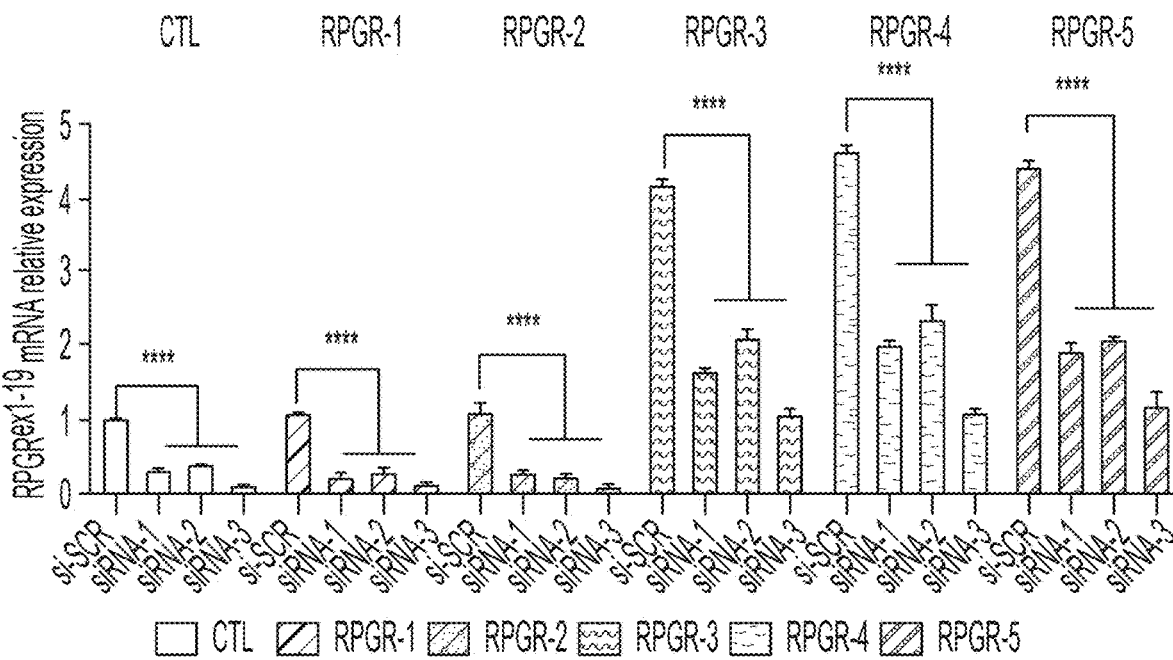
FIG. 19B shows three siRNAs against RPGR$^{ex1-19}$ (siRNA-1, siRNA-2, and siRNA-3) were tested for their ability to knock down RPGR$^{ex1-19}$ expression after transfection into the indicated human fibroblasts. Although all siRNAs exhibited significant down-regulation of the RPGR$^{ex1-19}$ isoform when compared to a scrambled siRNA, siRNA-3 was the most potent. : p<0.0001.
Figure 19C:
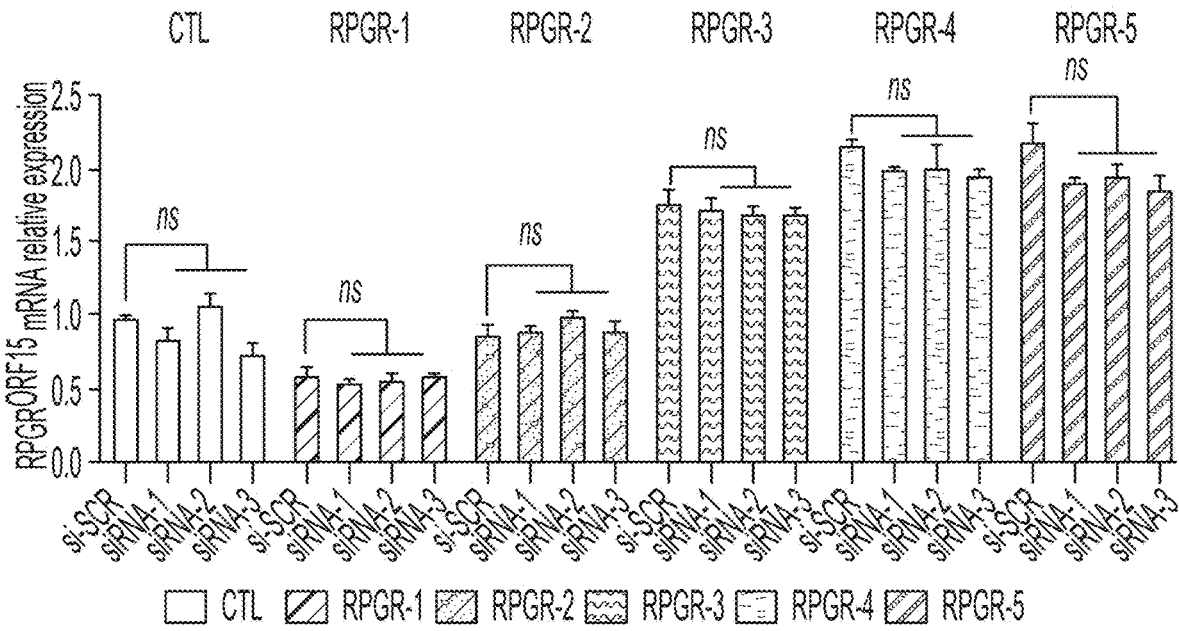
FIG. 19C** shows RPGR$^{ex1-19}$ siRNA expression did not alter the expression of RPGR$^{ORF15}$. ns: not significant.

If RPGR$^{ORF15}$ only partly reversed the cilia length, the increase in the RPGRex1 19 levels could also be relevant to the observed cilia elongation in the RPGR$^{ORF15}$-mutant fibroblasts. To test this, RPGRex1 19 was overexpressed in hTERT-RPE1 cells by transient transfection. Analysis revealed 3-4 fold longer cilia in the RPGRex1 19 overexpressing cells as compared to the control cells (FIG. 19A). Thus, it was hypothesized that reducing the RPGRex1 19 levels will alleviate the elongated cilia phenotype. To this end, siRNA-mediated depletion of RPGRex1 19 was performed. Three siRNAs (siRNA-1, siRNA-2, and siRNA-3) against RPGRex1 19 were designed. All siRNAs reduced the expression of RPGRex1 19, with maximal inhibition observed with siRNA-3 (FIG. 19B), when compared to the levels expressed in cells transfected with a scrambled sequence control. Moreover, the siRNAs did not affect RPGR$^{ORF15}$ levels in the fibroblasts (FIG. 19C). Transfection of RPGRex1 19-siRNAs followed by immunofluorescence analysis in RPGR-3 and RPGR-5 revealed an almost complete reversal of the cilia elongation phenotype with the cilia length comparable to that of the scrambled siRNA-treated control fibroblasts. RPGR-4 showed ~90% reduction in cilia length compared to scrambled siRNA-treated cells (FIGS. 15-15B).

Generation and Characterization of RPGR Isoform-Specific Antibodies

The RPGR isoform-specific antibodies were generated against the protein domains present specifically in each isoform (Abclonal). For RPGR$^{ex1-19}$-specific antibody, the protein domain encoded by amino acids 923-1039 encompassing exons 16-18 of the RPGR protein was used to generate antibodies in rabbits. For RPGR$^{ORF15}$-specific antibody, the protein domain encoded by amino-acids 563-804 encompassing exon $^{ORF15}$ was used.

Human Photoreceptor Stem Cell Maintenance and Retinal Differentiation Culture

The human embryonic and iPS stem cell lines (Rb2 from Wicell and iPS RPGR cell lines) were maintained in feeder free conditions with E8 (Thermo Fisher) media on geltrex coated 6 well plates. Briefly, when 80% confluent hPSCs were dissociated using Versene solution for 10 minutes. PSC small clumps were collected, washed twice with PBS and resuspended in E8 media for further maintenance culture on 6 well plates. For retinal neuroepithelial differentiation, human PSCs were maintained as described above until 90-95% confluent, then media without FGF (E6, Thermo Fisher) was added to the cultures for two days (D1 and 2 of differentiation) followed by a neural induction period (up to 7 weeks) in proneural induction media (Advanced DMEM/F12, MEM non essential amino acids, N2 Supplement, 100 mM Glutamine and Pen/Strep). Lightly-pigmented islands of retinal pigmented epithelium (RPE) appeared as early as week 3 in culture. Optic vesicles were formed from within the RPE region between weeks 4 and 7. During this period neuroretinal vesicles were manually excised with 21 G needles and kept individually in low binding 96 well plates in retinal differentiation media (DMEM, F12, Pen/Strep and B27 without retinoic acid). At 6 wks of differentiation retinal differentiation medium was supplemented with 10% FBS, 100 uM taurine (Sigma, T4871) and 2 mM glutamax and at 10 wks 1 uM retinoic acid (RA) was added (RDM+ Factors media). At 10 wks of culture vesicles were transferred to low binding 24 well plates (5 vesicles/well). At 12 wks of differentiation, media was changed again to ALT media (Advanced DMEM/F12, B27 without retinoic acid, N2 Supplement, 4 mM glutamax, 7.5 mM glucose, 100 uM taurine, 0.5 μM RA and Pen/Strep). Maintenance cultures of hPSCs were feed daily and differentiation cultures were feed every 2-3 days. At 24 weeks 10 retinal organoids were collected per sample and snap frozen or placed in Trizol and stored at −20° C.

Discussion

Although RPGR$^{ORF15}$ gene augmentation therapy has been successful in naturally occurring canine mutations and murine models (42, 43), and is currently in human clinical trials, efficacy of the treatment across the large spectrum of human exon $^{ORF15}$ mutations is currently not known. It is demonstrated that all eight RPGR$^{ORF15}$ mutations tested here cause cilia length defects of varying extents, lead to mutant mRNA instability, and four mutations lead to a significant increase in the RPGRex1 19/RPGR$^{ORF15}$ ratio. Results indicate that three out of four exon $^{ORF15}$ mutations that result in an increase in the RPGRex1 19/RPGR$^{ORF15}$ mRNA ratio have shorter half-life due to relatively faster mutant mRNA decay yet have relatively higher steady-state levels of the mutant RPGR$^{ORF15}$ mRNA and protein. The precise mechanism of the transcriptional complexity observed in this study is not clear. Nonetheless, these results point to transcriptional adaptation in which the unstable mRNA transcripts can result in a feedback response to increase the levels of the protein. RPGR transcriptional adaptation could increase the RPGR$^{ORF15}$ protein levels, however, at the same time also increase RPGRex1 19 levels, as observed in this study. Such transcriptional adaptation may result from the need to compensate for the decaying mutant RPGR$^{ORF15}$ transcripts (44-46); however, its relevance to retinal disease remains to be determined. It was also found that the expression of wild type RPGR$^{ORF15}$ did not affect the elevated RPGRex1 19 levels in fibroblasts. This suggests that the mechanism of increase in the RPGRex1 19 levels is not due to the absence of the wild type RPGR$^{ORF15}$ and implicates the expression of the mutant $^{ORF15}$ isoforms. The observed effects on cilia growth on the other hand, seem to be due in part to the lack of the RPGR$^{ORF15}$ protein and to the relatively increased expression of RPGRex1 19. This is because RPGR$^{ORF15}$ overexpression or RPGRex1 19 knockdown were able to partly reverse the cilia defect, with RPGRex1 19 knockdown showing better reversal of the cilia length. These results suggest that the relative levels of both RPGR isoforms are critical for optimal cilia growth. Further support of this hypothesis comes from the observation that the overexpression of RPGRex1 19 leads to longer cilia while that of RPGR$^{ORF15}$ results in shorter cilia. Additionally, previous studies showed that overexpression of Rpgrex1 19 or RPGR$^{ORF15}$ in mice results in severe retinal degeneration (47, 48).

What is the mechanism of cilia elongation in RPGR$^{ORF15}$ mutant samples? It was found that the imbalanced RPGRex1 19/RPGR$^{ORF15}$ ratio subsequently results in higher overall levels of the RPGR proteins. This could lead to increased context-dependent function of RPGR-containing protein complexes at the cilia and alteration of the gate-keeping function at the transition zone. It was previously shown that RPGR regulates the composition of the ciliary outer segments of photoreceptors by affecting its ability to maintain the barrier at the transition zone (30). RPGRex1 19 is also involved in regulating ciliary cargo trafficking in cultured cells as well as mouse photoreceptors (24). Moreover, both RPGR isoforms interact genetically and physically with CEP290 and this interaction is critical for photoreceptor outer segment viability and function (24). Hence, RPGR-CEP290 interaction could take place in overlapping as well as distinct complexes consisting of the different isoforms. We, therefore, propose that RPGR$^{ORF15}$ mutations that perturb ratio of the two isoforms and subsequently the integrity or recruitment of the multiprotein complexes, result in altered ciliary trafficking. Further studies are underway to delineate the mechanism of such effects.

Mutations in retinal ciliary proteins have been mostly associated with reduced cilia length and photoreceptor outer segment degeneration. Knockdown of rpgr in zebrafish or in cultured human RPE cell lines results in shorter cilia (49-52). Although the fibroblasts derived from RPGR$^{ORF15}$ patients exhibited longer cilia, longer photoreceptor outer segments were not observed in iPSC-derived optic cups or in RPGR-patients. These results could reflect cell-type specific differences in the utilization of distinct ciliary regulation pathways. Previous clinical findings and animal model studies also showed that RPGR mutations do not prevent the initial generation of the photoreceptor outer segments but that they undergo progressive degeneration (28, 29, 31). Of note, context-dependent cilia length regulation and outer segment defects have been reported with CEP290-patient fibroblasts and CP110-mouse fibroblasts (39, 53).

The RPGR-2, RPGR-3, RPGR-4, and RPGR-5 are similar in nature (small frameshifts), they produce profoundly different effects. These could partly be due to the location of these mutations: while the RPGR-2 mutation is located towards the 3'-region of the non-repetitive exon 15, the RPGR-3, RPGR-4, and RPGR-5 mutations lie in the 5'-region of the repetitive purine-rich region. The repetitive region of these mutations may be involved in the recognition or recruitment of mRNA decay factors or splicing effectors. On the other hand, the RPGR-1 mutation, which lies within exon 15 does not show increased RPGRex1 19 levels, yet the steady-state levels of the mutant RPGR$^{ORF15}$ mRNA are significantly reduced. Since the mRNA stability profile of this mutant is similar to that of the control, there may be a different mechanism underlying reduced mutant RPGR$^{ORF15}$ levels. However, the resultant increase in the RPGRex1 19/RPGR$^{ORF15}$ ratio indicates the similar cilia extension defect as RPGR-3, RPGR-4, and RPGR-5.

The partial effect of overexpression of RPGR$^{ORF15}$ in the mutant fibroblasts on the rescue of the ciliary phenotype potentially also raises questions that they may be relevant to the ongoing clinical trials that utilize RPGR$^{ORF15}$ gene augmentation strategy. These studies are based upon the rationale that the RPGR$^{ORF15}$ mutations result in a complete or partial loss of function. While the study was in progress, first results of a phase 1/2 study reported encouraging results with seven out of 18 patients showing early improvement in visual function after RPGR$^{ORF15}$ gene augmentation therapy (54). However, at least one of the patients with the mutation c.2405 2406delAG (RPGR-3) did not reveal reliable clinical improvement. Results predict that this mutation would cause a significant disruption in the RPGR isoform ratio and abnormally longer cilia that might not be completely reversed by RPGR$^{ORF15}$ overexpression. This study underscores the complexity of RPGR gene defects and suggests that gene therapy strategies may need to focus on ways to restore the appropriate RPGRex1 19/RPGR$^{ORF15}$ ratio, taking into account the consequences of different $^{ORF15}$ mutations; $^{ORF15}$ overexpression may be a less effective therapeutic strategy for patients with certain RPGR$^{ORF15}$ mutations.

TABLE 1

Figure 1B:
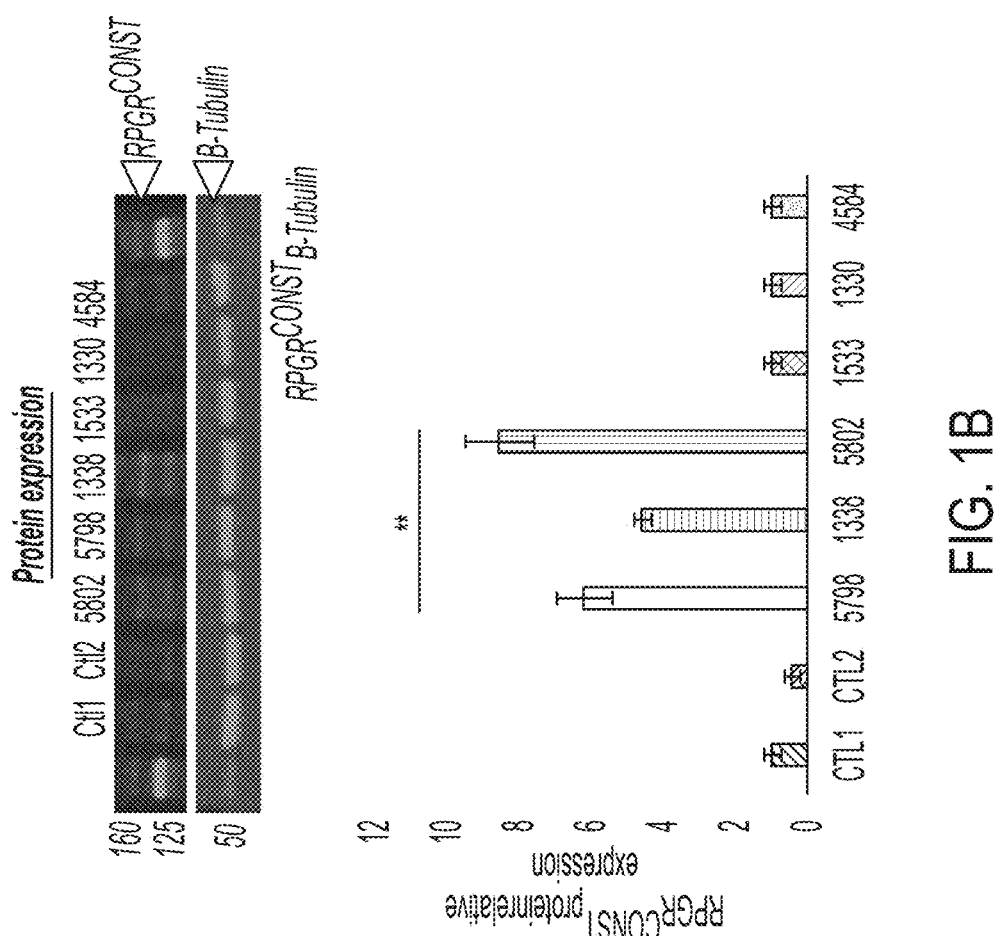
Figure 1C:
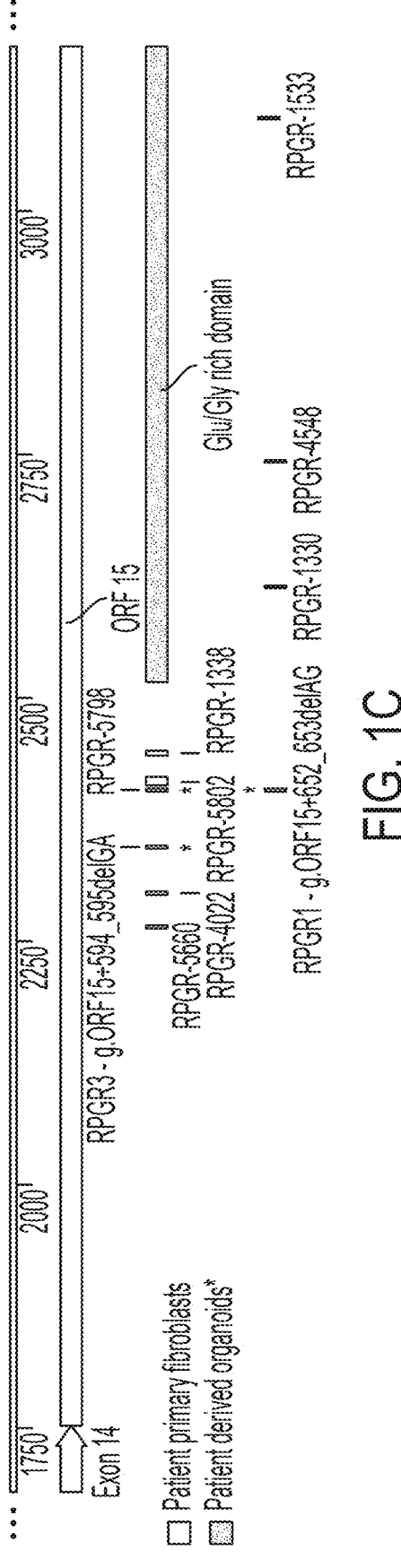

| | Western Blot | | | |
|---|---|---|---|---|
| Name | Brand | Cat number | Dilution | |
| RPGR ex16-18 | Abclonal | Supplementary FIG. 1A | 1:1000 | Rabbit I$^y$ Ab |
| RPGR$^{ORF15}$ | Abclonal | Supplementary FIG. 1A | 1:1000 | Rabbit I$^y$ Ab |

TABLE 1-continued

|  | Western Blot | | | |
| --- | --- | --- | --- | --- |
| Name | Brand | Cat number | Dilution | |
| IRDye 680LT anti mouse | Licor | 926-68020 | 1:5000 | Goat II$^\gamma$ Ab |
| IRDye 800CW anti rabbit | Licor | 926-32211 | 1:5000 | Goat II$^\gamma$ Ab |
| Anti-acetylated α-tubulin | Sigma Aldrich | T6793 | 1:500 | Mouse I$^\gamma$ Ab |
| Anti-γ-tubulin (GT4511) | Invitrogen | MA5-31482 | 1:500 | Mouse I$^\gamma$ Ab |
| Anti-polyglutamylated tubulin (GT335) | Adipogen | AG-20B-0020B-C100 | 1:200 | Mouse I$^\gamma$ Ab |
| Anti-Rhodopsin clone RET-P1 | Merk Millipore | MAB5316 | 1:200 | Mouse I$^\gamma$ Ab |
| Anti-CEP290 | Bethyl Laboratories | A301-659A | 1:200 | Rabbit I$^\gamma$ Ab |
| Anti-Arl13b | Proteintech | 17711-1-AP | 1:500 | Rabbit I$^\gamma$ Ab |
| Anti-GFP | Abcam | ab13970 | 1:500 | Chicken I$^\gamma$ Ab |
| Anti-Mouse IgG (H + L), 488 nm | Invitrogen | A32723 | 1:1000 | Goat II$^\gamma$ Ab |
| Anti-Mouse IgG (H + L), 546 nm | Invitrogen | A11030 | 1:1000 | Goat II$^\gamma$ Ab |
| Anti-Rabbit IgG (H + L), 488 nm | Invitrogen | A11008 | 1:1000 | Goat II$^\gamma$ Ab |
| Anti-Rabbit IgG (H + L), 546 nm | Invitrogen | A11010 | 1:1000 | Goat II$^\gamma$ Ab |
| Anti-Chicken IgG (H + L), 488 nm | Invitrogen | A11039 | 1:1000 | Goat II$^\gamma$ Ab |

TABLE 2

RT-qPCR primers

| Name | Sequence |
| --- | --- |
| RPGR$^{ex1-19}$ E17-18 Fwd | GAACGGGCCATTTGTGAGTA (SEQ ID NO: 19) |
| RPGR$^{ex1-19}$ E19 Rev | GGTTCTGGTCGGCATCTTTAT (SEQ ID NO: 20) |
| RPGR$^{ORF15}$ E15 Fwd | GGAAGGAGCAGAGGATTCAAA (SEQ ID NO: 21) |
| RPGR$^{ORF15}$ ORF15 Rev | CCTCATCTTGCCAGTGTTCT (SEQ ID NO: 22) |
| β-actin Fwd | GACCTCTATGCCAACACAGT (SEQ ID NO: 23) |
| β-actin Rev | AGTACTTGCGCTCAGGAGGA (SEQ ID NO: 24) |
| RPLP0 Fwd | GCATCAGTACCCCATTCTATCAT (SEQ ID NO: 25) |
| RPLP0 Rev | AGGTGTAATCCGTCTCCACAGA (SEQ ID NO: 26) |

DsiRNAs for knockdown

| Name | Duplex sequence |
| --- | --- |
| dsi-NC-SCR Fwd | CUUCCUCUCUUUCUCUCCCUUGUGA (SEQ ID NO: 27) |
| dsi-NC-SCR Rev | AGGAAGGAGAGAAAGAGAGGGAACACU (SEQ ID NO: 28) |
| dsi-RPGR$^{ex1-19}$.1 Fwd | CACCAAGCAAAGACAUGAAAAAAAC (SEQ ID NO: 29) |
| dsi-RPGR$^{ex1-19}$.1 Rev | UUGUGGUUCGUUUCUGUACUUUUUUUG (SEQ ID NO: 30) |
| dsi-RPGR$^{ex1-19}$.2 Fwd | GGAGCAGAAAGAACCAAUGAUGATA (SEQ ID NO: 31) |
| dsi-RPGR$^{ex1-19}$.2 Rev | UUCCUCGUCUUUCUUGGUUACUACUAU (SEQ ID NO: 32) |
| dsi-RPGR$^{ex1-19}$.3 Fwd | AUCAAAAGAUUGUCAAGAAUAACAA (SEQ ID NO: 33) |
| dsi-RPGR$^{ex1-19}$.3 Rev | UUUAGUUUUCUAACAGUUCUUAUUGUU (SEQ ID NO: 34) |

Figure 20A:
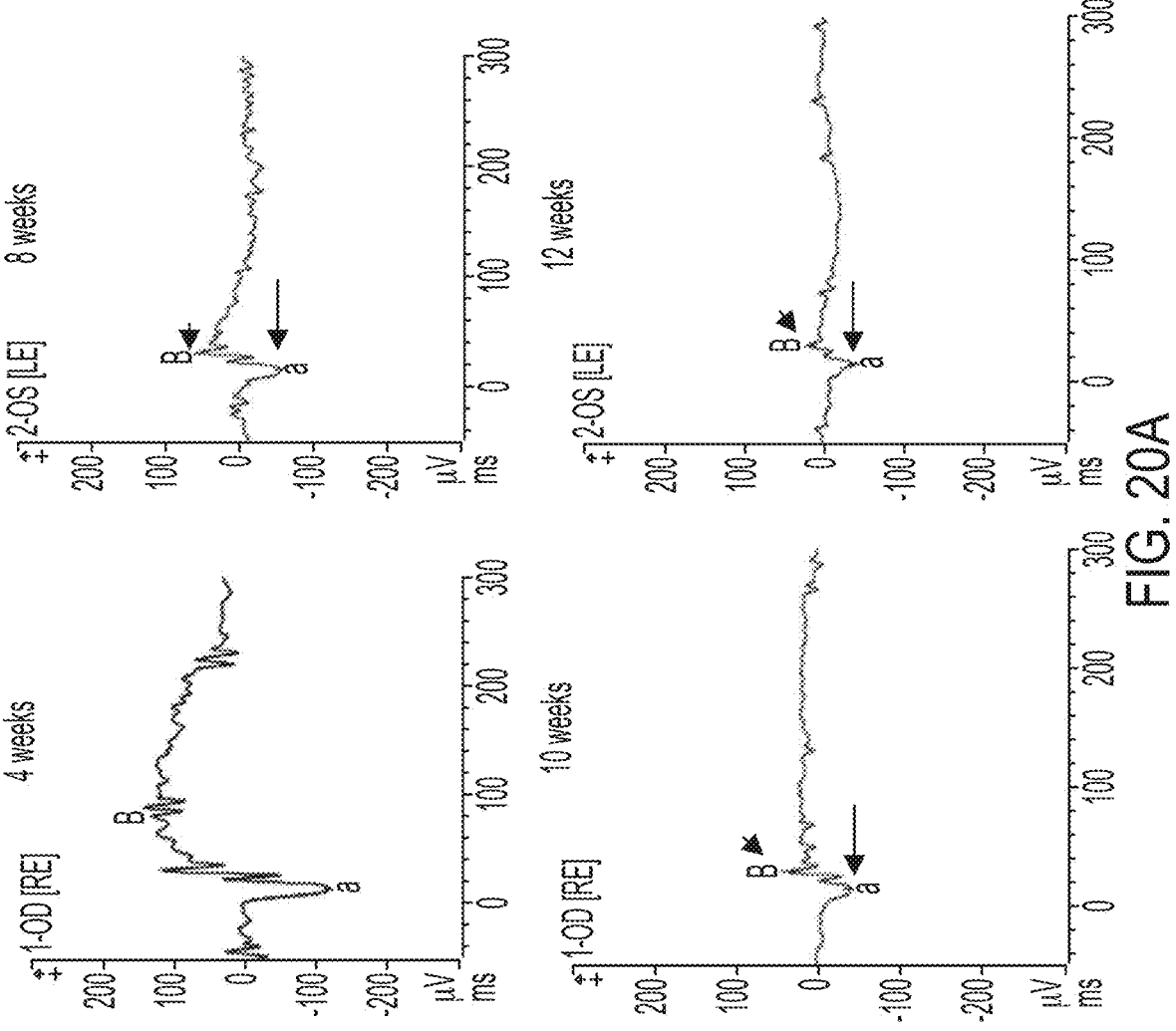
FIGS. 20A-20E show in vivo phenotyping of miR129.
Figure 20B:
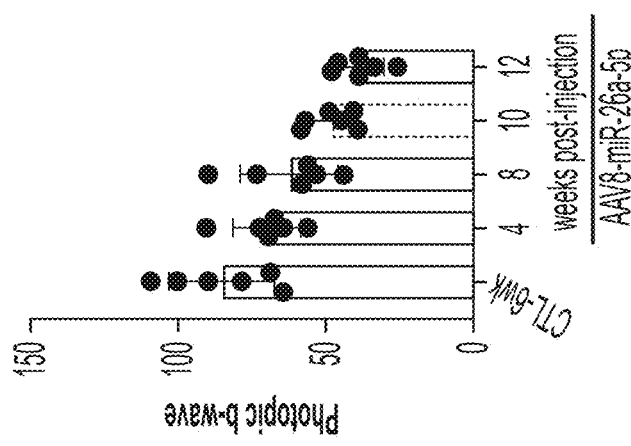
Figure 20B:
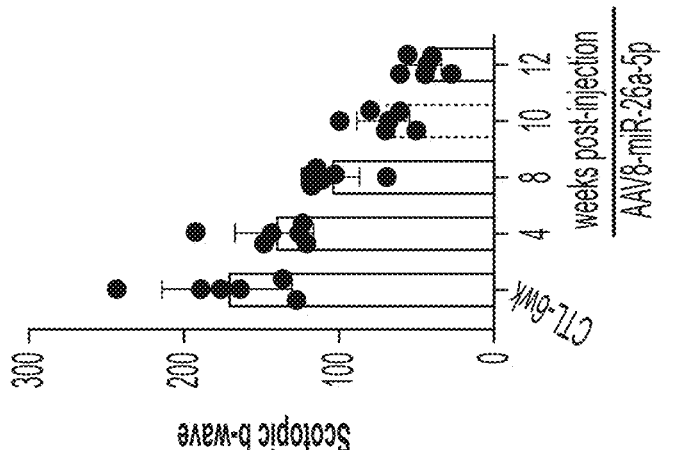
Figure 20B:
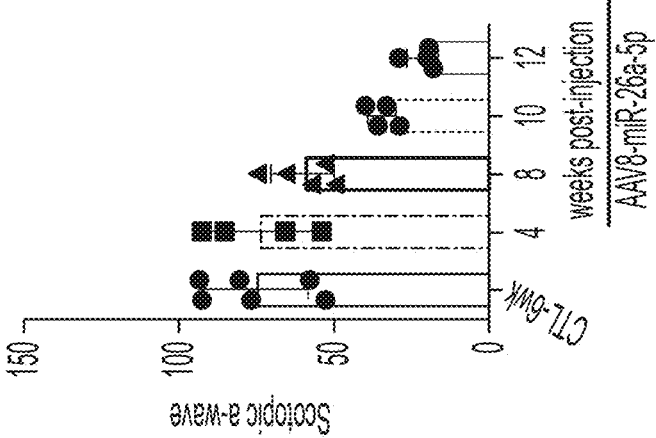
Figure 20C:
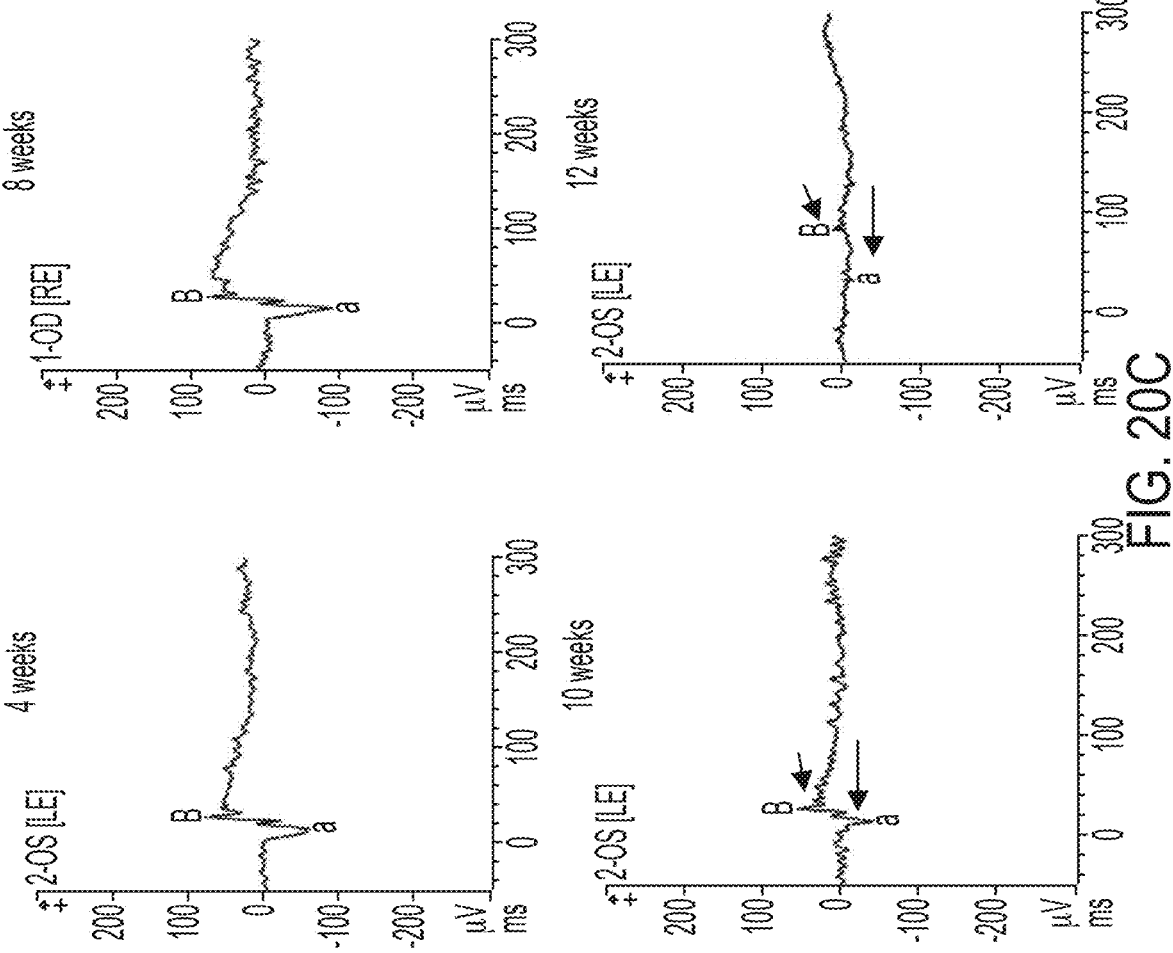
Figure 20D:
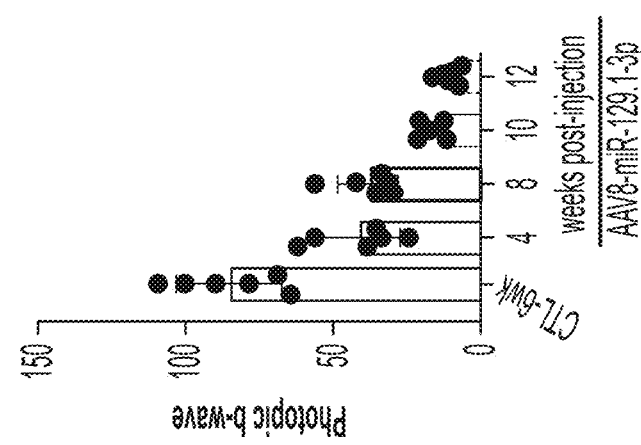
Figure 20D:
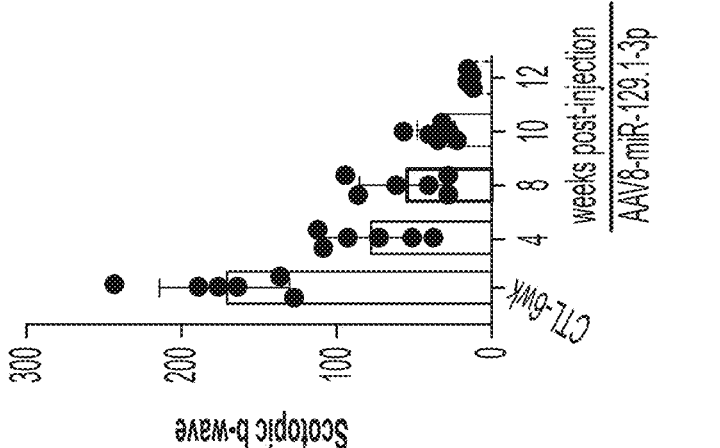
Figure 20D:
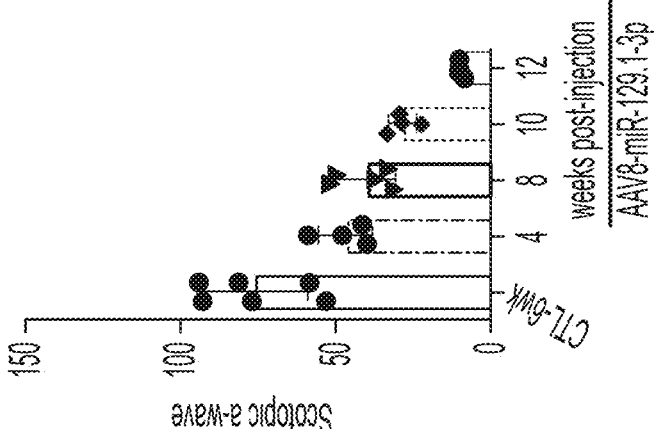
Figure 20E:
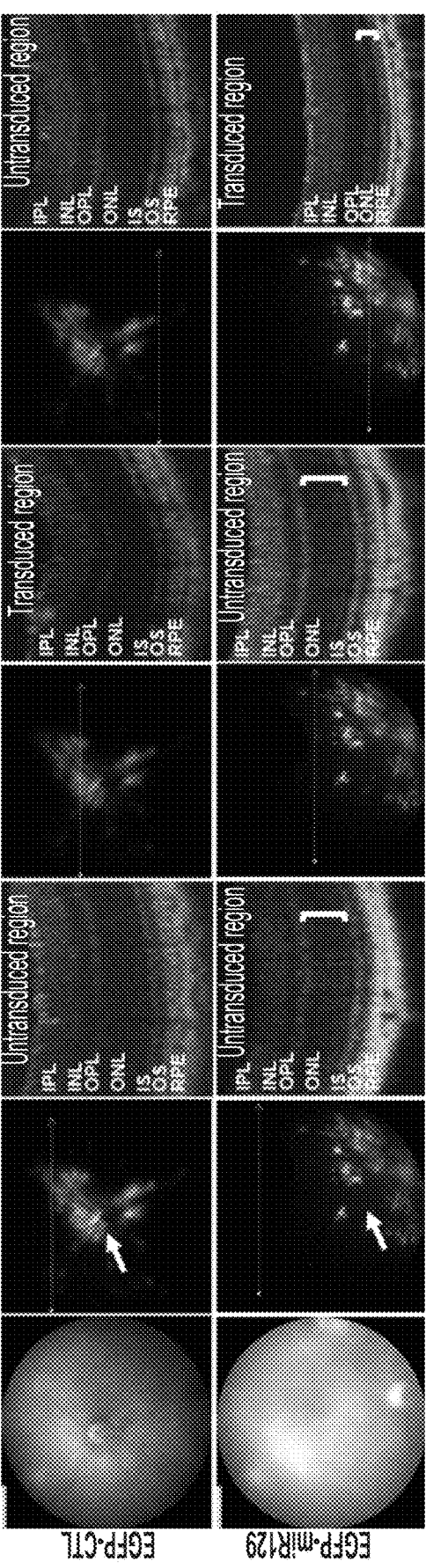

Example 3: In Vivo AAV Transduced mrR-129 Shows a Thinning Phenotype in Mouse Retina AAV8-encoding miR-26a-5p was sub-retinally injected into wild type mice at post-natal day P10. The effect on light response of the photoreceptors was analyzed by electroretinography (ERG) at indicated weeks post injection. The decline in the light-responsive a-wave (longer arrows) and b-wave (shorter arrows) is indicated (FIG. 20A). Amplitudes in both scotopic (dark-adapted) and light-adapted (photopic) conditions were quantified and show significant decline in the light response with age (FIG. 20B). AAV8-encoding miR-129.1-3p was sub-retinally injected into wild type mice at post-natal day P10 (FIG. 20C). The effect on light response of the photoreceptors was analyzed by electroretinography (ERG) at indicated weeks post injection. The decline in the light-responsive a-wave (longer arrows) and b-wave (shorter arrows) is indicated. Amplitudes in both scotopic (dark-adapted) and light-adapted (photopic) conditions were quantified and show significant decline in the light response with age (FIG. 20D). AAV8-encoding EGFP (Control; CTL (top row) or miR129.1-3p with GFP (bottom row)) were sub-retinally injected into mouse retina (FIG. 20E). Four (4) weeks post-injection, the mice were imaged by funduscopy to identify the transduced region (arrows). The areas marked by horizontal lines were subsequently analyzed by optical coherence tomography (OCT). The OCT image shows the different retinal layers as marked. The areas transduced with GFP-control or the untransduced areas of the same retinas did not show detectable differences in the different retinal layer thickness. However, there was significant thinning of the outer nuclear layer (ONL), which represents the photoreceptor nuclei in the miR-129-transduced regions versus the untransduced regions. RPE: retinal pigment epithelium; OS: outer segment; IS: inner segment; OPL: outer plexiform layer; INL: inner nuclear layer; GCL: ganglion cell layer.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Exemplary Sequences

In some embodiments, an isolated nucleic acid as described herein (e.g., an inhibitory nucleic acid) comprises the nucleic acid sequence set forth in any one of SEQ ID NO: 1-14, or a complement or reverse complement thereof. In some embodiments, an isolated nucleic acid as described herein (e.g., an inhibitory nucleic acid) is encoded by the nucleic acid sequence set forth in any one of SEQ ID NO: 1-14, or a complement or reverse complement thereof.

DsiRNA sequences

*Nucleotides written in bold represents sense and antisense RNA sequences targeting RPGR$^{CONST}$. Nucleotides underlined represents DNA modified nucleotides to increase dsiRNA stability.

| miRNA backbone | Targeted exon | Targeted sequence | Off-Targets | Primer sequence |
|---|---|---|---|---|
| amiR-RPGR_Ex19 | 19 | TCGGCAT CTTTATT ATCACTT (SEQ ID NO: 9) | 0 | UGCUGUCGG CAUCUUU<u>AU</u> <u>UAU</u>CACUUG UUUUGGCCA CUGACUGAC AAGUGAUAA AAGAUGCCG ACAGGA (SEQ ID NO: 10) |
| amiR-RPGR_Ex16 | 16 | TCCCACA GTTTTCT TCTTGCT (SEQ ID NO: 11) | 0 | UGCUGUC<u>CC</u> ACAGUUU<u>AU</u> <u>UUC</u>UUGCUG UUUUGGCCA CUGACUGAC AGCAAGAAA AACUGUGGG ACAGGA (SEQ ID NO: 12) |

| Name | Duplex sequence | Targeted exon |
|---|---|---|
| dsi-NC-SCR | CUUCCUCUCUUUCU UCUCCCUUGUGA (SEQ ID NO: 1) | NA |
| | AGGAAGGAGAGAAA GAGAGGGAACACU (SEQ ID NO: 2) | |
| CD.Ri.215151.13.1 (siRNA.1) | CACCAAGCAAAGA CAUGAAAAAAAC (SEQ ID NO: 3) | 18 |
| | UUGUGGUUCGUUU CUGUACUUUUUUG (SEQ ID NO: 4) | |
| CD.Ri.215151.13.2 (siRNA.1) | GGAGCAGAAAGAA CCAAUGAUGAUA (SEQ ID NO: 5) | 16 |
| | UUCCUCGUCUUUC UUGGUUACUACUAU (SEQ ID NO: 6) | |
| CD.Ri.215151.13.3 (siRNA.1) | AUCAAAAGAUUGU CAAGAAUAACAA (SEQ ID NO: 7) | 19 |
| | UUUAGUUUUCUAA CAGUUCUUAUUGUU (SEQ ID NO: 8) | |

Artificial miRNA Sequences (SEQ ID NO: 9-12)

| | Mature sequence | RPGR target |
|---|---|---|
| miR26a-5p | TTCAAGTAATCC AGGATAGGCT (SEQ ID NO: 13) | CONST RPGR |
| miR129.1-3p | AAGCCCTTACC CCAAAAAGTAT (SEQ ID NO: 14) | ORF15 RPGR | miRNA sequences (SEQ ID NO: 13-14)

RPGR$^{ORF15}$ amino acid sequence
(SEQ ID NO: 15)

MREPEELMPDSGAVFTFGKSKFAENNPGKFWFKND

VPVHLSCGDEHSAVVTGNNKLYMFGSNNWGQLGLG

SKSAISKPTCVKALKPEKVKLAACGRNHTLVSTEG

GNVYATGGNNEGQLGLGDTEERNTFHVISFFTSEH

KIKQLSAGSNTSAALTEDGRLFMWGDNSEGQIGLK

NVSNVCVPQQVTIGKPVSWISCGYYHSAFVTTDGE

LYVFGEPENGKLGLPNQLLGNHRTPQLVSEIPEKV

IQVACGGEHTVVLTENAVYTFGLGQFGQLGLGTFL

FETSEPKVIENIRDQTISYISCGENHTALITDIGL

MYTFGDGRHGKLGLGLENFTNHFIPTLCSNFLRFI

VKLVACGGCHMVVFAAPHRGVAKEIEFDEINDTCL

SVATFLPYSSLTSGNVLQRTLSARMRRERERSPD

-continued

SFSMRRTLPPIEGTLGLSACFLPNSVFPRCSERNL

QESVLSEQDLMQPEEPDYLLDEMTKEAEIDNSSTV

ESLGETTDILNMTHIMSLNSNEKSLKLSPVQKQKK

QQTIGELTQDTALTENDDSDEYEEMSEMKEGKACK

QHVSQGIFMTQPATTIEAFSDEEVEIPEEKEGAED

SKGNGIEEQEVEANEENVKVHGGRKEKTEILSDDL

TDKAEVSEGKAKSVGEAEDGPEGRGDGTCEEGSSG

AEHWQDEEREKGEKDKGRGEMERPGEGEKELAEKE

EWKKRDGEEQEQKEREQGHQKERNQEMEEGGEEEH

GEGEEEEGDREEEEEKEGEGKEEGEGEGEEVEGEREK

EEGERKKEERAGKEEKGEEEGDQGEGEEEETEGRG

EEKEEGGEVEGGEVEEGKGEREEEEEEGEGEEEEG

EGEEEEGEGEEEEGEGKGEEEEGEEGEGEGEEEGEEGE

GEGEEEEGEGEGEEEGEGEGEEEEGEGEGEEEGEG

EGEEEEGEGKGEEEGEEGEGEGEEEEGEGEGEDGE

GEGEEEEGEWEGEEEEGEGEGEEEGEGEGEEGEGE

GEEEEGEGEGEEEEGEEEGEEGEGEGEEEGEGEGEE

EEEGEVEGEVEGEEGEGEGEEEEGEEEGEERKEKEG

EGEENRRNREEEEEEGKYQETGEEENERQDGEEY

KKVSKIKGSVKYGKHKTYQKKSVTNTQGNGKEQRS

KMPVQSKRLLKNGPSGSKKFWNNVLPHYLELK

RPGR$^{ORF15}$ nucleic acid sequence
SEQ ID NO: 16)

GTAGTTGATCTCCGGAGTTTCGCCATGCGGAACTT

GGGGGCTTTCGCGGCCCGCGTCGGTGCGGAGTAGC

TGCTTTAGCCCCGACCAAACCGTCCTCTACAGCCT

CCTGGCCCCGGCGCAGGCTGCCCGTACTGCCCGTG

GCATGAGGGAGCCGGAAGAGCTGATGCCCGATTCG

GGTGCTGTGTTTACATTTGGGAAAAGTAAATTTGC

TGAAAATAATCCCGGTAAATTCTGGTTTAAAAATG

ATGTCCCTGTACATCTTTCATGTGGAGATGAACAT

TCTGCTGTTGTTACCGGAAATAATAAACTTTACAT

GTTTGGCAGTAACAACTGGGGTCAGTTAGGATTAG

GATCAAAGTCAGCCATCAGCAAGCCAACATGTGTC

AAAGCTCTAAAACCTGAAAAAGTGAAATTAGCTGC

CTGTGGAAGGAACCACACCCTGGTGTCAACAGAAG

GAGGCAATGTATATGCAACTGGTGGAAATAATGAA

GGACAGTTGGGGCTTGGTGACACCGAAGAAAGAAA

CACTTTTCATGTAATTAGCTTTTTTACATCCGAGC

ATAAGATTAAGCAGCTGTCTGCTGGATCTAATACT

TCAGCTGCCCTAACTGAGGATGGAAGACTTTTTAT

GTGGGGTGACAATTCCGAAGGGCAAATTGGTTTAA

-continued

```
AAAATGTAAGTAATGTCTGTGTCCCTCAGCAAGTG

ACCATTGGGAAACCTGTCTCCTGGATCTCTTGTGG

ATATTACCATTCAGCTTTTGTAACAACAGATGGTG

AGCTATATGTGTTTGGAGAACCTGAGAATGGGAAG

TTAGGTCTTCCCAATCAGCTCCTGGGCAATCACAG

AACACCCCAGCTGGTGTCTGAAATTCCGGAGAAGG

TGATCCAAGTAGCCTGTGGTGGAGAGCATACTGTG

GTTCTCACGGAGAATGCTGTGTATACCTTTGGGCT

GGGACAATTTGGTCAGCTGGGTCTTGGCACTTTTC

TTTTTGAAACTTCAGAACCCAAAGTCATTGAGAAT

ATTAGGGATCAAACAATAAGTTATATTTCTTGTGG

AGAAAATCACACAGCTTTGATAACAGATATCGGCC

TTATGTATACTTTTGGAGATGGTCGCCACGGAAAA

TTAGGACTTGGACTGGAGAATTTTACCAATCACTT

CATTCCTACTTTGTGCTCTAATTTTTTGAGGTTTA

TAGTTAAATTGGTTGCTTGTGGTGGATGTCACATG

GTAGTTTTTGCTGCTCCTCATCGTGGTGTGGCAAA

AGAAATTGAATTCGATGAAATAAATGATACTTGCT

TATCTGTGGCGACTTTTCTGCCGTATAGCAGTTTA

ACCTCAGGAAATGTACTGCAGAGGACTCTATCAGC

ACGTATGCGGCGAAGAGAGAGGGAGAGGTCTCCAG

ATTCTTTTTCAATGAGGAGAACACTACCTCCAATA

GAAGGGACTCTTGGCCTTTCTGCTTGTTTTCTCCC

CAATTCAGTCTTTCCACGATGTTCTGAGAGAAACC

TCCAAGAGAGTGTCTTATCTGAACAGGACCTCATG

CAGCCAGAGGAACCAGATTATTTGCTAGATGAAAT

GACCAAAGAAGCAGAGATAGATAATTCTTCAACTG

TAGAAAGCCTTGGAGAAACTACTGATATCTTAAAC

ATGACACACATCATGAGCCTGAATTCCAATGAAAA

GTCATTAAAATTATCACCAGTTCAGAAACAAAAGA

AACAACAAACAATTGGGGAACTGACGCAGGATACA

GCTCTTACTGAAAACGATGATAGTGATGAATATGA

AGAAATGTCAGAAATGAAAGAAGGGAAAGCATGTA

AACAACATGTGTCACAAGGGATTTTCATGACGCAG

CCAGCTACGACTATCGAAGCATTTTCAGATGAGGA

AGTAGAGATCCCAGAGGAGAAGGAAGGAGCAGAGG

ATTCAAAAGGAAATGGAATAGAGGAGCAAGAGGTA

GAAGCAAATGAGGAAAATGTGAAGGTGCATGGAGG

AAGAAAGGAGAAAACAGAGATCCTATCAGATGACC

TTACAGACAAAGCAGAGGTGAGTGAAGGCAAGGCA
```

-continued

```
AAATCAGTGGGAGAAGCAGAGGATGGGCCTGAAGG

TAGAGGGGATGGAACCTGTGAGGAAGGTAGTTCAG

GAGCAGAACACTGGCAAGATGAGGAGAGGGAGAAG

GGGGAGAAAGACAAGGGTAGAGGAGAAATGGAGAG

GCCAGGAGAGGGAGAGAAGGAACTAGCAGAGAAGG

AAGAATGGAAGAAGAGGGATGGGGAAGAGCAGGAG

CAAAAGGAGAGGGAGCAGGGCCATCAGAAGGAAAG

AAACCAAGAGATGGAGGAGGGAGGGGAGGAGGAGC

ATGGAGAAGGAGAAGAAGAGGAGGGAGACAGAGAA

GAGGAAGAAGAGAAGGAGGGAGAAGGGAAAGAGGA

AGGAGAAGGGGAAGAAGTGGAGGGAGAACGTGAAA

AGGAGGAAGGAGAGAGGAAAAAGGAGGAAAGAGCG

GGGAAGGAGGAGAAAGGAGAGGAAGAAGGAGACCA

AGGAGAGGGGGAAGAGGAGGAAACAGAGGGGAGAG

GGGAGGAAAAAGAGGAGGGAGGGGAAGTAGAGGGA

GGGGAAGTAGAGGAGGGGAAAGGAGAGAGGGAAGA

GGAAGAGGAGGAGGGTGAGGGGGAAGAGGAGGAAG

GGGAGGGGGAAGAGGAGGAAGGGGAGGGGGAAGAG

GAGGAAGGAGAAGGGAAAGGGGAGGAAGAAGGGGA

AGAAGGAGAAGGGGAGGAAGAAGGGGAGGAAGGAG

AAGGGGAGGGGGAAGAGGAGGAAGGAGAAGGGGAG

GGAGAAGAGGAAGGAGAAGGGGAGGGAGAAGAGGA

GGAAGGAGAAGGGGAGGGAGAAGAGGAAGGAGAAG

GGGAGGGAGAAGAGGAGGAAGGAGAAGGGAAAGGG

GAGGAGGAAGGAGAGGAAGGAGAAGGGGAGGGGGA

AGAGGAGGAAGGAGAAGGGGAAGGGGAGGATGGAG

AAGGGGAGGGGGAAGAGGAGGAAGGAGAATGGGAG

GGGGAAGAGGAGGAAGGAGAAGGGGAGGGGGAAGA

GGAAGGAGAAGGGGAAGGGGAGGAAGGAGAAGGGG

AGGGGGAAGAGGAGGAAGGAGAAGGGGAGGGGGAA

GAGGAGGAAGGGGAAGAAGAAGGGGAGGAAGAAGG

AGAGGGAGAGGAAGAAGAGGGGAGGGAGAAGGGGAGG

AAGAAGAGGAAGGGGAAGTGGAAGGGGAGGTGGAA

GGGGAGGAAGGAGAGGGGGAAGGAGAGGAAGAGGA

AGGAGAGGAGGAAGGAGAAGAAAGGGGAAAAGGAGG

GGGAAGGAGAAGAAAACAGGAGGAACAGAGAAGAG

GAGGAGGAAGAAGAGGGGAAGTATCAGGAGACAGG

CGAAGAAGAGAATGAAAGGCAGGATGGGAGAGGAGT

ACAAAAAAGTGAGCAAAATAAAAGGATCTGTGAAA

TATGGCAAACATAAAACATATCAAAAAAAGTCAGT

TACTAACACACAGGGAAATGGGAAAGAGCAGAGGT
```

-continued

```
CCAAAATGCCAGTCCAGTCAAAACGACTTTTAAAA

AACGGGCCATCAGGTTCCAAAAAGTTCTGGAATAA

TGTATTACCACATTACTTGGAATTGAAGTAACAAA

CCTTAAATGTGACCCGATTATGGCCAGTCAGACAA

TTTAAATGCCTTGCATATAACGGGCACTCATTACG

TGTTATTAAATTGATTTTATGTCAATTATTTTATG

TGTAGTAAAAAAAAAGCAACTGATGCAGCTGTGT

TAAGGAGCCAAAGACAATAGGAGGCACTGGTAAAT

TTTGGCCTCTCTCAAACTAAAATTTTCGTGTATTT

CCCCCCCAAATTATAAAAACATAACTAGAAAATAT

TAAAAGGTCATATCAGATTATTAACATTATATATT

CATTAAAGGCAGCTTTAGGAAACAGGAATATACTA

CAAGAGTGTTTTGTTTGTGTATACAAATCATTCCA

TTTTTAAATGGCACAGATGCTTAAGGGCTATAAAA

ACTTCTAATTTCTTATAAATATGTTAGCACTTTTT

TTAAGTTAGTGATTACAGTTTACCTACTGTATAGA

ATAATTTTCTAATAATGGATGGTATTCTAAAACTC

AATTGAGGCATTCACATTTTAAAGAAAGTATTGTC

TTTCACCTTTTATGTGTTCTTTTTGCAAAAATCTA

CAAAGTGACAGCTGTGTTCAGAGCTTAGATCCCAA

AAACGTGATCTCTTTTAGTTACTATCTGGGCAGAT

GGTAGTATATCTAATGAAATGGTGATTAATTTAAA

TGTATAATCTGGAAATATGTAAAACTTGAAGTATT

TTTTGTCCAGGCAAAGGTACTCATTGGGCCTCAGT

TTCTTCATCTCTAAAATGGAGTGGATGAGATGATG

TGATAACTGCAGTCCCTTCTAACTCTTAAATTCTT

TTCATTCTCACAGATTCACTCTATCATTATTGTTA

TTCATGTAAGAAACGTTTTAGGGAGAAAAATTACA

CTTTAAAATTAATTTAGTTTTCTATACAGTTGTTT

TCTTTACTCTTGAAAAGTTATGACAGCTTTAACGT

CTCTTGTCTTCTGTAATTTTTATTTCTAAACTCC

TATCATTTCCAAGCTTTAACTGTACTTTATCAGAG

CCTTCATTTCTGGTATGTGTTATATGCCCTCAATG

TATTCACTGACTGTTCTGTAATTTCAGTTTGTCTG

TTCCTTGTCAGAATGTTTCAAGTAAAATAAAAAAT

TAAATGTA
```

RPGR<sup>ORF15</sup> amino acid sequence

SEQ ID NO: 17)
```
MREPEELMPDSGAVFTFGKSKFAENNPGKFWFKND

VPVHLSCGDEHSAVVTGNNKLYMFGSNNWGQLGLG

SKSAISKPTCVKALKPEKVKLAACGRNHTLVSTEG
```

-continued
```
GNVYATGGNNEGQLGLGDTEERNTFHVISFFTSEH

KIKQLSAGSNTSAALTEDGRLFMWGDNSEGQIGLK

NVSNVCVPQQVTIGKPVSWISCGYYHSAFVTTDGE

LYVFGEPENGKLGLPNQLLGNHRTPQLVSEIPEKV

IQVACGGEHTVVLTENAVYTFGLGQFGQLGLGTFL

FETSEPKVIENIRDQTISYISCGENHTALITDIGL

MYTFGDGRHGKLGLGLENFTNHFIPTLCSNFLRFI

VKLVACGGCHMVVFAAPHRGVAKEIEFDEINDTCL

SVATFLPYSSLTSGNVLQRTLSARMRRRERERSPD

SFSMRRTLPPIEGTLGLSACFLPNSVFPRCSERNL

QESVLSEQDLMQPEEPDYLLDEMTKEAEIDNSSTV

ESLGETTDILNMTHIMSLNSNEKSLKLSPVQKQKK

QQTIGELTQDTALTENDDSDEYEEMSEMKEGKACK

QHVSQGIFMTQPATTIEAFSDEEVATTIEAFSDEE

VEIPEEKEGAEDSKGNGIEEQEVEANEENVKVHGG

RKEKTEILSDDLTDKAEVSEGKAKSVGEAEDGPEG

RGDGTCEEGSSGAEHWQDEEREKGEKDKGRGEMER

PGEGEKELAEKEEWKKRDGEEQEQKEREQGHQKER

NQEMEEGGEEEHGEGEEEEGDREEEEEKEGEGKEE

GEGEEVEGEREKEEGERKKEERAGKEEKGEEEGDQ

GEGEEEETEGRGEEKEEGGEVEGGEVEEGKGEREE

EEEEGEGEEEEGEGEEEEGEGEEEEGEGKGEEEGE

EGEGEEEGEEGEGEGEEEEGEGEGEEEGEGEGEEE

EGEGEGEEEGEGEGEEEEGEGKGEEEGEEGEGEGE

EEEGEGEGEDGEGEGEEEEGEWEGEEEEGEGEGEE

EGEGEEGEEGEGEGEEEEGEGEGEEEEGEEEGEEEG

EGEEEGEGEGEEEEGEVEGEVEGEEGEGEGEEEE

GEEEGEEREKEGEGEENRRNREEEEEEEGKYQETG

EEENERQDGEEYKKVSKIKGSVKYGKHKTYQKKSV

TNTQGNGKEQRSKMPVQSKRLLKNGPSGSKKFWNN

VLPHYLELK*
```

RPGR<sup>ORF15</sup> nucleic acid sequence

SEQ ID NO: 18)
```
ATGAGGGAGCCGGAAGAGCTGATGCCCGATTCGGG

TGCTGTGTTTACATTTGGGAAAAGTAAATTTGCTG

AAAATAATCCCGGTAAATTCTGGTTTAAAAATGAT

GTCCCTGTACATCTTTCATGTGGAGATGAACATTC

TGCTGTTGTTACCGGAAATAATAAACTTTACATGT

TTGGCAGTAACAACTGGGGTCAGTTAGGATTAGGA

TCAAAGTCAGCCATCAGCAAGCCAACATGTGTCAA

AGCTCTAAAACCTGAAAAGTGAAATTAGCTGCCT

GTGGAAGGAACCACACCCTGGTGTCAACAGAAGGA
```

51

GGCAATGTATATGCAACTGGTGGAAATAATGAAGG

ACAGTTGGGGCTTGGTGACACCGAAGAAAGAAACA

CTTTTCATGTAATTAGCTTTTTTACATCCGAGCAT

AAGATTAAGCAGCTGTCTGCTGGATCTAATACTTC

AGCTGCCCTAACTGAGGATGGAAGACTTTTTATGT

GGGGTGACAATTCCGAAGGGCAAATTGGTTTAAAA

AATGTAAGTAATGTCTGTGTCCCTCAGCAAGTGAC

CATTGGGAAACCTGTCTCCTGGATCTCTTGTGGAT

ATTACCATTCAGCTTTTGTAACAACAGATGGTGAG

CTATATGTGTTTGGAGAACCTGAGAATGGGAAGTT

AGGTCTTCCCAATCAGCTCCTGGGCAATCACAGAA

CACCCCAGCTGGTGTCTGAAATTCCGGAGAAGGTG

ATCCAAGTAGCCTGTGGTGGAGAGCATACTGTGGT

TCTCACGGAGAATGCTGTGTATACCTTTGGGCTGG

GACAATTTGGTCAGCTGGGTCTTGGCACTTTTCTT

TTTGAAACTTCAGAACCCAAAGTCATTGAGAATAT

TAGGGATCAAACAATAAGTTATATTTCTTGTGGAG

AAAATCACACAGCTTTGATAACAGATATCGGCCTT

ATGTATACTTTTGGAGATGGTCGCCACGGAAAATT

AGGACTTGGACTGGAGAATTTTACCAATCACTTCA

TTCCTACTTTGTGCTCTAATTTTTTGAGGTTTATA

GTTAAATTGGTTGCTTGTGGTGGATGTCACATGGT

AGTTTTTGCTGCTCCTCATCGTGGTGTGGCAAAAG

AAATTGAATTCGATGAAATAAATGATACTTGCTTA

TCTGTGGCGACTTTTCTGCCGTATAGCAGTTTAAC

CTCAGGAAATGTACTGCAGAGGACTCTATCAGCAC

GTATGCGGCGAAGAGAGAGGGAGAGGTCTCCAGAT

TCTTTTTCAATGAGGAGAACACTACCTCCAATAGA

AGGGACTCTTGGCCTTTCTGCTTGTTTTCTCCCCA

ATTCAGTCTTTCCACGATGTTCTGAGAGAAACCTC

CAAGAGAGTGTCTTATCTGAACAGGACCTCATGCA

GCCAGAGGAACCAGATTATTTGCTAGATGAAATGA

CCAAAGAAGCAGAGATAGATAATTCTTCAACTGTA

GAAAGCCTTGGAGAAACTACTGATATCTTAAACAT

GACACACATCATGAGCCTGAATTCCAATGAAAAGT

CATTAAAATTATCACCAGTTCAGAAACAAAAGAAA

CAACAAACAATTGGGGAACTGACGCAGGATACAGC

TCTTACTGAAAACGATGATAGTGATGAATATGAAG

AAATGTCAGAAATGAAAGAAGGGAAAGCATGTAAA

CAACATGTGTCACAAGGGATTTTCATGACGCAGCC

52

AGCTACGACTATCGAAGCATTTTCAGATGAGGAAG

TAGCTACGACTATCGAAGCATTTTCAGATGAGGAA

GTAGAGATCCCAGAGGAGAAGGAAGGAGCAGAGGA

TTCAAAAGGAAATGGAATAGAGGAGCAAGAGGTAG

AAGCAAATGAGGAAAATGTGAAGGTGCATGGAGGA

AGAAAGGAGAAAACAGAGATCCTATCAGATGACCT

TACAGACAAAGCAGAGGTGAGTGAAGGCAAGGCAA

AATCAGTGGGAGAAGCAGAGGATGGGCCTGAAGGT

AGAGGGGATGGAACCTGTGAGGAAGGTAGTTCAGG

AGCAGAACACTGGCAAGATGAGGAGAGGGAGAAGG

GGGAGAAAGACAAGGGTAGAGGAGAAATGGAGAGG

CCAGGAGAGGGGAGAGAAGGAACTAGCAGAGAAGGA

AGAATGGAAGAAGAGGGATGGGGAAGAGCAGGAGC

AAAAGGAGAGGGAGCAGGGCCATCAGAAGGAAAGA

AACCAAGAGATGGAGGAGGGAGGGGAGGAGGAGCA

TGGAGAAGGAGAAGAAGAGGAGGGAGACAGAGAAG

AGGAAGAAGAGAAGGAGGGGAGAAGGGAAAGAGGAA

GGAGAAGGGGAAGAAGTGGAGGGGAGAACGTGAAAA

GGAGGAAGGAGAGAGGAAAAAGGAGGAAAGAGCGG

GGAAGGAGGAGAAAGGAGAGGAAGAAGGAGACCAA

GGAGAGGGGGAAGAGGAGGAAACAGAGGGGAGAGG

GGAGGAAAAAGAGGAGGGAGGGGAAGTAGAGGGAG

GGGAAGTAGAGGAGGGGAAAGGAGAGAGGGAAGAG

GAAGAGGAGGAGGGTGAGGGGGAAGAGGAGGAAGG

GGAGGGGGAAGAGGAGGAAGGGGAGGGGGAAGAGG

AGGAAGGAGAAGGGAAAGGGGAGGAAGAAGGGGAA

GAAGGAGAAGGGGAGGAAGAAGGGGAGGAAGGAGA

AGGGGAGGGGAAGAGGAGGAAGGAGAAGGGGAGG

GAGAAGAGGAAGGAGAAGGGGAGGGAGAAGAGGAG

GAAGGAGAAGGGGAGGGAGAAGAGGAAGGAGAAGG

GGAGGGAGAAGAGGAGGAAGGAGAAGGGAAAGGGG

AGGAGGAAGGAGAGGAAGGAGAAGGGGAGGGGGAA

GAGGAGGAAGGAGAAGGGGAAGGGGAGGATGGAGA

AGGGGAGGGGAAGAGGAGGAAGGAGAATGGGAGG

GGGAAGAGGAGGAAGGAGAAGGGGAGGGGGAAGAG

GAAGGAGAAGGGGAAGGGGAGGAAGGAGAAGGGGA

GGGGGAAGAGGAGGAAGGAGAAGGGGAGGGGGAAG

AGGAGGAAGGGGAAGAAGAAGGGGAGGAAGAAGGA

GAGGGAGAGGAAGAAGGGGAGGGAGAAGGGGAGGA

AGAAGAGGAAGGGGAAGTGGAAGGGGAGGTGGAAG

GGGAGGAAGGAGAGGGGGAAGGAGAGGAAGAGGAA

53

-continued

```
GGAGAGGAGGAAGGAGAAGAAAGGGAAAAGGAGGG

GGAAGGAGAAGAAAACAGGAGGAACAGAGAAGAGG

AGGAGGAAGAAGAGGGGAAGTATCAGGAGACAGGC

GAAGAAGAGAATGAAAGGCAGGATGGAGAGGAGTA

CAAAAAAGTGAGCAAAATAAAAGGATCTGTGAAAT

ATGGCAAACATAAAACATATCAAAAAAAGTCAGTT

ACTAACACACAGGGAAATGGGAAAGAGCAGAGGTC

CAAAATGCCAGTCCAGTCAAAACGACTTTTAAAAA

ACGGGCCATCAGGTTCCAAAAAGTTCTGGAATAAT

GTATTACCACATTACTTGGAATTGAAGTAA
```

REFERENCES

1 Singla, V. and Reiter, J. F. (2006) The primary cilium as the cell's antenna: signaling at a sensory organelle. Science, 313, 629-633.

2 Pazour, G. J. and Rosenbaum, J. L. (2002) Intraflagellar transport and cilia-dependent diseases. Trends Cell Biol, 12, 551-555.

3 Baker, S. A., Freeman, K., Luby-Phelps, K., Pazour, G. J. and Besharse, J. C. (2003) IFT20 links kinesin II with a mammalian intraflagellar transport complex that is conserved in motile flagella and sensory cilia. J Biol Chem, 278, 34211-34218.

4 Khanna, H. (2015) Photoreceptor Sensory Cilium: Traversing the Ciliary Gate. Cells, 4, 674-686.

5 Chen, H. Y., Kelley, R. A., Li, T. and Swaroop, A. (2020) Primary cilia biogenesis and associated retinal ciliopathies. Semin Cell Dev Biol.

6 Badano, J. L., Leitch, C. C., Ansley, S. J., May-Simera, H., Lawson, S., Lewis, R. A., Beales, P. L., Dietz, H. C., Fisher, S. and Katsanis, N. (2006) Dissection of epistasis in oligogenic Bardet-Biedl syndrome. Nature, 439, 326-330.

7 Besharse, J. C. (1986) The Retina: A Model for Cell Biological Studies Part I. Academic, New York.

8 Arts, H. H., Doherty, D., van Beersum, S. E., Parisi, M. A., Letteboer, S. J., Gorden, N. T., Peters, T. A., Marker, T., Voesenek, K., Kartono, A. et al. (2007) Mutations in the gene encoding the basal body protein RPGRIP1L, a nephrocystin-4 interactor, cause Joubert syndrome. Nat Genet, 39, 882-888.

9 Berson, E. L. (1996) Retinitis pigmentosa: unfolding its mystery. Proc Natl Acad Sci USA, 93, 4526-4528.

10 Bird, A. C. (1987) Clinical investigation of retinitis pigmentosa. Progress in clinical and biological research, 247, 3-20.

11 Hanany, M., Rivolta, C. and Sharon, D. (2020) Worldwide carrier frequency and genetic prevalence of autosomal recessive inherited retinal diseases. Proceedings of the National Academy of Sciences of the United States of America, 117, 2710-2716.

12 Churchill, J. D., Bowne, S. J., Sullivan, L. S., Lewis, R. A., Wheaton, D. K., Birch, D. G., Branham, K. E., Heckenlively, J. R. and Daiger, S. P. (2013) Mutations in the X-linked retinitis pigmentosa genes RPGR and RP2 found in 8.5% of families with a provisional diagnosis of autosomal dominant retinitis pigmentosa. Investigative ophthalmology & visual science, 54, 1411-1416.

13 Breuer, D. K., Yashar, B. M., Filippova, E., Hiriyanna, S., Lyons, R. H., Mears, A. J., Asaye, B., Acar, C., Vervoort, R., Wright, A. F. et al. (2002) A comprehensive mutation analysis of RP2 and RPGR in a North American cohort of families with X-linked retinitis pigmentosa. Am J Hum Genet, 70, 1545-1554.

14 Sharon, D., Sandberg, M. A., Rabe, V. W., Stillberger, M., Dryja, T. P. and Berson, E. L. (2003) RP2 and RPGR mutations and clinical correlations in patients with X-linked retinitis pigmentosa. Am J Hum Genet, 73, 1131-1146.

15 Ayyagari, R., Demirci, F. Y., Liu, J., Bingham, E. L., Stringham, H., Kakuk, L. E., Boehnke, M., Gorin, M. B., Richards, J. E. and Sieving, P. A. (2002) X-linked recessive atrophic macular degeneration from RPGR mutation. Genomics, 80, 166-171.

16 Hunter, D. G., Fishman, G. A. and Kretzer, F. L. (1988) Abnormal axonemes in X-linked retinitis pigmentosa. Archives of ophthalmology, 106, 362-368.

17 Iannaccone, A., Breuer, D. K., Wang, X. F., Kuo, S. F., Normando, E. M., Filippova, E., Baldi, A., Hiriyanna, S., MacDonald, C. B., Baldi, F. et al. (2003) Clinical and immunohistochemical evidence for an X linked retinitis pigmentosa syndrome with recurrent infections and hearing loss in association with an RPGR mutation. J Med Genet, 40, e118.

18 Koenekoop, R. K., Loyer, M., Hand, C. K., Al Mandi, H., Dembinska, O., Beneish, R., Racine, J. and Rouleau, G. A. (2003) Novel RPGR mutations with distinct retinitis pigmentosa phenotypes in French-Canadian families. American journal of ophthalmology, 136, 678-687.

19 Bukowy-Bieryllo, Z., Zietkiewicz, E., Loges, N. T., Wittmer, M., Geremek, M., Olbrich, H., Fliegauf, M., Voelkel, K., Rutkiewicz, E., Rutland, J. et al. (2013) RPGR mutations might cause reduced orientation of respiratory cilia. Pediatr Pulmonol, 48, 352-363.

20 Meindl, A., Dry, K., Herrmann, K., Manson, F., Ciccodicola, A., Edgar, A., Carvalho, M. R., Achatz, H., Hellebrand, H., Lennon, A. et al. (1996) A gene (RPGR) with homology to the RCC1 guanine nucleotide exchange factor is mutated in X-linked retinitis pigmentosa (RP3). Nature genetics, 13, 35-42.

21 Roepman, R., van Duijnhoven, G., Rosenberg, T., Pinckers, A. J., Bleeker-Wagemakers, L. M., Bergen, A. A., Post, J., Beck, A., Reinhardt, R., Ropers, H. H. et al. (1996) Positional cloning of the gene for X-linked retinitis pigmentosa 3: homology with the guanine-nucleotide-exchange factor RCC1. Hum. Mol. Genet., 5, 1035-1041.

22 Mears, A. J., Hiriyanna, S., Vervoort, R., Yashar, B., Gieser, L., Fahrner, S., Daiger, S. P., Heckenlively, J. R., Sieving, P. A., Wright, A. F. et al. (2000) Remapping of the RP15 locus for X-linked cone-rod degeneration to Xp11.4-p21.1, and identification of a de novo insertion in the RPGR exon $^{ORF15}$. American journal of human genetics, 67, 1000-1003.

23 He, S., Parapuram, S. K., Hurd, T. W., Behnam, B., Margolis, B., Swaroop, A. and Khanna, H. (2008) Retinitis Pigmentosa GTPase Regulator (RPGR) protein isoforms in mammalian retina: Insights into X-linked Retinitis Pigmentosa and associated ciliopathies. Vision research, 48, 366-376.

24 Rao, K. N., Zhang, W., Li, L., Ronquillo, C., Baehr, W. and Khanna, H. (2016) Ciliopathy-associated protein CEP290 modifies the severity of retinal degeneration due to loss of RPGR. Hum Mol Genet, 25, 2005-2012.

25 Lee, J. J. and Seo, S. (2015) PDE6D binds to the C-terminus of RPGR in a prenylation-dependent manner. EMBO Rep.

26 Vervoort, R. and Wright, A. F. (2002) Mutations of RPGR in X-linked retinitis pigmentosa (RP3). Hum Mutat, 19, 486-500.

27 Hosch, J., Lorenz, B. and Stieger, K. (2011) RPGR: role in the photoreceptor cilium, human retinal disease, and gene therapy. Ophthalmic Genet, 32, 1-11.

28 Schlegel, J., Hoffmann, J., Roll, D., Muller, B., Gunther, S., Zhang, W., Janise, A., Vossing, C., Fuhler, B., Neidhardt, J. et al. (2019) Toward genome editing in X-linked RP-development of a mouse model with specific treatment relevant features. Transl Res, 203, 57-72.

29 Zhang, Q., Acland, G. M., Wu, W. X., Johnson, J. L., Pearce-Kelling, S., Tulloch, B., Vervoort, R., Wright, A. F. and Aguirre, G. D. (2002) Different RPGR exon $^{ORF15}$ mutations in Canids provide insights into photoreceptor cell degeneration. Hum. Mol. Genet., 11, 993-1003.

30 Rao, K. N., Li, L., Anand, M. and Khanna, H. (2015) Ablation of retinal ciliopathy protein RPGR results in altered photoreceptor ciliary composition. Sci Rep, 5, 11137.

31 Hong, D. H., Pawlyk, B. S., Shang, J., Sandberg, M. A., Berson, E. L. and Li, T. (2000) A retinitis pigmentosa GTPase regulator (RPGR)-deficient mouse model for X-linked retinitis pigmentosa (RP3). Proc Natl Acad Sci USA, 97, 3649-3654.

32 Rao, K. N., Zhang, W., Li, L., Anand, M. and Khanna, H. (2016) Prenylated retinal ciliopathy protein RPGR interacts with PDE6delta and regulates ciliary localization of Joubert syndrome-associated protein INPP5E. Hum. Mol. Genet. 25, 4533-4545.

33 Charng, J., Cideciyan, A. V., Jacobson, S. G., Sumaroka, A., Schwartz, S. B., Swider, M., Roman, A. J., Sheplock, R., Anand, M., Peden, M. C. et al. (2016) Variegated yet non-random rod and cone photoreceptor disease patterns in RPGR-$^{ORF15}$-associated retinal degeneration. Hum. Mol. Genet., 25, 5444-5459.

34 Huang, W. C., Wright, A. F., Roman, A. J., Cideciyan, A. V., Manson, F. D., Gewaily, D. Y., Schwartz, S. B., Sadigh, S., Limberis, M. P., Bell, P. et al. (2012) RPGR-associated retinal degeneration in human X-linked RP and a murine model. Investigative ophthalmology & visual science, 53, 5594-5608.

35 den Hollander, A. I., Koenekoop, R. K., Yzer, S., Lopez, I., Arends, M. L., Voesenek, K. E., Zonneveld, M. N., Strom, T. M., Meitinger, T., Brunner, H. G. et al. (2006) Mutations in the CEP290 (NPHP6) gene are a frequent cause of Leber congenital amaurosis. Am J Hum Genet, 79, 556-561.

36 den Hollander, A. I., Roepman, R., Koenekoop, R. K. and Cremers, F. P. (2008) Leber congenital amaurosis: genes, proteins and disease mechanisms. Prog Retin Eye Res, 27, 391-419.

37 Sayer, J. A., Otto, E. A., O'Toole J, F., Nurnberg, G., Kennedy, M. A., Becker, C., Hennies, H. C., Helou, J., Attanasio, M., Fausett, B. V. et al. (2006) The centrosomal protein nephrocystin-6 is mutated in Joubert syndrome and activates transcription factor ATF4. Nat Genet, 38, 674-681.

38 Rachel, R. A., Yamamoto, E. A., Dewanjee, M. K., May-Simera, H. L., Sergeev, Y. V., Hackett, A. N., Pohida, K., Munasinghe, J., Gotoh, N., Wickstead, B. et al. (2015) CEP290 alleles in mice disrupt tissue-specific cilia biogenesis and recapitulate features of syndromic ciliopathies. Hum Mol Genet, 24, 3775-3791.

39 Shimada, H., Lu, Q., Insinna-Kettenhofen, C., Nagashima, K., English, M. A., Semler, E. M., Mahgerefteh, J., Cideciyan, A. V., Li, T., Brooks, B. P. et al. (2017) In Vitro Modeling Using Ciliopathy-Patient-Derived Cells Reveals Distinct Cilia Dysfunctions Caused by CEP290 Mutations. Cell Rep, 20, 384-396.

40 van Dijk, J., Miro, J., Strub, J. M., Lacroix, B., van Dorsselaer, A., Edde, B. and Janke, C. (2008) Polyglutamylation is a post-translational modification with a broad range of substrates. The Journal of biological chemistry, 283, 3915-3922.

41 Rao, K. N., Anand, M. and Khanna, H. (2016) The carboxyl terminal mutational hotspot of the ciliary disease protein RPGR$^{ORF15}$ (retinitis pigmentosa GTPase regulator) is glutamylated in vivo. Biol Open, 5, 424-428.

42 Beltran, W. A., Cideciyan, A. V., Lewin, A. S., Iwabe, S., Khanna, H., Sumaroka, A., Chiodo, V. A., Fajardo, D. S., Roman, A. J., Deng, W. T. et al. (2012) Gene therapy rescues photoreceptor blindness in dogs and paves the way for treating human X-linked retinitis pigmentosa. Proc Natl Acad Sci USA, 109, 2132-2137.

43 Pawlyk, B. S., Bulgakov, O. V., Sun, X., Adamian, M., Shu, X., Smith, A. J., Berson, E. L., Ali, R. R., Khani, S., Wright, A. F. et al. (2015) Photoreceptor rescue by an abbreviated human RPGR gene in a murine model of X-linked retinitis pigmentosa. Gene therapy.

44 El-Brolosy, M. A., Kontarakis, Z., Rossi, A., Kuenne, C., Gunther, S., Fukuda, N., Kikhi, K., Boezio, G. L. M., Takacs, C. M., Lai, S. L. et al. (2019) Genetic compensation triggered by mutant mRNA degradation. Nature, 568, 193-197.

45 Rossi, A., Kontarakis, Z., Gerri, C., Nolte, H., Holper, S., Kruger, M. and Stainier, D. Y. (2015) Genetic compensation induced by deleterious mutations but not gene knockdowns. Nature, 524, 230-233.

46 Tautz, D. (2000) A genetic uncertainty problem. Trends Genet, 16, 475-477.

47 Hong, D. H., Pawlyk, B. S., Adamian, M. and Li, T. (2004) Dominant, gain-of-function mutant produced by truncation of RPGR. Investigative ophthalmology & visual science, 45, 36-41.

48 Wright, R. N., Hong, D. H. and Perkins, B. (2011) Misexpression of the constitutive Rpgr$^{(ex1-19)}$ variant leads to severe photoreceptor degeneration. Investigative ophthalmology & visual science, 52, 5189-5201.

49 Gakovic, M., Shu, X., Kasioulis, I., Carpanini, S., Moraga, I. and Wright, A. F. (2011) The role of RPGR in cilia formation and actin stability. Hum. Mol. Genet., 20, 4840-4850.

50 Ghosh, A. K., Murga-Zamalloa, C. A., Chan, L., Hitchcock, P. F., Swaroop, A. and Khanna, H. (2010) Human retinopathy-associated ciliary protein retinitis pigmentosa GTPase regulator mediates cilia-dependent vertebrate development. Hum. Mol. Genet., 19, 90-98.

51 Murga-Zamalloa, C. A., Atkins, S. J., Peranen, J., Swaroop, A. and Khanna, H. (2010) Interaction of retinitis pigmentosa GTPase regulator (RPGR) with RAB8A GTPase: implications for cilia dysfunction and photoreceptor degeneration. Hum Mol Genet, 19, 3591-3598.

52 Shu, X., Zeng, Z., Gautier, P., Lennon, A., Gakovic, M., Patton, E. E. and Wright, A. F. (2010) Zebrafish Rpgr is required for normal retinal development and plays a role in dynein-based retrograde transport processes. Hum. Mol. Genet., 19, 657-670.

53 Yadav, S. P., Sharma, N. K., Liu, C., Dong, L., Li, T. and Swaroop, A. (2016) Centrosomal protein CP110 controls maturation of the mother centriole during cilia biogenesis. Development, 143, 1491-1501.

54 Cehajic-Kapetanovic, J., Xue, K., Martinez-Fernandez de la Camara, C., Nanda, A., Davies, A., Wood, L. J., Salvetti, A. P., Fischer, M. D., Aylward, J. W., Barnard, A. R. et al. (2020) Initial results from a first-in-human gene therapy trial on X-linked retinitis pigmentosa caused by mutations in RPGR. Nature medicine, 26, 354-359.

55 Ratnadiwakara, M.a.A., M-L. (2018) mRNA Stability Assay Using Transcription Inhibition by Actinomycin D in Mouse Pluripotent Stem Cells. Bio-Protocol, 8, e3072.

---

What is claimed is:

1. An isolated nucleic acid comprising an expression cassette that comprises a first region that encodes an inhibitory nucleic acid a miRNA or an artificial miRNA (amiRNA), the first region comprising a first strand that comprises SEQ ID NO 7 and a second strand that comprises SEQ ID NO 8.

2. The isolated nucleic acid of claim 1, wherein the expression cassette further comprises a second region encoding an RPGR$^{ORF15}$ protein comprising the amino acid sequence set forth in SEQ ID NO: 15 or SEQ ID NO: 17.

3. The isolated nucleic acid of claim 1, wherein the expression cassette is flanked by adeno associated virus (AAV) inverted terminal repeats (ITRs).

4. A recombinant adeno-associated virus (rAAV) comprising:

(i) the isolated nucleic acid of claim 1; and (ii) at least one AAV capsid protein.

5. The rAAV of claim 4, wherein the capsid protein is of a serotype selected from: AAV1, AAV2, AAV3, AAV4, AAV5, AAV6, AAV7, AAV8, AAV9, and AAVrh.10.

6. The isolated nucleic acid of claim 1, wherein the first region encodes an amiRNA.

7. The isolated nucleic acid of claim 1, wherein the first region further comprises a first promoter operably linked to the sequence encoding the miRNA or the amiRNA.

8. The isolated nucleic acid of claim 7, wherein the first promoter is a constitutive promoter, inducible promoter, or tissue-specific promoter.

9. The isolated nucleic acid of claim 7 or claim 8, wherein the first promoter is an RNA polymerase III (pol III) promoter.

10. The isolated nucleic acid of claim 9, wherein the pol III promoter is a U6 promoter or an H1 promoter.

11. The isolated nucleic acid of claim 2, wherein the RPGR$^{ORF15}$ protein is encoded by the nucleic acid sequence set forth in any one of SEQ ID NO: 16 or 18.

12. The isolated nucleic acid of claim 2 or 11, wherein the second region comprises a second promoter operably linked to the sequence encoding the RPGR$^{ORF15}$ protein.

13. The isolated nucleic acid of claim 12, wherein the second promoter is a constitutive promoter, inducible promoter, or tissue-specific promoter.

14. The isolated nucleic acid of claim 12, wherein the second promoter is an RNA polymerase II (pol II) promoter.

15. A plasmid comprising the isolated nucleic acid of claim 1.

16. A host cell comprising the isolated nucleic acid of claim 1.

17. The isolated nucleic acid of claim 13, wherein the second promoter is an RNA polymerase II (pol II) promoter.

* * * * *

SEQUENCE LISTING

```
<160> NUMBER OF SEQ ID NOS: 36

<210> SEQ ID NO 1
<211> LENGTH: 25
<212> TYPE: RNA
<213> ORGANISM: Artificial Sequence
<220> FEATURE:
<223> OTHER INFORMATION: Synthetic

<400> SEQUENCE: 1
cuuccucucu uucucucccu uguga                                          25

<210> SEQ ID NO 2
<211> LENGTH: 27
<212> TYPE: RNA
<213> ORGANISM: Artificial Sequence
<220> FEATURE:
<223> OTHER INFORMATION: Synthetic

<400> SEQUENCE: 2
aggaaggaga gaaagagagg gaacacu                                        27

<210> SEQ ID NO 3
<211> LENGTH: 25
<212> TYPE: RNA
<213> ORGANISM: Artificial Sequence
<220> FEATURE:
<223> OTHER INFORMATION: Synthetic

<400> SEQUENCE: 3
caccaagcaa agacaugaaa aaaac                                          25

<210> SEQ ID NO 4
<211> LENGTH: 27
<212> TYPE: RNA
<213> ORGANISM: Artificial Sequence
<220> FEATURE:
<223> OTHER INFORMATION: Synthetic

<400> SEQUENCE: 4
uugugguucg uuucuguacu uuuuuug                                        27

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
ggagcagaaa gaaccaauga ugata                                          25

<210> SEQ ID NO 6
<211> LENGTH: 27
<212> TYPE: RNA
<213> ORGANISM: Artificial Sequence
```

-continued

```
<220> FEATURE:
<223> OTHER INFORMATION: Synthetic

<400> SEQUENCE: 6
uuccucgucu uucuugguua cuacuau                                      27

<210> SEQ ID NO 7
<211> LENGTH: 25
<212> TYPE: RNA
<213> ORGANISM: Artificial Sequence
<220> FEATURE:
<223> OTHER INFORMATION: Synthetic

<400> SEQUENCE: 7
aucaaaagau ugucaagaau aacaa                                        25

<210> SEQ ID NO 8
<211> LENGTH: 27
<212> TYPE: RNA
<213> ORGANISM: Artificial Sequence
<220> FEATURE:
<223> OTHER INFORMATION: Synthetic

<400> SEQUENCE: 8
uuuaguuuuc uaacaguucu uauuguu                                      27

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
tcggcatctt tattatcact t                                            21

<210> SEQ ID NO 10
<211> LENGTH: 69
<212> TYPE: RNA
<213> ORGANISM: Artificial Sequence
<220> FEATURE:
<223> OTHER INFORMATION: Synthetic

<400> SEQUENCE: 10
ugcugucggc aucuuuauua ucacuuguuu uggccacuga cugacaagug auaaaagaug   60
ccgacagga                                                          69

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
tcccacagtt ttcttcttgc t                                            21

<210> SEQ ID NO 12
<211> LENGTH: 69
<212> TYPE: RNA
<213> ORGANISM: Artificial Sequence
<220> FEATURE:
<223> OTHER INFORMATION: Synthetic

<400> SEQUENCE: 12
```

-continued

```
ugcuguccca caguuuauuu cuugcuguuu uggccacuga cugacagcaa gaaaaacugu        60
gggacagga                                                               69

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
ttcaagtaat ccaggatagg ct                                                22

<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
aagcccttac cccaaaaagt at                                                22

<210> SEQ ID NO 15
<211> LENGTH: 1152
<212> TYPE: PRT
<213> ORGANISM: Artificial Sequence
<220> FEATURE:
<223> OTHER INFORMATION: Synthetic

<400> SEQUENCE: 15

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
        50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
            100                 105                 110

Gly Asn Asn Glu Gly Gln Leu Gly Leu Gly Asp Thr Glu Glu Arg Asn
        115                 120                 125

Thr Phe His Val Ile Ser Phe Phe Thr Ser Glu His Lys Ile Lys Gln
    130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
            180                 185                 190

Ser Trp Ile Ser Cys Gly Tyr Tyr His Ser Ala Phe Val Thr Thr Asp
        195                 200                 205

Gly Glu Leu Tyr Val Phe Gly Glu Pro Glu Asn Gly Lys Leu Gly Leu
    210                 215                 220
```

-continued

```
Pro Asn Gln Leu Leu Gly Asn His Arg Thr Pro Gln Leu Val Ser Glu
225             230             235             240

Ile Pro Glu Lys Val Ile Gln Val Ala Cys Gly Gly Glu His Thr Val
                245             250             255

Val Leu Thr Glu Asn Ala Val Tyr Thr Phe Gly Leu Gly Gln Phe Gly
        260             265             270

Gln Leu Gly Leu Gly Thr Phe Leu Phe Glu Thr Ser Glu Pro Lys Val
        275             280             285

Ile Glu Asn Ile Arg Asp Gln Thr Ile Ser Tyr Ile Ser Cys Gly Glu
        290             295             300

Asn His Thr Ala Leu Ile Thr Asp Ile Gly Leu Met Tyr Thr Phe Gly
305             310             315             320

Asp Gly Arg His Gly Lys Leu Gly Leu Gly Leu Glu Asn Phe Thr Asn
                325             330             335

His Phe Ile Pro Thr Leu Cys Ser Asn Phe Leu Arg Phe Ile Val Lys
                340             345             350

Leu Val Ala Cys Gly Gly Cys His Met Val Val Phe Ala Ala Pro His
        355             360             365

Arg Gly Val Ala Lys Glu Ile Glu Phe Asp Glu Ile Asn Asp Thr Cys
        370             375             380

Leu Ser Val Ala Thr Phe Leu Pro Tyr Ser Ser Leu Thr Ser Gly Asn
385             390             395             400

Val Leu Gln Arg Thr Leu Ser Ala Arg Met Arg Arg Arg Glu Arg Glu
                405             410             415

Arg Ser Pro Asp Ser Phe Ser Met Arg Arg Thr Leu Pro Pro Ile Glu
                420             425             430

Gly Thr Leu Gly Leu Ser Ala Cys Phe Leu Pro Asn Ser Val Phe Pro
        435             440             445

Arg Cys Ser Glu Arg Asn Leu Gln Glu Ser Val Leu Ser Glu Gln Asp
        450             455             460

Leu Met Gln Pro Glu Glu Pro Asp Tyr Leu Leu Asp Glu Met Thr Lys
465             470             475             480

Glu Ala Glu Ile Asp Asn Ser Ser Thr Val Glu Ser Leu Gly Glu Thr
                485             490             495

Thr Asp Ile Leu Asn Met Thr His Ile Met Ser Leu Asn Ser Asn Glu
        500             505             510

Lys Ser Leu Lys Leu Ser Pro Val Gln Lys Gln Lys Gln Gln Thr
        515             520             525

Ile Gly Glu Leu Thr Gln Asp Thr Ala Leu Thr Glu Asn Asp Asp Ser
        530             535             540

Asp Glu Tyr Glu Glu Met Ser Glu Met Lys Glu Gly Lys Ala Cys Lys
545             550             555             560

Gln His Val Ser Gln Gly Ile Phe Met Thr Gln Pro Ala Thr Thr Ile
                565             570             575

Glu Ala Phe Ser Asp Glu Glu Val Glu Ile Pro Glu Glu Lys Glu Gly
                580             585             590

Ala Glu Asp Ser Lys Gly Asn Gly Ile Glu Glu Gln Glu Val Glu Ala
        595             600             605

Asn Glu Glu Asn Val Lys Val His Gly Gly Arg Lys Glu Lys Thr Glu
        610             615             620

Ile Leu Ser Asp Asp Leu Thr Asp Lys Ala Glu Val Ser Glu Gly Lys
625             630             635             640
```

-continued

```
Ala Lys Ser Val Gly Glu Ala Glu Asp Gly Pro Glu Gly Arg Gly Asp
            645                 650                 655

Gly Thr Cys Glu Glu Gly Ser Ser Gly Ala Glu His Trp Gln Asp Glu
            660                 665                 670

Glu Arg Glu Lys Gly Glu Lys Asp Lys Gly Arg Gly Glu Met Glu Arg
        675                 680                 685

Pro Gly Glu Gly Glu Lys Glu Leu Ala Glu Lys Glu Glu Trp Lys Lys
    690                 695                 700

Arg Asp Gly Glu Glu Gln Glu Gln Lys Glu Arg Glu Gln Gly His Gln
705                 710                 715                 720

Lys Glu Arg Asn Gln Glu Met Glu Glu Gly Gly Glu Glu Glu His Gly
                725                 730                 735

Glu Gly Glu Glu Glu Glu Gly Asp Arg Glu Glu Glu Glu Lys Glu
            740                 745                 750

Gly Glu Gly Lys Glu Glu Gly Glu Gly Glu Glu Val Glu Gly Glu Arg
        755                 760                 765

Glu Lys Glu Glu Gly Glu Arg Lys Lys Glu Glu Arg Ala Gly Lys Glu
    770                 775                 780

Glu Lys Gly Glu Glu Glu Gly Asp Gln Gly Glu Gly Glu Glu Glu Glu
785                 790                 795                 800

Thr Glu Gly Arg Gly Glu Glu Lys Glu Glu Gly Gly Glu Val Glu Gly
            805                 810                 815

Gly Glu Val Glu Glu Gly Lys Gly Glu Arg Glu Glu Glu Glu Glu Glu
            820                 825                 830

Gly Glu Gly Glu Glu Glu Glu Gly Glu Gly Glu Glu Glu Glu Gly Glu
        835                 840                 845

Gly Glu Glu Glu Glu Gly Glu Gly Lys Gly Glu Glu Glu Gly Glu Glu
    850                 855                 860

Gly Glu Gly Glu Glu Glu Gly Glu Glu Gly Glu Gly Glu Gly Glu Glu
865                 870                 875                 880

Glu Glu Gly Glu Gly Glu Gly Glu Glu Glu Gly Glu Gly Glu Gly Glu
            885                 890                 895

Glu Glu Glu Gly Glu Gly Glu Gly Glu Glu Glu Gly Glu Gly Glu Gly
        900                 905                 910

Glu Glu Glu Glu Gly Glu Gly Lys Gly Glu Glu Glu Gly Glu Glu Gly
    915                 920                 925

Glu Gly Glu Gly Glu Glu Glu Glu Gly Glu Gly Glu Gly Glu Asp Gly
    930                 935                 940

Glu Gly Glu Gly Glu Glu Glu Glu Gly Glu Trp Glu Gly Glu Glu Glu
945                 950                 955                 960

Glu Gly Glu Gly Glu Gly Glu Glu Glu Gly Glu Gly Glu Gly Glu Glu
            965                 970                 975

Gly Glu Gly Glu Gly Glu Glu Glu Gly Glu Gly Glu Gly Glu Glu
            980                 985                 990

Glu Glu Gly Glu Glu Glu Gly Glu  Glu Glu Gly Glu Gly  Glu Glu Glu
        995                 1000                 1005

Gly Glu  Gly Glu Gly Glu Glu  Glu Glu Glu Gly Glu  Val Glu Gly
    1010                 1015                 1020

Glu Val  Glu Gly Glu Glu Gly  Glu Gly Glu Gly Glu  Glu Glu Glu
    1025                 1030                 1035

Gly Glu  Glu Glu Gly Glu Glu  Arg Glu Lys Glu Gly  Glu Gly Glu
    1040                 1045                 1050

Glu Asn  Arg Arg Asn Arg Glu  Glu Glu Glu Glu Glu  Glu Gly Lys
```

-continued

```
      1055              1060              1065

Tyr Gln  Glu Thr Gly Glu Glu  Glu Asn Glu Arg Gln  Asp Gly Glu
     1070              1075              1080

Glu Tyr  Lys Lys Val Ser Lys  Ile Lys Gly Ser Val  Lys Tyr Gly
     1085              1090              1095

Lys His  Lys Thr Tyr Gln Lys  Lys Ser Val Thr Asn  Thr Gln Gly
     1100              1105              1110

Asn Gly  Lys Glu Gln Arg Ser  Lys Met Pro Val Gln  Ser Lys Arg
     1115              1120              1125

Leu Leu  Lys Asn Gly Pro Ser  Gly Ser Lys Lys Phe  Trp Asn Asn
     1130              1135              1140

Val Leu  Pro His Tyr Leu Glu  Leu Lys
     1145              1150
```

<210> SEQ ID NO 16
<211> LENGTH: 4733
<212> TYPE: DNA
<213> ORGANISM: Artificial Sequence
<220> FEATURE:
<223> OTHER INFORMATION: Synthetic

<400> SEQUENCE: 16

```
gtagttgatc tccggagttt cgccatgcgg aacttggggg ctttcgcggc ccgcgtcggt      60
gcggagtagc tgctttagcc ccgaccaaac cgtcctctac agcctcctgg ccccggcgca     120
ggctgcccgt actgcccgtg gcatgaggga gccggaagag ctgatgcccg attcgggtgc     180
tgtgtttaca tttgggaaaa gtaaatttgc tgaaaataat cccggtaaat tctggtttaa     240
aaatgatgtc cctgtacatc tttcatgtgg agatgaacat tctgctgttg ttaccggaaa     300
taataaactt tacatgtttg gcagtaacaa ctggggtcag ttaggattag gatcaaagtc     360
agccatcagc aagccaacat gtgtcaaagc tctaaaacct gaaaaagtga aattagctgc     420
ctgtggaagg aaccacaccc tggtgtcaac agaaggaggc aatgtatatg caactggtgg     480
aaataatgaa ggacagttgg ggcttggtga caccgaagaa agaaacactt ttcatgtaat     540
tagctttttt acatccgagc ataagattaa gcagctgtct gctggatcta atacttcagc     600
tgccctaact gaggatggaa gacttttttat gtggggtgac aattccgaag ggcaaattgg     660
tttaaaaaat gtaagtaatg tctgtgtccc tcagcaagtg accattggga aacctgtctc     720
ctggatctct tgtggatatt accattcagc ttttgtaaca acagatggtg agctatatgt     780
gtttggagaa cctgagaatg ggaagttagg tcttcccaat cagctcctgg gcaatcacag     840
aacaccccag ctggtgtctg aaattccgga gaaggtgatc caagtagcct gtggtggaga     900
gcatactgtg gttctcacgg agaatgctgt gtatacctttt gggctgggac aatttggtca     960
gctgggtctt ggcactttttc tttttgaaac ttcagaaccc aaagtcattg agaatattag    1020
ggatcaaaca ataagttata tttcttgtgg agaaaatcac acagctttga taacagatat    1080
cggccttatg tatactttttg agatggtcg ccacggaaaa ttaggacttg gactggagaa    1140
ttttaccaat cacttcattc ctactttgtg ctctaatttt ttgaggttta tagttaaatt    1200
ggttgcttgt ggtggatgtc acatggtagt ttttgctgct cctcatcgtg gtgtggcaaa    1260
agaaattgaa ttcgatgaaa taaatgatac ttgcttatct gtggcgactt ttctgccgta    1320 tagcagtttta acctcaggaa atgtactgca gaggactcta tcagcacgta tgcggcgaag    1380
agagagggag aggtctccag attctttttc aatgaggaga acactacctc caatagaagg    1440
gactcttggc ctttctgctt gttttctccc caattcagtc tttccacgat gttctgagag    1500
```

```
aaacctccaa gagagtgtct tatctgaaca ggacctcatg cagccagagg aaccagatta   1560
tttgctagat gaaatgacca aagaagcaga gatagataat tcttcaactg tagaaagcct   1620
tggagaaact actgatatct taaacatgac acacatcatg agcctgaatt ccaatgaaaa   1680
gtcattaaaa ttatcaccag ttcagaaaca aaagaaacaa caaacaattg gggaactgac   1740
gcaggataca gctcttactg aaaacgatga tagtgatgaa tatgaagaaa tgtcagaaat   1800
gaaagaaggg aaagcatgta aacaacatgt gtcacaaggg attttcatga cgcagccagc   1860
tacgactatc gaagcatttt cagatgagga agtagagatc ccagaggaga aggaaggagc   1920
agaggattca aaaggaaatg gaatagagga gcaagaggta gaagcaaatg aggaaaatgt   1980
gaaggtgcat ggaggaagaa aggagaaaac agagatccta tcagatgacc ttacagacaa   2040
agcagaggtg agtgaaggca aggcaaaatc agtgggagaa gcagaggatg ggcctgaagg   2100 tagagggat ggaacctgtg aggaaggtag ttcaggagca gaacactggc aagatgagga   2160
gagggagaag ggggagaaag acaagggtag aggagaaatg gagaggccag gagagggaga   2220
gaaggaacta gcagagaagg aagaatggaa gaagagggat ggggaagagc aggagcaaaa   2280
ggagagggag cagggccatc agaaggaaag aaaccaagag atggaggagg gaggggagga   2340
ggagcatgga gaaggagaag aagaggaggg agacagagaa gaggaagaag agaaggaggg   2400
agaagggaaa gaggaaggag aaggggaaga agtggaggga gaacgtgaaa aggaggaagg   2460
agagaggaaa aaggaggaaa gagcgggaa ggaggagaaa ggagaggaag aaggagacca   2520
aggagagggg gaagaggagg aaacagaggg gagaggggag gaaaaagagg agggaggggga   2580 agtagaggga ggggaagtag aggaggggaa aggagagagg gaagaggaag aggaggaggg   2640 tgaggggaa gaggaggaag gggagggggga agaggaggaa ggggaggggg aagaggagga   2700
aggagaaggg aaagggggagg aagaaggggga agaaggagaa ggggaggaag aaggggagga   2760
aggagaaggg gaggggaag aggaggaagg agaaggggag ggagaagagg aaggagaagg   2820
ggagggagaa gaggaggaag gagaaggggga gggagaagag gaaggagaag gggagggaga   2880
agaggaggaa ggagaaggga aagggggagga ggaaggagag gaaggagaag gggaggggga   2940
agaggaggaa ggagaagggg aaggggagga tggagaaggg gaggggaag aggaggaagg   3000 agaatgggag ggggaagagg aggaaggaga aggggagggg gaagaggaag gagaaggggga   3060 aggggaggga ggagaaggggg aggggggaaga ggaggaagga gaaggggagg gggaagagga   3120
ggaaggggaa gaagaggggg aggaagaagg agagggagag gaagaagggg agggagaagg   3180
ggaggaagaa gaggaagggg aagtggaagg ggaggtggaa ggggaggaag gagaggggga   3240
aggagaggaa gaggaaggag aggaggaagg agaagaaagg gaaaaggagg gggaaggaga   3300
agaaaacagg aggaacagag aagaggagga ggaagaagag gggaagtatc aggagacagg   3360
cgaagaagag aatgaaaggc aggatggaga ggagtacaaa aaagtgagca aaataaaagg   3420
atctgtgaaa tatggcaaac ataaaacata tcaaaaaag tcagttacta acacacaggg   3480
aaatgggaaa gagcagaggt ccaaaatgcc agtccagtca aaacgacttt taaaaaacgg   3540
gccatcaggt tccaaaaagt tctggaataa tgtattacca cattacttgg aattgaagta   3600
acaaccttaa aatgtgaccc gattatggcc agtcagacaa tttaaatgcc ttgcatataa   3660
cgggcactca ttacgtgtta ttaaattgat tttatgtcaa ttattttatg tgtagtaaaa   3720
aaaaaagcaa ctgatgcagc tgtgttaagg agccaaagac aataggaggc actggtaaat   3780
tttggcctct ctcaaactaa aattttcgtg tatttccccc ccaaattata aaaacataac   3840
```

-continued

```
tagaaaatat taaaaggtca tatcagatta ttaacattat atattcatta aaggcagctt    3900
taggaaacag gaatatacta caagagtgtt ttgtttgtgt atacaaatca ttccattttt    3960
aaatggcaca gatgcttaag ggctataaaa acttctaatt tcttataaat atgttagcac    4020 ttttttaag ttagtgatta cagtttacct actgtataga ataattttct aataatggat     4080
ggtattctaa aactcaattg aggcattcac attttaaaga aagtattgtc tttcaccttt    4140
tatgtgttct ttttgcaaaa atctacaaag tgacagctgt gttcagagct tagatcccaa    4200
aaacgtgatc tcttttagtt actatctggg cagatggtag tatatctaat gaaatggtga    4260
ttaatttaaa tgtataatct ggaaatatgt aaaacttgaa gtattttttg tccaggcaaa    4320
ggtactcatt gggcctcagt ttcttcatct ctaaaatgga gtggatgaga tgatgtgata    4380
actgcagtcc cttctaactc ttaaattctt ttcattctca cagattcact ctatcattat    4440
tgttattcat gtaagaaacg ttttaggggag aaaaattaca ctttaaaatt aatttagttt    4500
tctatacagt tgttttcttt actcttgaaa agttatgaca gctttaacgt ctcttgtctt    4560
ctgtaatttt ttatttctaa actcctatca tttccaagct ttaactgtac tttatcagag    4620
ccttcatttc tggtatgtgt tatatgccct caatgtattc actgactgtt ctgtaatttc    4680
agtttgtctg ttccttgtca gaatgtttca agtaaaataa aaaattaaat gta           4733
```

```
<210> SEQ ID NO 17
<211> LENGTH: 1164
<212> TYPE: PRT
<213> ORGANISM: Artificial Sequence
<220> FEATURE:
<223> OTHER INFORMATION: Synthetic

<400> SEQUENCE: 17

Met Arg Glu Pro Glu Glu Leu Met Pro Asp Ser Gly Ala Val Phe Thr
1               5                   10                  15

Phe Gly Lys Ser Lys Phe Ala Glu Asn Asn Pro Gly Lys Phe Trp Phe
                20                  25                  30

Lys Asn Asp Val Pro Val His Leu Ser Cys Gly Asp Glu His Ser Ala
            35                  40                  45

Val Val Thr Gly Asn Asn Lys Leu Tyr Met Phe Gly Ser Asn Asn Trp
        50                  55                  60

Gly Gln Leu Gly Leu Gly Ser Lys Ser Ala Ile Ser Lys Pro Thr Cys
65                  70                  75                  80

Val Lys Ala Leu Lys Pro Glu Lys Val Lys Leu Ala Ala Cys Gly Arg
                85                  90                  95

Asn His Thr Leu Val Ser Thr Glu Gly Gly Asn Val Tyr Ala Thr Gly
                100                 105                 110

Gly Asn Asn Glu Gly Gln Leu Gly Leu Gly Asp Thr Glu Glu Arg Asn
            115                 120                 125

Thr Phe His Val Ile Ser Phe Phe Thr Ser Glu His Lys Ile Lys Gln
        130                 135                 140

Leu Ser Ala Gly Ser Asn Thr Ser Ala Ala Leu Thr Glu Asp Gly Arg
145                 150                 155                 160

Leu Phe Met Trp Gly Asp Asn Ser Glu Gly Gln Ile Gly Leu Lys Asn
                165                 170                 175

Val Ser Asn Val Cys Val Pro Gln Gln Val Thr Ile Gly Lys Pro Val
                180                 185                 190

Ser Trp Ile Ser Cys Gly Tyr Tyr His Ser Ala Phe Val Thr Thr Asp
            195                 200                 205
```

```
Gly Glu Leu Tyr Val Phe Gly Glu Pro Glu Asn Gly Lys Leu Gly Leu
    210                 215                 220

Pro Asn Gln Leu Leu Gly Asn His Arg Thr Pro Gln Leu Val Ser Glu
225                 230                 235                 240

Ile Pro Glu Lys Val Ile Gln Val Ala Cys Gly Gly Glu His Thr Val
                245                 250                 255

Val Leu Thr Glu Asn Ala Val Tyr Thr Phe Gly Leu Gly Gln Phe Gly
                260                 265                 270

Gln Leu Gly Leu Gly Thr Phe Leu Phe Glu Thr Ser Glu Pro Lys Val
            275                 280                 285

Ile Glu Asn Ile Arg Asp Gln Thr Ile Ser Tyr Ile Ser Cys Gly Glu
    290                 295                 300

Asn His Thr Ala Leu Ile Thr Asp Ile Gly Leu Met Tyr Thr Phe Gly
305                 310                 315                 320

Asp Gly Arg His Gly Lys Leu Gly Leu Gly Leu Glu Asn Phe Thr Asn
                325                 330                 335

His Phe Ile Pro Thr Leu Cys Ser Asn Phe Leu Arg Phe Ile Val Lys
            340                 345                 350

Leu Val Ala Cys Gly Gly Cys His Met Val Val Phe Ala Ala Pro His
            355                 360                 365

Arg Gly Val Ala Lys Glu Ile Glu Phe Asp Glu Ile Asn Asp Thr Cys
    370                 375                 380

Leu Ser Val Ala Thr Phe Leu Pro Tyr Ser Ser Leu Thr Ser Gly Asn
385                 390                 395                 400

Val Leu Gln Arg Thr Leu Ser Ala Arg Met Arg Arg Arg Glu Arg Glu
                405                 410                 415

Arg Ser Pro Asp Ser Phe Ser Met Arg Arg Thr Leu Pro Pro Ile Glu
                420                 425                 430

Gly Thr Leu Gly Leu Ser Ala Cys Phe Leu Pro Asn Ser Val Phe Pro
            435                 440                 445

Arg Cys Ser Glu Arg Asn Leu Gln Glu Ser Val Leu Ser Glu Gln Asp
    450                 455                 460

Leu Met Gln Pro Glu Glu Pro Asp Tyr Leu Leu Asp Glu Met Thr Lys
465                 470                 475                 480

Glu Ala Glu Ile Asp Asn Ser Ser Thr Val Glu Ser Leu Gly Glu Thr
                485                 490                 495

Thr Asp Ile Leu Asn Met Thr His Ile Met Ser Leu Asn Ser Asn Glu
            500                 505                 510

Lys Ser Leu Lys Leu Ser Pro Val Gln Lys Gln Lys Lys Gln Gln Thr
            515                 520                 525

Ile Gly Glu Leu Thr Gln Asp Thr Ala Leu Thr Glu Asn Asp Asp Ser
    530                 535                 540

Asp Glu Tyr Glu Glu Met Ser Glu Met Lys Glu Gly Lys Ala Cys Lys
545                 550                 555                 560

Gln His Val Ser Gln Gly Ile Phe Met Thr Gln Pro Ala Thr Thr Ile
                565                 570                 575

Glu Ala Phe Ser Asp Glu Glu Val Ala Thr Thr Ile Glu Ala Phe Ser
                580                 585                 590

Asp Glu Glu Val Glu Ile Pro Glu Glu Lys Glu Gly Ala Glu Asp Ser
            595                 600                 605

Lys Gly Asn Gly Ile Glu Glu Gln Glu Val Glu Ala Asn Glu Glu Asn
    610                 615                 620

Val Lys Val His Gly Gly Arg Lys Glu Lys Thr Glu Ile Leu Ser Asp
```

```
625                 630                 635                 640

Asp Leu Thr Asp Lys Ala Glu Val Ser Glu Gly Lys Ala Lys Ser Val
                645                 650                 655

Gly Glu Ala Glu Asp Gly Pro Glu Gly Arg Gly Asp Gly Thr Cys Glu
                660                 665                 670

Glu Gly Ser Ser Gly Ala Glu His Trp Gln Asp Glu Arg Glu Lys
                675                 680                 685

Gly Glu Lys Asp Lys Gly Arg Gly Glu Met Glu Arg Pro Gly Glu Gly
                690                 695                 700

Glu Lys Glu Leu Ala Glu Lys Glu Glu Trp Lys Lys Arg Asp Gly Glu
705                 710                 715                 720

Glu Gln Glu Gln Lys Glu Arg Glu Gln Gly His Gln Lys Glu Arg Asn
                725                 730                 735

Gln Glu Met Glu Glu Gly Gly Glu Glu His Gly Glu Gly Glu Glu
                740                 745                 750

Glu Glu Gly Asp Arg Glu Glu Glu Glu Lys Glu Gly Glu Gly Lys
                755                 760                 765

Glu Glu Gly Glu Gly Glu Glu Val Glu Gly Glu Arg Glu Lys Glu Glu
                770                 775                 780

Gly Glu Arg Lys Lys Glu Glu Arg Ala Gly Lys Glu Glu Lys Gly Glu
785                 790                 795                 800

Glu Glu Gly Asp Gln Gly Glu Gly Glu Glu Glu Thr Glu Gly Arg
                805                 810                 815

Gly Glu Glu Lys Glu Glu Gly Gly Glu Val Glu Gly Gly Glu Val Glu
                820                 825                 830

Glu Gly Lys Gly Glu Arg Glu Glu Glu Glu Glu Gly Glu Gly Glu
                835                 840                 845

Glu Glu Glu Gly Glu Gly Glu Glu Glu Gly Glu Gly Glu Glu Glu
                850                 855                 860

Glu Gly Glu Gly Lys Gly Glu Glu Glu Gly Glu Glu Gly Glu Gly Glu
865                 870                 875                 880

Glu Glu Gly Glu Glu Gly Glu Gly Glu Gly Glu Glu Glu Glu Gly Glu
                885                 890                 895

Gly Glu Gly Glu Glu Glu Gly Glu Gly Glu Gly Glu Glu Glu Gly
                900                 905                 910

Glu Gly Glu Gly Glu Glu Glu Gly Glu Gly Glu Gly Glu Glu Glu Glu
                915                 920                 925

Gly Glu Gly Lys Gly Glu Glu Glu Gly Glu Glu Gly Glu Gly Glu Gly
                930                 935                 940

Glu Glu Glu Glu Gly Glu Gly Glu Gly Glu Asp Gly Glu Gly Glu Gly
945                 950                 955                 960

Glu Glu Glu Glu Gly Glu Trp Glu Gly Glu Glu Glu Gly Glu Gly
                965                 970                 975

Glu Gly Glu Glu Glu Gly Glu Gly Glu Gly Glu Glu Gly Glu Gly Glu
                980                 985                 990

Gly Glu Glu Glu Glu Gly Glu Gly  Glu Gly Glu Glu Glu  Glu Gly Glu
                995                 1000                1005

Glu Glu  Gly Glu Glu Glu Gly  Glu Gly Glu Glu Glu  Gly Glu Gly
     1010                1015                1020

Glu Gly  Glu Glu Glu Glu Glu  Gly Glu Val Glu Gly  Glu Val Glu
     1025                1030                1035

Gly Glu  Glu Gly Glu Gly Glu  Gly Glu Glu Glu Glu  Gly Glu Glu
     1040                1045                1050
```

```
Glu Gly  Glu Glu Arg Glu Lys  Glu Gly Glu Gly Glu  Glu Asn Arg
    1055             1060                 1065

Arg Asn  Arg Glu Glu Glu Glu  Glu Glu Glu Gly Lys  Tyr Gln Glu
    1070             1075                 1080

Thr Gly  Glu Glu Glu Asn Glu  Arg Gln Asp Gly Glu  Glu Tyr Lys
    1085             1090                 1095

Lys Val  Ser Lys Ile Lys Gly  Ser Val Lys Tyr Gly  Lys His Lys
    1100             1105                 1110

Thr Tyr  Gln Lys Lys Ser Val  Thr Asn Thr Gln Gly  Asn Gly Lys
    1115             1120                 1125

Glu Gln  Arg Ser Lys Met Pro  Val Gln Ser Lys Arg  Leu Leu Lys
    1130             1135                 1140

Asn Gly  Pro Ser Gly Ser Lys  Lys Phe Trp Asn Asn  Val Leu Pro
    1145             1150                 1155

His Tyr  Leu Glu Leu Lys
    1160
```

```
<210> SEQ ID NO 18
<211> LENGTH: 3495
<212> TYPE: DNA
<213> ORGANISM: Artificial Sequence
<220> FEATURE:
<223> OTHER INFORMATION: Synthetic

<400> SEQUENCE: 18
atgagggagc cggaagagct gatgcccgat tcgggtgctg tgtttacatt tgggaaaagt      60
aaatttgctg aaaataatcc cggtaaattc tggtttaaaa atgatgtccc tgtacatctt     120
tcatgtggag atgaacattc tgctgttgtt accggaaata ataaacttta catgtttggc     180
agtaacaact ggggtcagtt aggattagga tcaaagtcag ccatcagcaa gccaacatgt     240
gtcaaagctc taaaacctga aaaagtgaaa ttagctgcct gtggaaggaa ccacaccctg     300
gtgtcaacag aaggaggcaa tgtatatgca actggtggaa ataatgaagg acagttgggg     360
cttggtgaca ccgaagaaag aaacactttt catgtaatta gctttttttac atccgagcat     420 aagattaagc agctgtctgc tggatctaat acttcagctg ccctaactga ggatggaaga     480 cttttttatgt ggggtgacaa ttccgaaggg caaattggtt taaaaaatgt aagtaatgtc     540
tgtgtccctc agcaagtgac cattgggaaa cctgtctcct ggatctcttg tggatattac     600
cattcagctt ttgtaacaac agatggtgag ctatatgtgt ttggagaacc tgagaatggg     660
aagttaggtc ttcccaatca gctcctgggc aatcacagaa cacccccagct ggtgtctgaa     720 attccggaga aggtgatcca agtagcctgt ggtggagagc atactgtggt tctcacggag     780
aatgctgtgt atacctttgg gctgggacaa tttggtcagc tgggtcttgg cactttttctt     840 tttgaaactt cagaacccaa agtcattgag aatattaggg atcaaacaat aagttatatt     900
tcttgtggag aaaatcacac agctttgata acagatatcg gccttatgta acttttttgga     960 gatggtcgcc acggaaaatt aggacttgga ctggagaatt ttaccaatca cttcattcct    1020
actttgtgct ctaattttttt gaggtttata gttaaattgg ttgcttgtgg tggatgtcac    1080
atggtagttt ttgctgctcc tcatcgtggt gtggcaaaag aaattgaatt cgatgaaata    1140
aatgatactt gcttatctgt ggcgactttt ctgccgtata gcagtttaac ctcaggaaat    1200
gtactgcaga ggactctatc agcacgtatg cggcgaagag agagggagag gtctccagat    1260 tcttttttcaa tgaggagaac actacctcca atagaaggga ctcttggcct ttctgcttgt    1320
```

```
tttctcccca attcagtctt tccacgatgt tctgagagaa acctccaaga gagtgtctta      1380
tctgaacagg acctcatgca gccagaggaa ccagattatt tgctagatga aatgaccaaa      1440
gaagcagaga tagataattc ttcaactgta gaaagccttg gagaaactac tgatatctta      1500
aacatgacac acatcatgag cctgaattcc aatgaaaagt cattaaaatt atcaccagtt      1560
cagaaacaaa agaaacaaca aacaattggg gaactgacgc aggatacagc tcttactgaa      1620
aacgatgata gtgatgaata tgaagaaatg tcagaaatga aagaagggaa agcatgtaaa      1680
caacatgtgt cacaagggat tttcatgacg cagccagcta cgactatcga agcattttca      1740
gatgaggaag tagctacgac tatcgaagca ttttcagatg aggaagtaga gatcccagag      1800
gagaaggaag gagcagagga ttcaaaagga aatggaatag aggagcaaga ggtagaagca      1860
aatgaggaaa atgtgaaggt gcatggagga agaaaggaga aaacagagat cctatcagat      1920
gaccttacag acaaagcaga ggtgagtgaa ggcaaggcaa aatcagtggg agaagcagag      1980
gatgggcctg aaggtagagg ggatggaacc tgtgaggaag gtagttcagg agcagaacac      2040
tggcaagatg aggagaggga gaagggggag aaagacaagg gtagaggaga aatggagagg      2100
ccaggagagg gagagaagga actagcagag aaggaagaat ggaagaagag ggatggggaa      2160
gagcaggagc aaaaggagag ggagcagggc catcagaagg aaagaaacca agagatggag      2220 gaggagggggg aggaggagca tggagaagga gaagaagagg agggagacag agaagaggaa      2280
gaagagaagg agggagaagg gaaagaggaa ggagaaggggg aagaagtgga gggagaacgt      2340
gaaaaggagg aaggagagag gaaaaaggag gaaagagcgg ggaaggagga gaaaggagag      2400
gaagaaggag accaaggaga gggggaagag gaggaaacag aggggagagg ggaggaaaaa      2460 gaggaggggag gggaagtaga gggagggggaa gtagaggagg ggaaaggaga gagggaagag      2520
gaagaggagg agggtgaggg ggaagaggag gaaggggagg gggaagagga ggaaggggag      2580
ggggaagagg aggaaggaga agggaaaggg gaggaagaag gggaagaagg agaaggggag      2640
gaagaagggg aggaaggaga aggggagggg gaagaggagg aaggagaagg ggagggagaa      2700
gaggaaggag aaggggaggg agaagaggag gaaggagaag gggaggggaga agaggaagga      2760 gaaggggagg gagaagagga ggaaggagaa gggaaagggg aggaggaagg agaggaagga      2820
gaaggggagg gggaagagga ggaaggagaa ggggaagggg aggatggaga aggggagggg      2880
gaagaggagg aaggagaatg ggaggggggaa gaggaggaag gagaagggga ggggggaagag      2940 gaaggagaag gggaagggga ggaaggagaa ggggaggggg aagaggagga aggagaaggg      3000 gaggggggaag aggaggaagg ggaagaagaa ggggaggaag aaggagaggg agaggaagaa      3060
ggggagggag aagggggaga agaagaggaa ggggaagtgg aagggggaggt ggaagggggag      3120 gaaggagagg gggaaggaga ggaagaggaa ggagaggagg aaggagaaga aagggaaaag      3180 gaggggggaag gagaagaaaa caggaggaac agagaagagg aggaggaaga agaggggaag      3240
tatcaggaga caggcgaaga agagaatgaa aggcaggatg gagaggagta caaaaaagtg      3300
agcaaaataa aaggatctgt gaaatatggc aaacataaaa catatcaaaa aaagtcagtt      3360
actaacacac agggaaatgg gaaagagcag aggtccaaaa tgccagtcca gtcaaaacga      3420
cttttaaaaa acgggccatc aggttccaaa aagttctgga ataatgtatt accacattac      3480
ttggaattga agtaa                                                     3495
```

<210> SEQ ID NO 19
<211> LENGTH: 20
<212> TYPE: DNA
<213> ORGANISM: Artificial Sequence

```
<220> FEATURE:
<223> OTHER INFORMATION: Synthetic

<400> SEQUENCE: 19
gaacgggcca tttgtgagta                                              20

<210> SEQ ID NO 20
<211> LENGTH: 21
<212> TYPE: DNA
<213> ORGANISM: Artificial Sequence
<220> FEATURE:
<223> OTHER INFORMATION: Synthetic

<400> SEQUENCE: 20
ggttctggtc ggcatcttta t                                           21

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
ggaaggagca gaggattcaa a                                           21

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
cctcatcttg ccagtgttct                                             20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gacctctatg ccaacacagt                                             20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
agtacttgcg ctcaggagga                                             20

<210> SEQ ID NO 25
<211> LENGTH: 23
<212> TYPE: DNA
<213> ORGANISM: Artificial Sequence
<220> FEATURE:
<223> OTHER INFORMATION: Synthetic

<400> SEQUENCE: 25
gcatcagtac cccattctat cat                                         23
```

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
aggtgtaatc cgtctccaca ga                                                                                      22

<210> SEQ ID NO 27
<211> LENGTH: 25
<212> TYPE: RNA
<213> ORGANISM: Artificial Sequence
<220> FEATURE:
<223> OTHER INFORMATION: Synthetic

<400> SEQUENCE: 27
cuuccucucu uucucucccu uguga                                                                                   25

<210> SEQ ID NO 28
<211> LENGTH: 27
<212> TYPE: RNA
<213> ORGANISM: Artificial Sequence
<220> FEATURE:
<223> OTHER INFORMATION: Synthetic

<400> SEQUENCE: 28
aggaaggaga gaaagagagg gaacacu                                                                                 27

<210> SEQ ID NO 29
<211> LENGTH: 25
<212> TYPE: RNA
<213> ORGANISM: Artificial Sequence
<220> FEATURE:
<223> OTHER INFORMATION: Synthetic

<400> SEQUENCE: 29
caccaagcaa agacaugaaa aaaac                                                                                   25

<210> SEQ ID NO 30
<211> LENGTH: 27
<212> TYPE: RNA
<213> ORGANISM: Artificial Sequence
<220> FEATURE:
<223> OTHER INFORMATION: Synthetic

<400> SEQUENCE: 30
uugugguucg uuucuguacu uuuuuug                                                                                 27

<210> SEQ ID NO 31
<211> LENGTH: 25
<212> TYPE: DNA
<213> ORGANISM: Artificial Sequence
<220> FEATURE:
<223> OTHER INFORMATION: Synthetic

<400> SEQUENCE: 31
ggagcagaaa gaaccaauga ugata                                                                                   25

```
<210> SEQ ID NO 32
<211> LENGTH: 27
<212> TYPE: RNA
<213> ORGANISM: Artificial Sequence
<220> FEATURE:
<223> OTHER INFORMATION: Synthetic

<400> SEQUENCE: 32
uuccucgucu uucuugguua cuacuau                                          27

<210> SEQ ID NO 33
<211> LENGTH: 25
<212> TYPE: RNA
<213> ORGANISM: Artificial Sequence
<220> FEATURE:
<223> OTHER INFORMATION: Synthetic

<400> SEQUENCE: 33
aucaaaagau ugucaagaau aacaa                                            25

<210> SEQ ID NO 34
<211> LENGTH: 27
<212> TYPE: RNA
<213> ORGANISM: Artificial Sequence
<220> FEATURE:
<223> OTHER INFORMATION: Synthetic

<400> SEQUENCE: 34
uuuaguuuuc uaacaguucu uauuguu                                          27

<210> SEQ ID NO 35
<211> LENGTH: 96
<212> TYPE: DNA
<213> ORGANISM: Artificial Sequence
<220> FEATURE:
<223> OTHER INFORMATION: Synthetic

<400> SEQUENCE: 35
catcaacaac atactttttg ggatctgtaa gggcttcaag tattctggtc acagaataca     60
acatactttt tgggatctgt aagggcttca agcaag                               96

<210> SEQ ID NO 36
<211> LENGTH: 93
<212> TYPE: DNA
<213> ORGANISM: Artificial Sequence
<220> FEATURE:
<223> OTHER INFORMATION: Synthetic

<400> SEQUENCE: 36
catcaacagc ctatcctgga tctccaggat aggctcaagt attctggtca cagaatacaa     60
cagcctatcc tggatctcca ggataggctc aag                                  93
```